United States Patent
Kimura et al.

[11] Patent Number: 6,137,581
[45] Date of Patent: Oct. 24, 2000

[54] MEASUREMENT APPARATUS FOR MEASURING INTERNAL QUALITY OF OBJECT

[75] Inventors: Mikio Kimura; Toyohiko Aoki; Hirotsugu Hashimoto; Takeshi Ota; Akihiko Fujita, all of Ageo, Japan

[73] Assignee: Mitsui Mining & Smelting Co., Ltd., Tokyo, Japan

[21] Appl. No.: 09/301,688

[22] Filed: Apr. 29, 1999

[30] Foreign Application Priority Data

| May 15, 1998 | [JP] | Japan | 10-133338 |
| May 20, 1998 | [JP] | Japan | 10-138362 |
| May 20, 1998 | [JP] | Japan | 10-138363 |

[51] Int. Cl.$^7$ .......................... H04N 1/415; G01N 21/00; B07C 5/342
[52] U.S. Cl. ................ 356/433; 356/237.1; 209/581; 209/588; 209/589
[58] Field of Search .................... 356/433, 444, 356/432, 375, 237.1, 229, 222, 243.8; 209/509, 577, 581, 588, 689

[56] References Cited

U.S. PATENT DOCUMENTS

| 3,554,654 | 1/1971 | Paatzsch et al. | 356/180 |
| 3,609,047 | 9/1971 | Marlow | 356/205 |
| 3,773,172 | 11/1973 | McClure et al. | 209/73 |
| 3,930,994 | 1/1976 | Conway et al. | 209/74 |
| 4,735,323 | 4/1988 | Okada et al. | 209/582 |
| 5,726,750 | 3/1998 | Ito et al. | 356/244 |
| 5,845,002 | 12/1998 | Heck et al. | 382/110 |

FOREIGN PATENT DOCUMENTS

| 6-213804 | 8/1994 | Japan . |
| 7-63616 | 3/1995 | Japan . |

OTHER PUBLICATIONS

Patent Abstracts of Japan; Pub. No. 06–300680; Pub. Date: Oct. 28, 1994.
Patent Abstracts of Japan; Pub. No. 04–115142; Pub. Date: Apr. 16, 1992.
Patent Abstracts of Japan; Pub. No. 09–015142; Pub. Date: Jan. 17, 1997.
Patent Abstracts of Japan; Pub. No. 06–300689; Pub. Date: Oct. 28, 1994.
Patent Abstracts of Japan; Pub. No. 06–213804; Pub. Date: Aug. 5, 1994.
Patent Abstracts of Japan; Pub. No. 07–63616; Pub. Date: Mar. 10, 1995.

*Primary Examiner*—Frank G. Font
*Assistant Examiner*—Layla Lauchman
*Attorney, Agent, or Firm*—Kubovcik & Kubovcik

[57] ABSTRACT

The present invention relates to an internal quality measuring apparatus for measuring an internal quality of an object, and the apparatus has a conveying device, a detecting device, a light projecting device, a light receiving device, an analyzing device and a pseudo-object member interposing device, and the analyzing device compares light received with a pseudo-object member, with reference data preliminarily stored, and correct a result of the analysis, based thereon.

106 Claims, 27 Drawing Sheets

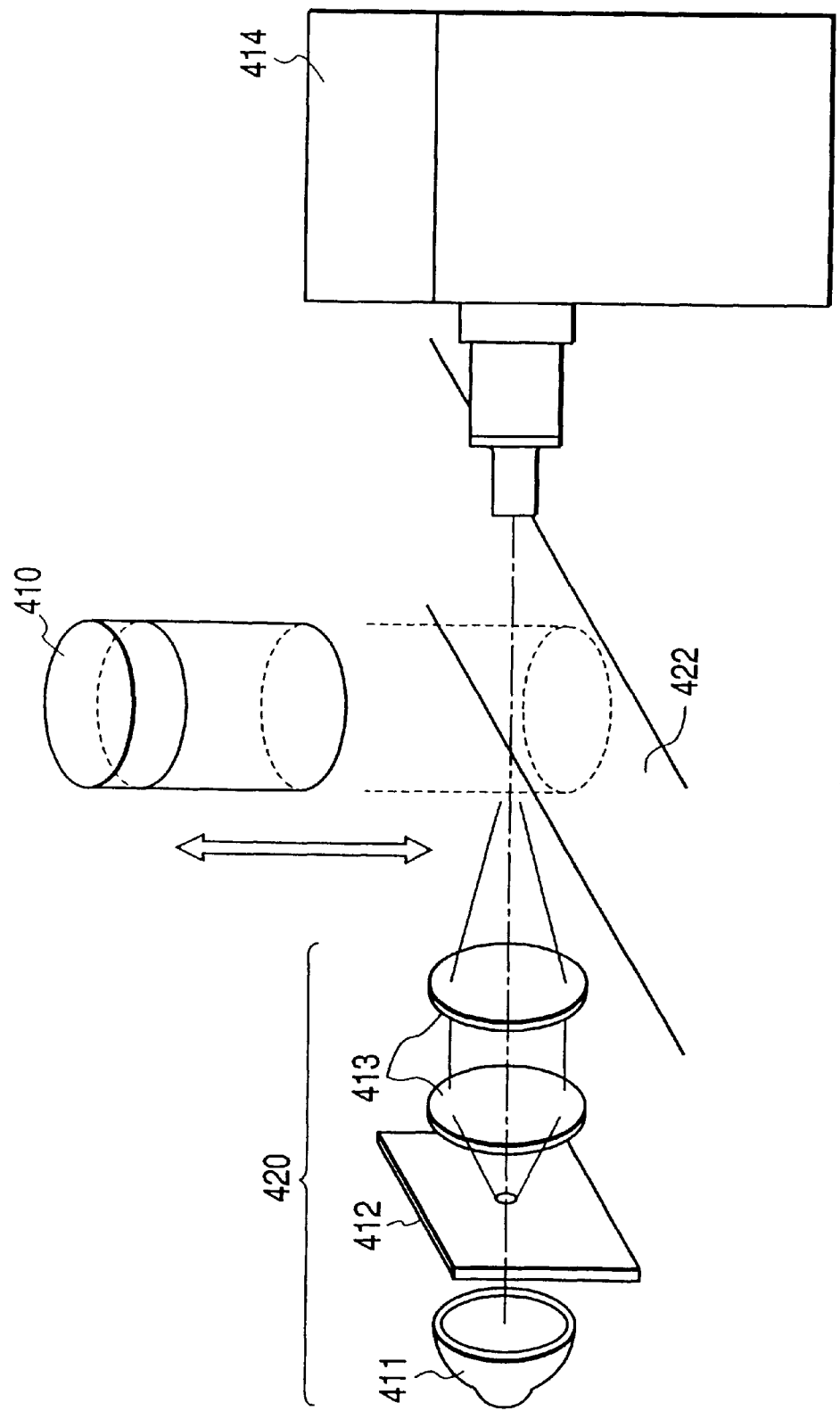

MEASUREMENT APPARATUS FOR MEASURING INTERNAL QUALITY OF OBJECT

BACKGROUND OF THE INVENTION

1. Field of the Invention

The present invention relates to an apparatus for measuring an internal quality of such an object as the greengrocery (fruits and vegetables) on a nondestructive basis.

2. Related Background Art

An example of the conventional apparatus for measuring the internal quality of the fruits or vegetables on a nondestructive basis was a device disclosed, for example, in Japanese Patent Application Laid-Open No. 6-213804. The conventional apparatus will be described below referring to FIG. 37 and FIG. 38.

In the apparatus illustrated in FIG. 37, light 854 is projected from lamp 853 toward an object to be inspected (inspected object) 852 such as a mandarin, an orange, an apple, or the like mounted on belt conveyor 850 and a spectroscope 858 receives light 856 having been transmitted by and emitted from the inspected object 852. The spectroscope 858 measures an absorption spectrum of the transmitted light 824 and the internal quality of the inspected object can be determined based on the absorption spectrum.

With this apparatus, variations occurred in measured values as a plurality of inspected objects 852 on the conveyor 850 were measured continuously. This is conceivably caused by change of a base line (which is a value as a reference of measurement) of the measured values of the spectroscope with a lapse of measurement time. This change mainly results from changes of the spectroscope and the apparatus itself and from change in ambient circumstances.

Another device for measuring the internal quality of the fruits or vegetables such as melons or the like on a nondestructive basis was, for example, a device disclosed in Japanese Patent Application Laid-Open No. 6-288903. The conventional device will be described below referring to FIG. 39.

In this device, near-infrared light is projected from lamps 876 toward the inspected object 874 such as a melon or the like mounted on a shield basket 872 on belt conveyor 870 and the spectroscope 880 receives light having been transmitted by and emitted from the inspected object 874 through optical fiber 878. The spectroscope 880 measures an absorption spectrum of the transmitted light and the internal quality of the inspected object 880 can be determined based on this absorption spectrum.

With this device, variations occurred in measured values as a plurality of inspected objects 874 each mounted on a plurality of shield baskets 872 were measured continuously. This is conceivably caused by change of the base line (which is a value as a reference or standard of measurement) of the measured values of the spectroscope 880 with a lapse of measurement time. This change mainly results from changes in the spectroscope 880 and in the ambient circumstances.

With the conventional apparatus, however, adjustment (i.e., calibration) of the base line changing with a lapse of measurement time was carried out only at the start of measurement, so that the variations occurred in the measured values with progress of measurement with a lapse of time.

On the other hand, for carrying out the calibration in the middle of the measurement, the conveyor line had to be stopped on every occasion of calibration and the measurement also had to be suspended. Therefore, the measurement time was lengthened for execution of the calibration.

In the apparatus illustrated in FIG. 38, light 862 reflected by half mirror 860 is projected toward the inspected object 852 mounted on the belt conveyor 850 and the spectroscope 858 receives light 864 having been reflected by the inspected object 852 and having passed through the half mirror 860, whereby the internal quality of the inspected object 852 can be determined as in the case of the apparatus of FIG. 37. In this device the spectroscope 858 and reference reflecting plate 866 for calibration are opposed to each other on either side of the belt conveyor 850 and with the reflected light from this reflecting plate 866 the calibration can be carried out at a position where the inspected object is absent on the conveyor 850.

The calibration according to this method, however, cannot be applied to the device of FIG. 37 for measuring the light having been transmitted by the inspected object.

An object of the present invention is, therefore, to provide a device for measuring an internal quality of a fruit or vegetable with light having been transmitted by the inspected object, the device being arranged in such structure that the calibration of the device can be carried out without interruption of the measurement, so as to eliminate the change of the base line, whereby the internal quality of the fruit or vegetable can be measured accurately.

On the other hand, in the measurement of the internal quality by spectral analysis as described above, it is common practice to project the light from the light source such as a halogen lamp or the like toward the fruit or vegetable, divide the transmitted light through the fruit or vegetable into a plurality of channels having different wavelengths, convert the intensity of the transmitted light in each channel to current, measure the current to detect an absorption spectrum of the fruit or vegetable, and determine a sugariness or the like of the fruit or vegetable, based thereon. In such measurement, it is inevitable to suffer fluctuations of the light source lamp, specifically, temporal change and deterioration of spectral characteristics (color temperature), and fluctuations due to environmental change of ambient temperature or the like on one hand and it is also inevitable to experience fluctuations and the like due to temporal change or environmental change of the measurement system on the other hand, which results in causing errors in the measurement.

In order to avoid it, in the case of such measurement, the calibration of the device is carried out at intervals of a certain time. The calibration is carried out by measuring the quantity of the transmitted light through a predetermined calibration body instead of the fruit or vegetable being an object originally intended to be inspected. A typical calibration method is as follows. In each wavelength channel, a measurement transmittance T is calculated according to the following equation to effect the calibration:

$$T = I_s / I_r$$

where $I_r$ is the intensity of the transmitted light (more exactly, intensity of current converted therefrom) through the calibration body and $I_s$ is the intensity of the transmitted light (more exactly, intensity of current converted therefrom) of the fruit or vegetable to be inspected. Namely, a value of transmittance of an inspected object is calibrated by taking a ratio thereof to the transmittance of the calibration body, thereby canceling the change of the transmitted light due to the variations of the light source and the measurement system.

For more accurate measurement, the transmittance is also sometimes computed according to the following equation:

$$T=(I_s-D)/(I_r-D)$$

where D is dark current of the measurement system when the input into the spectroscope is zero.

The calibration body used in such calibration is normally an object with flat absorption characteristics such as an ND filter (neutral density filter) or the like. The reason why the light from the light source is not monitored directly but is monitored through the ND filter on the occasion of the calibration is that the intensity of light needs to be of a light intensity level close to the intensity of the transmitted light through actual inspected bodies in order to make the calibration accurate. It is, therefore, common practice to select the transmittance of the ND filter for calibration so that the quantity of the transmitted light therethrough is within a predetermined range with respect to the quantity of the transmitted light through the actual inspected bodies.

As described above, the calibration is carried out using the calibration body such as the ND filter or the like against the various variations of the measuring device. However, the fruits or vegetables being actual inspected objects have specific light absorption characteristics, because the principal component thereof is water; whereas the ND filter has the flat absorption characteristics. Because of this great difference in the absorption characteristics, the flat absorption characteristics of the ND filter cannot follow the largely changing absorption characteristics of the fruits or vegetables, so that the intensity of the transmitted light through the calibration body and the intensity of the transmitted light through the inspected objects become heavily different from each other, depending upon the wavelengths, which poses a problem of failing to effect the calibration with high accuracy.

There are problematic variations during the measurement by infrared spectral analysis, not only on the device side but also on the object side.

Specifically, the principle of the measurement of the internal quality such as the sugariness, acidity, or the like of the fruits or vegetables by the infrared spectral analysis is based on the fact that absorption occurs at specific wavelengths in the spectrum of transmitted light because of various groups (for example, functional groups such as O—H, C—H, and so on) of components in the fruits or vegetables being the inspected objects. The absorption spectra of the fruits or vegetables vary depending upon environmental changes of the temperature or the like and variations also occur in peak wavelengths of absorption by the groups. This results in introducing errors in the measurement of the internal quality by the spectral analysis. This is significant, particularly, in the measurement of the acidity of a low-content acid or the like. The ND filter does not have a variable property of the absorption characteristics against the environmental change, and thus the ND filter is inadequate as a calibration body in this aspect, too.

In the conventional measuring apparatus for measuring the internal quality of the fruits or vegetables by spectral analysis, the position where the calibration body is measured is different from the position where the inspected object is measured in the apparatus, which is a reason why variations of their absorption spectra measured are not synchronous.

The present invention provides a correction method which solves the above problem.

In addition, values of such internal qualities as the sugariness, acidity, grade of maturity, and so on of the fruits or vegetables differ depending upon locations in the fruits or vegetables. It is thus desirable to project the light toward the central part of the fruit or vegetable, in the apparatus arranged to project the light toward the fruit or vegetable and measure the internal quality thereof with the light transmitted thereby.

In the conventional example, however, the height of the projection light source was fixed, and, therefore, if the sizes of the fruits or vegetables being the inspected objects were different, irradiation positions were different between large inspected objects and small inspected objects. Namely, the light was projected toward the central part of inspected object with the small inspected objects, whereas the light was projected to the lower part of inspected object with the large inspected objects. It was not able to be mentioned that each of the inspected objects was measured under the same conditions.

On the other hand, the measuring device of this type is arranged to measure the internal quality of the fruit or vegetable by the absorption spectrum of the light having been transmitted by the fruit or vegetable, and it is desirable that the absorption spectrum have the intensity enough to implement accurate measurement.

However, the quantity of the light transmitted by the fruits or vegetables under irradiation of the light at constant quantity is sometimes very small, depending upon kinds of the fruits or vegetables. In that case the measurement becomes hard. In general, melons, watermelons, etc. transmit the light in small quantity while oranges etc. transmit the light in large quantity. For measuring the internal quality of the fruits or vegetables with the small quantity of transmitted light, the difference is unlikely to appear among intensities of the absorption spectra of the respective inspected objects and it is thus difficult to implement the measurement by the absorption spectra.

An object of the present invention is, therefore, to provide a measuring device for measuring an internal quality of a fruit or vegetable on a non-destructive basis while projecting light toward the fruit or vegetable, the measuring device being arranged to be capable of radiating the light to the vicinity of the equator part (an intersecting line between a horizontal plane including the central part of the inspected object and being parallel to the ground and the surface of the inspected object) of the inspected object, irrespective of the size of the inspected object and to be capable of changing the quantity of the projected light toward the fruit or vegetable according to a kind of the fruit or vegetable.

In many non-destructive measuring devices of fruits or vegetables for measuring the internal quality such as the sugariness, acidity, or the like of the fruits or vegetables by projecting the light such as the near-infrared light or the like toward the fruit or vegetable and measuring the absorption spectrum of the transmitted light, a plurality of fruits or vegetables as inspected objects are mounted on a conveying system such as a belt conveyor or the like and the measurement is carried out successively for the plurality of inspected objects under movement.

Specifically, located at a certain position in a conveyance path of the conveyor is a measurement unit comprised of a light projecting device for projecting the light toward the inspected object and a sensor for receiving the transmitted light from the inspected object to measure the absorption spectrum thereof, and the measurement is carried out when each inspected object passes the measuring position. Then the sugariness, acidity, or the like of each fruit or vegetable being an inspected object is computed based on the absorption spectrum obtained.

In this measuring device, it is desirable to implement the measurement at the center position of the fruit or vegetable being the inspected object in order to realize the measurement with less errors. Among the devices of this type, devices in such structure that buckets for accommodating individual inspected objects are provided on the conveyor and that the inspected objects are mounted on the respective buckets, permit easy determination of the correct measurement timing, i.e., easy determination of the timing when the inspected object passes the measuring position, because the positions of the inspected objects on the conveyor are preliminarily determined at the predetermined positions. On the other hand, in the case of the fruits or vegetables such as oranges or the like where a large amount of inspected objects need to be measured, a way of measuring them while such fruits or vegetables being the inspected objects are supplied and mounted at random on the flat belt conveyor by automatic supply means or the like is more useful in terms of measurement efficiency. In cases where the inspected objects are placed at random on the conveyor, it is, however, necessary to substantiate some means for carrying out the measurement at the correct measurement position, i.e., at the time when the center of the inspected object passes the measuring position. The present invention provides a method and an apparatus that enable such measurement.

When the fruits or vegetables such as oranges or the like are placed at random on the flat conveyor as described above, the inspected objects could rotate to move on the conveyor in some cases because of the property of the shape of the fruits or vegetables close to the sphere. In such cases there arises a problem that it is not clear whether an inspected object leaving the conveyor was measured at the normal position. The present invention also solves this problem.

Further, the apparatus of this type normally has moving means such as a belt conveyor or the like for continuously moving a plurality of fruits or vegetables along a conveyance path, a light source disposed at a predetermined position in a conveyance path established by the moving means and arranged to project light toward the fruit or vegetable on the moving means, and a light receiving sensor for receiving light travelling through the fruit or vegetable, as main components.

The devices conventionally known are generally classified as follows.

1) devices of a type in which the light receiving sensor is located at a position in a direction approximately equal to the direction of the light projected from the light source toward the fruit or vegetable of the inspected object and in which the measurement is carried out by receiving scattered and reflected light which penetrates several millimeters into the surface of the fruit or vegetable (this type will be referred to as a reflection type);

2) devices of a type in which the light from the light source (normally, one lamp) is projected from the side to the fruit or vegetable of the inspected object and in which the light receiving sensor is located at a position where it is opposed to the light source with the fruit or vegetable in between so as to receive the transmitted light (this type will be referred to as an opposite reception type);

3) devices of a type in which the light source (many lamps in many cases) is located on the side of the fruit or vegetable of the inspected object mounted on the shield carrier (or basket), the light is projected from the side, the transmitted light scattered inside the fruit or vegetable and emitted from the bottom is guided from the bottom through a hole bored in the carrier, and the transmitted light is received by the light receiving sensor disposed below the fruit or vegetable in a direction perpendicular to the direction of the projected light (this type will be referred to as a lower reception type).

Among these types, the reflection type devices can be used only for limited kinds of fruits or vegetables suitable for the measurement, because they can obtain only information of the internal quality of the region from the surface of the inspected fruit up to the depth of about several millimeters. In order to extract the information of the internal quality of deep part of the fruits or vegetables, it is necessary to select one of the devices using the transmission methods of 2) and 3) described above.

The devices using the conventional transmission methods described above, however, had the following problems.

In the case of the devices of the opposite reception type, since the measuring light passes through the lateral diameter of the fruits or vegetables, optical path lengths are considerably long. When the inspected object is one resistant to the transmission of light, such as an apple, a peach, or the like, the light having been transmitted and emitted by the inspected object is very weak, thus posing a problem of failing to capture a signal. Particularly, there also arises a problem that the light is more unlikely to pass in the long-wavelength region including the spectral absorption important for the measurement of the internal quality of the fruits or vegetables. The quantity of the transmitted light can possibly be increased by increasing the quantity of the projected light, but it is difficult to increase the quantity of the projected light in the case of the opposite reception type, because the light projection system is normally limited to one lamp because of the structure.

In contrast with it, in the case of the devices of the lower reception type, since the light can be projected from a plurality of directions on the side of the inspected fruit or vegetable, the quantity of the projected light can be increased by employing a multiple lamp method with plural light sources. Since the transmitted light is guided downward, optical path lengths inside the fruit or vegetable can be shorter than in the case of the opposite reception type. Therefore, this type has no problem in terms of the quantity of the transmitted light and effective measurement can also be carried out for fruits or vegetables unsuitable for the opposite reception type.

In the case of the lower reception type, however, in order to guide the detected light out of the bottom, it is necessary to use the bored carriers or to bore holes in the conveyor, which poses a problem that the structure of the conveying system becomes complicated. Since the inspected fruits or vegetables have to be mounted as positioned at the positions of the holes of the conveyor or as positioned on the carriers, there arises a problem that a supply mechanism for mounting the fruits or vegetables has to be provided or that an operator has to place the fruits or vegetables one by one on the occasion of the measurement. In either case the measurement efficiency of the apparatus is lowered and it is a significant problem for the fruit or vegetable internal quality evaluating apparatus that often needs to continuously measure a lot of inspected objects.

A further problem is that assembling of the apparatus and labor of maintenance thereof become complicated, because the light receiving sensor has to be set below the belt conveyor, i.e., within a loop of the belt conveyor.

SUMMARY OF THE INVENTION

In order to solve the above problems, an object of the present invention is to provide a measuring device for measuring an internal quality of an object, the measuring apparatus comprising conveying means for continuously conveying an object, detecting means for detecting a position of the object mounted on the conveying means, light projecting means for projecting measurement light toward the object, light receiving means for receiving light having been transmitted through the object, analyzing means for analyzing the internal quality of the object with the light received by the light receiving means, and reference body interposing means for interposing a reference body having a predetermined optical property in an optical path between the light projecting means and the light receiving means, wherein the analyzing means compares light received with the reference body being interposed, with reference data preliminarily stored, so as to correct a result of the analysis.

The other objects of the present invention will become more apparent by the below description of the embodiments with reference to the accompanying drawings.

BRIEF DESCRIPTION OF THE DRAWINGS

FIG. 4A, FIG. 4B, and FIG. 4C are diagrams to show an artificial fruit or vegetable reference body as the first embodiment of the present invention, wherein FIG. 4A is a perspective view, FIG. 4B is a sectional view, and FIG. 4C is a top plan view;

FIG. 20A, FIG. 20B, and FIG. 20C are diagrams to show the structure around the measurement position of an evaluating device for evaluating the internal quality of the fruit or vegetable in the seventh embodiment of the present invention, wherein FIG. 20A is a side view, FIG. 20B is a top plan view, and FIG. 20C is a side view from a direction perpendicular to FIG. 20A;

FIG. 22A and FIG. 22B are diagrams to show the structure around the measurement position of an evaluating device for evaluating the internal quality of the fruit or vegetable in the eighth embodiment, wherein FIG. 22A is a side view and FIG. 22B is a top plan view;

FIG. 27A and FIG. 27B are diagrams to show the schematic structure of a tray in an evaluating device for evaluating the internal quality of the fruit or vegetable in the tenth embodiment of the present invention, wherein FIG. 27A is a side view sectioned in part and FIG. 27B is a side view from a direction perpendicular to FIG. 27A;

FIG. 28A and FIG. 28B are diagrams to show an artificial fruit or vegetable reference body as the eleventh embodiment of the present invention, wherein FIG. 28A is a perspective view and FIG. 28B is a sectional view;

FIG. 29 is a perspective view to show the structure around the measurement position of a measuring device for measuring the internal quality of the fruit or vegetable in the eleventh embodiment of the present invention;

FIG. 32A and FIG. 32B are diagrams to show an artificial fruit object as the twelfth embodiment of the present invention, wherein FIG. 32A is a perspective view and FIG. 32B is a sectional view;

DETAILED DESCRIPTION OF THE PREFERRED EMBODIMENTS

The first embodiment of the present invention will be described based on FIG. 1 to FIG. 3.

Figure 1:
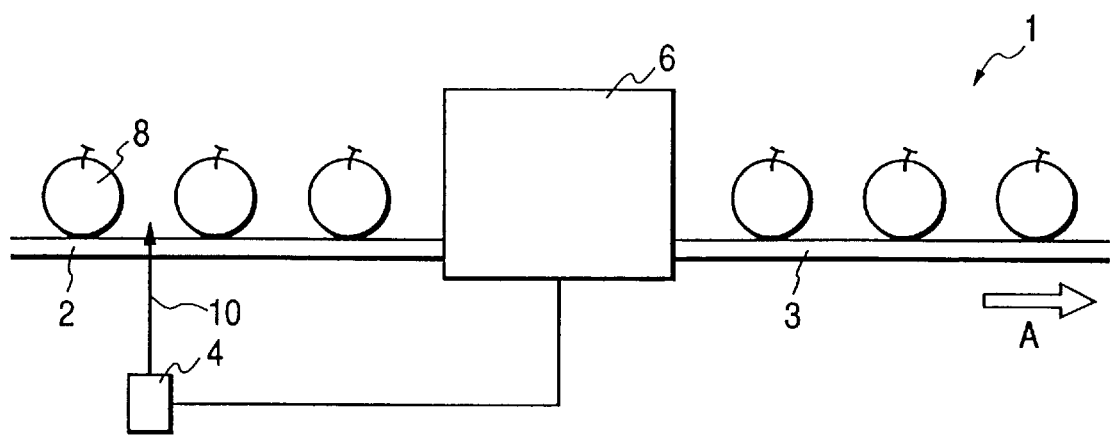
FIG. 1 is a schematic diagram to show the overall structure of the first embodiment according to the present invention.

As illustrated in FIG. 1, the device 1 of the present embodiment is composed of a belt conveyor 2, a sensor 4, a measuring section 6, and so on.

On the belt conveyor 2 there are inspected objects 8 such as oranges or the like arranged in the longitudinal direction A of the belt 3 and the inspected objects 8 are moved in the longitudinal direction A. The sensor 4 and measuring section 6 are disposed in the middle of the moving direction A of the belt 3. The sensor 4 is a photoelectric sensor, which is arranged to project infrared light 10 onto the belt conveyor 2 and measure the reflected light therefrom whereby the sensor 4 can obtain information about presence/absence, spacing, and position of the inspected object 8 on the belt conveyor 2. The measuring section 6 is located downstream of the sensor 4 in the moving direction of the belt conveyor 2 and is arranged to project light toward the inspected object and measure the internal quality of the inspected object from light outgoing from the inspected object.

Figure 2:
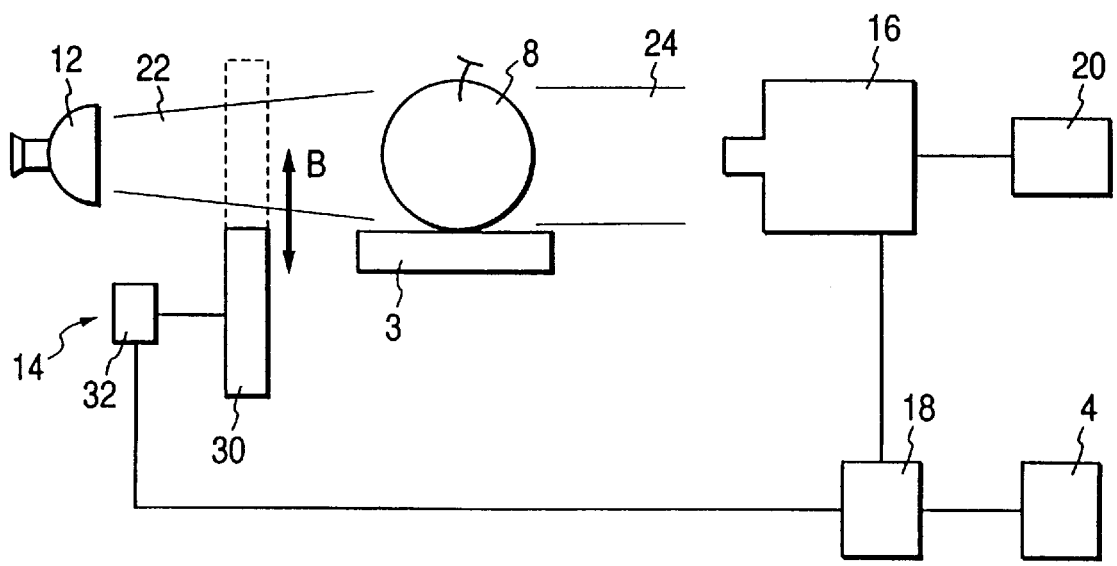
FIG. 2 is a schematic diagram to show the structure of a measuring section of the first embodiment according to the present invention.
Figure 3:
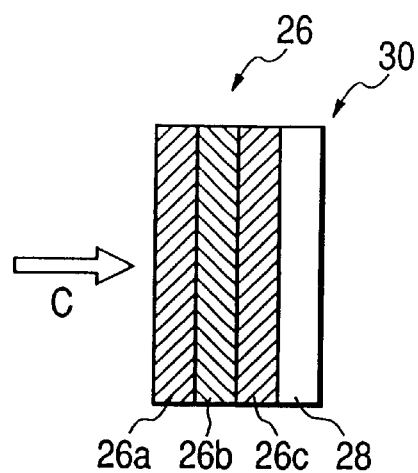
FIG. 3 is an enlarged view to show the structure of a filter portion of the first embodiment according to the present invention.

The measuring section 6, as illustrated in FIG. 2, is composed of a lamp 12, a filter portion 14, a spectroscope 16, a control section 18, an arithmetic operation section 20, and so on.

The lamp 12 is placed so as to be capable of projecting the light from the side to almost the whole of the inspected object 8. The light 22 projected from the lamp 12 toward the inspected object 8 is one having wavelengths, for example, in the near-infrared region (650 to 950 nm). After this light is absorbed in part inside the inspected object 8 receiving the projected light, transmitted light 24 is emitted from the inspected object 8.

The filter portion 14 is located between the lamp 12 and the inspected object 8. The filter portion 14 is composed of a filter 30 consisting of ND filters 26 and a diffused plate 28, as illustrated in FIG. 3, and a calibration driving mechanism 32. The calibration driving mechanism 32 is one using a solenoid and is capable of moving the filter 30 in the vertical directions B according to presence/absence of the inspected object 8 in the measuring section 6.

The filter 30 is, for example, a stack of three ND filters 26a, 26b, 26c and a diffused plate 28 and planes thereof are perpendicular to the irradiation direction C of the light 22 from the lamp 12 toward the inspected object 8. The ND filters 26 are filters of neutral densities (achromatic colors) which uniformly absorb the incident light 22 at all the wavelengths and which have the function to reduce the quantity of transmitted light without changing the wavelength components of the incident light; in the present embodiment, three types of ND filters 26a, 26b, 26c having the respective transmittances of 0.1%, 5%, and 20% are stacked in order from the lamp 12 side to the inspected object 8 side. The diffused plate 28 is stacked on the inspected object 8 side of the ND filter 26c with the transmittance of 20% disposed closest to the inspected object 8 among the three ND filters 26a, 26b, 26c. The diffused plate 28 can diffusely reflect or diffusely transmit the incident light from the ND filters 26 and emit light in uniform light quantity throughout the entire surface thereof. The light from the light source can be attenuated at a predetermined rate by employing this structure for the filter 30, and the base line of the device 1 can be corrected by measuring the light quantity of the attenuated light.

The spectroscope 16 is disposed on an extension line of the optical path of the light from the lamp 12 to the inspected object 8 and receives light from the inspected object 8 or the filter 30. The spectroscope 16 is arranged so as to be capable of measuring an absorption spectrum of the output light 24 from the inspected object 8 and thereby measuring the internal quality of the sugariness or the like of the inspected object 8, based on the absorption spectrum.

The sensor 4 described above is connected to the control section 18 and the control section 18 is arranged to be capable of converting the light quantity of the incident light to the photoelectric sensor 4 to current by photoelectric conversion and determining whether the inspected object 8 is absent or present in the measuring section 6 by determining whether the current is larger than a predetermined value, thereby detecting the spacing between inspected objects 8 on the conveyor 3.

Further, the control section 18 is connected to the calibration driving mechanism 32 and outputs a signal for driving it, to control the driving of the filter 30.

The calibration driving mechanism 32 drives the filter 30 so as to place it in the middle of the optical path from the lamp 12 to the inspected object 8 when the photoelectric sensor 4 detects that the spacing between the inspected objects 8 is larger than the predetermined value and then a portion corresponding to the spacing between the inspected objects 8 goes into the measuring section 6. Then the calibration of the device 1 is carried out in this placement state of the filter 30. In the other cases than above, i.e., during periods in which the spacing between the inspected objects 8 is less than the predetermined value, the calibration driving mechanism 32 drives the filter 30 so as to retract it from the optical path from the lamp 12 to the inspected object 8. In this way, the calibration of the device 1 can be carried out on arbitrary occasions, not only at the start of the measurement but also during the measurement, with the light traveling through the filter 30, so that the internal quality of the fruits or vegetables can be measured more accurately without being affected by the variations of the base line due to the measurement. The above predetermined value is a value determined according to the kind of the inspected objects 8, the size thereof, the measuring speed, etc., which is set by a user of the device before the start of the measurement or during the measurement.

The arithmetic operation section 20 is connected to the spectroscope 16 and receives an input of the current from the frequency spectrum based on the transmitted light 24 from the inspected object 8 or current in the calibration. The arithmetic operation section 20 can measure the internal quality of the inspected object 8 without influence of the variations of the base line, the noise of the spectroscope 16, etc., based on these current values.

With the device in the above structure, when the measurement is carried out for the inspected objects 8 arranged in the longitudinal direction A of the belt 3 on the belt conveyor 2, the spacing between the inspected objects 8 can be detected and the calibration of the device 1 can be performed when this spacing is not less than the predetermined value. Therefore, the calibration can be carried out on desired occasions at a place where the inspected object 8 is absent, not only before the start of the measurement but also even after the start of the measurement, so that the measurement does not have to be suspended because of the calibration. Therefore, the internal quality of the fruits or vegetables can be measured accurately by carrying out the calibration of the device 1 for each of the inspected objects 8 without interruption of the measurement.

Described below is the step of the measurement to measure the internal quality of the fruits or vegetables according to the present embodiment.

First, the calibration of the device 1 and the measurement of dark current are carried out prior to the start of the measurement. The calibration is carried out in such a manner that, in a state in which the inspected object 8 is absent in the measuring section 6, the calibration driving mechanism 32 is actuated to position the filter 30 in front of the lamp 12 and the spectroscope 16 measures the quantity of the light traveling from the lamp 12 through the filter 30 to the spectroscope 16. The quantity of this light is converted to a current value by the spectroscope 16 and this is used as a base line (or a reference value) of the measurement of the inspected objects 8. On the other hand, the measurement of dark current is carried out in a state in which the external light is completely shut out from the spectroscope 16. This can be effected by intercepting the light travelling to the spectroscope 16 with the lamp 12 being in an on state or by keeping the lamp 12 in an off state. The dark current is the current that the device 1 itself has in a state in which no light is incident to the spectroscope 16. When a dark current value is subtracted from a measurement (a current value after photoelectric conversion) thereafter by the spectroscope 16, a current value from which the influence of the noise of the device etc. is removed can be derived.

The measurement of the internal quality of the inspected object 8 is carried out when each of the inspected objects 8 placed along the longitudinal direction of the belt 3 on the belt conveyor 2 reaches the measuring section 6 with movement of the belt 3. Namely, when an inspected object 8 reaches the measuring section 6, the inspected object 8 is irradiated directly with the light from the lamp 12 and emergent light, after absorbed in part inside the inspected object 8, is incident to the spectroscope 16. The internal quality of the inspected object 8 can be measured based on a frequency spectrum of this light. This is based on the fact that the profile of the frequency spectrum differs depending upon components contained in the inspected object 8, because there exist frequencies at which the quantity of light is high because of the components.

The base line varies with continuation of the measurement. This is caused by the environmental change of the temperature or the like of the spectroscope 16, the measuring section 6, or the region around them. The base line has to be kept always constant in order to obtain accurate measured values. In the present embodiment the base line is measured at a position where the spacing between the inspected objects 8 is not less than the predetermined value. This value is stored in the arithmetic operation section 20 connected to the spectroscope 16.

After completion of the calibration and the measurement of the dark current at the start of the measurement, the filter 30 is retracted from the optical path from the lamp 12 to the spectroscope 16, so that the light from the lamp 12 becomes directly incident to the spectroscope 16. When an inspected object 8 moving on the belt reaches the measuring section 6 in this state, the near-infrared light emitted from the lamp 12 is projected directly onto the inspected object 8. The light is absorbed in part by the inspected object 8 and is then emergent from the inspected object 8 to enter the spectroscope 16. Then the spectroscope 16 measures the internal quality of this inspected object 8.

The internal quality of the inspected objects is measured successively every time the inspected object 8 reaches the measuring section 6 in this way. When during this measurement the photoelectric sensor 4 detects that the spacing between the inspected objects 8 is not less than the predetermined value, the control section 18 determines that the inspected object 8 is absent in the measuring section 6 and outputs a signal for driving the filter to the calibration driving mechanism 32. In response to this signal, the solenoid of the calibration driving mechanism 32 is actuated to move and position the filter in the optical path from the lamp 12 to the spectroscope 16.

The filter 30 is, for example, a stack of three ND filters and a diffused plate and the ND filters 26 are a stack of three types of ND filters 26a, 26b, 26c having the respective transmittances of 0.1%, 5%, and 20%, arranged in this order from the lamp side to the inspected object 8 side. The light incident to this filter 30 is attenuated by the three ND filters 26a, 26b, 26c to about 0.001% of the light quantity thereof. On the other hand, the diffused plate 28 is stacked on the inspected object 8 side of the ND filter 26c with the transmittance of 20% and the light incident to this diffused plate 28 is emitted in a diffused manner. The light from the light source can be attenuated at the predetermined rate by employing this structure for the filter 30. The quantity of this attenuated light is adjusted so as to be within a predetermined range against the quantity of the transmitted light by the inspected object 8 such as the orange or the like. Namely, the ND filters 26 and diffused plate 28 used herein are changed depending upon the kind, the size, the lot, etc. of the inspected objects 8.

The base line of the device 1 can be measured by measuring the quantity of the attenuated light by this filter. Fluctuations of the base line can be followed up as occasion may demand. The measured value of the base line is stored in the arithmetic operation section 20.

Here, the transmittance discussed below is used for the evaluation of the internal quality of the inspected objects 8. Specifically, the transmittance T of each inspected object 8 (the i-th object out of the total n) is expressed by the following equation:

$$Ti=(Si-D)/(R-D) \qquad (1)$$

where Si is a measured value of the frequency spectrum of the output light absorbed in part within the inspected object 8, R is an average of current values according to the calibration, and D is a dark current value. Namely, the transmittance of the inspected object 8 is defined by a ratio of the output light from the inspected object 8 to the output light from the lamp 12 through the filter 30. In each of the numerator and the denominator, the dark current value D is subtracted from the measured value Si of the frequency spectrum obtained from the output light or from the average R of current values obtained by the calibration. This eliminates the noise specific to the spectroscope 16.

Modifications of the present embodiment will be described below.

In the present embodiment the filter 30 was composed of the three ND filters 26a, 26b, 26c and diffused plate 28, but the number of ND filters may be one, two, or more than three.

The transmittances of light of the respective ND filters may also be values different from those of the present embodiment.

The ND filters can be replaced by filters of another type whose transmittances of light are known.

The filter 30 can also be constructed of only a diffused plate.

The calibration driving mechanism 32 was arranged to move the filter 30 in the vertical directions B so as to position the filter 30 in the middle of the optical path from the lamp 12 to the inspected object 8, but the moving directions of the filter 30 can be arbitrary directions, e.g. horizontal directions.

The detection of the inspected object 8 was determined based on incidence of the light to the photoelectric sensor 4 provided separately, but it may also be judged based on the quantity of the incident light to the spectroscope 16.

Whether the inspected object 8 is present or absent may also be judged by using a weight sensor provided on the belt 3.

The projection of the light from the lamp 12 to the inspected object 8 does not always have to be made from the side but can also be made from the top or the like, as long as the light can be projected to almost the whole of the inspected object 8.

The light emitted from the photoelectric sensor 4 may also be light of other wavelengths than the infrared light.

The light emitted from the lamp 12 may also be light of the other wavelengths than the near-infrared light.

The lamp 12 may be an optical fiber and the number of lamps may also be one, two, or more than two.

Figure 4A:
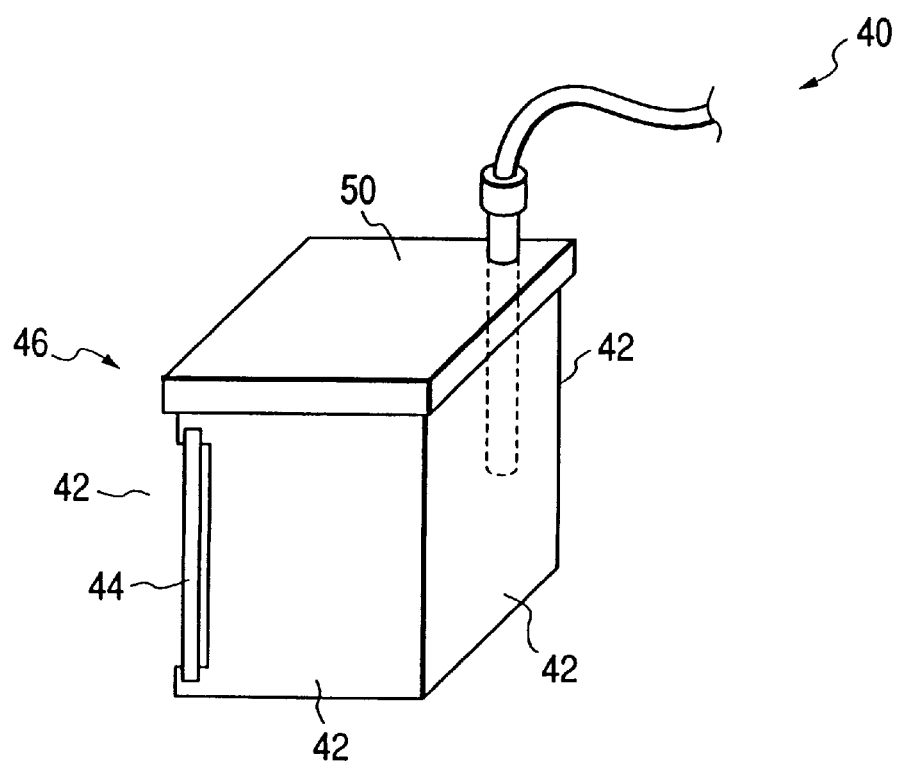
Figure 4B:
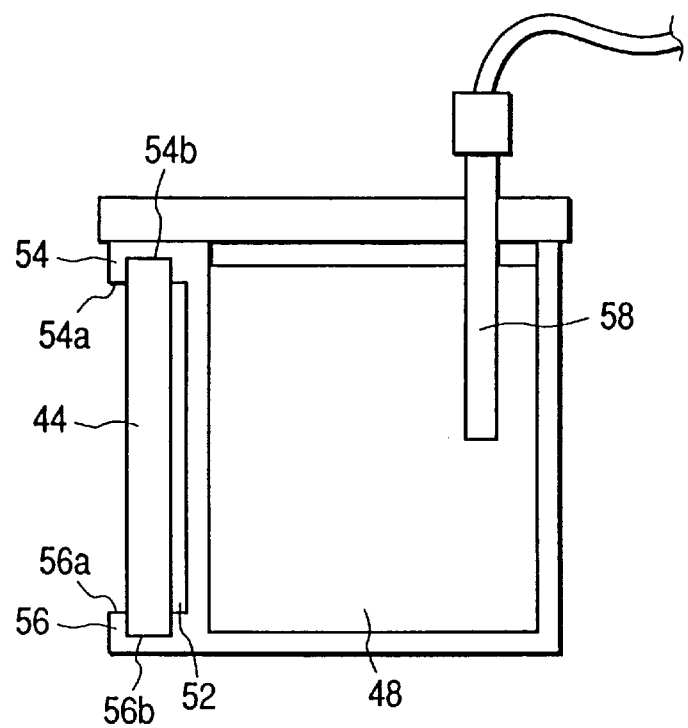
Figure 4C:
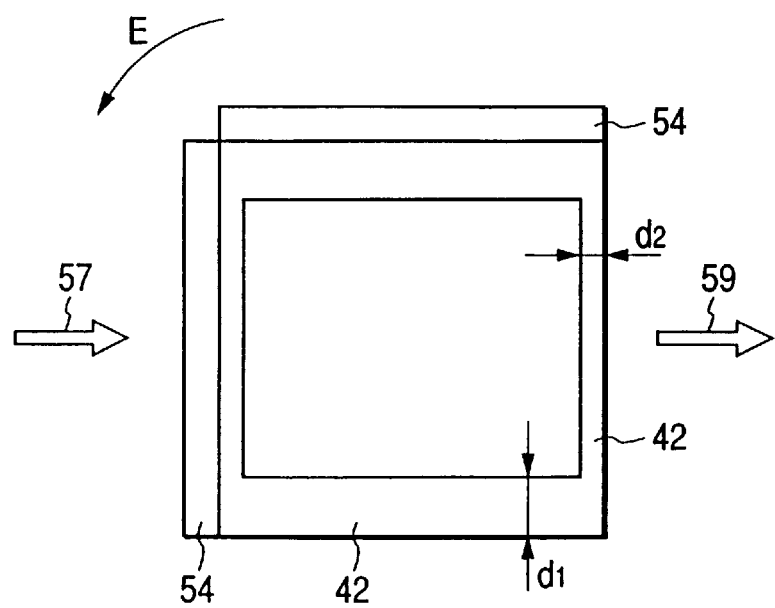

The second calibration method in the present embodiment will be described next with reference to FIGS. 4A, 4B, and 4C. FIGS. 4A, 4B, and 4C are diagrams to show an artificial fruit or vegetable reference body (artificial fruit object) 40 as the pseudo-object member, in which FIG. 4A is a perspective view, FIG. 4B a sectional view, and FIG. 4C a top plan view. This artificial fruit or vegetable reference body 40 is of a rectangular parallelepiped having the height of 80 mm and the bottom 65 mm square, and it is comprised of a resin vessel 46 having a glass plate 44 in each of two side faces out of its side faces 42, and a light transmitting body (optically transparent material) 48 retained therein. The top surface of the vessel is covered by a plastic lid 50 of the same material as the resin vessel 46 to be closed hermetically.

The resin vessel 46 and lid 50 are made of the material obtained by mixing graphite as a filler in polyethylene (PE) and have such a property as to transmit light. As illustrated in FIG. 4C, the side faces 42 of the vessel 46 have two types of thicknesses d1, d2, the thicknesses of the adjacent surfaces being different from each other and the thicknesses of the opposed surfaces being identical. In the two adjacent surfaces out of the side surfaces 42 of the resin vessel 46, the heat-resistant glass plates 44 are disposed in parallel to the side faces 42. These two glass plates 44 are of the same shape and are placed through an air layer 52 of an approximately uniform thickness with respect to the side surfaces 42 of the resin vessel 46 without contact therewith. At each of the upper edge and the lower edge of each side surface 42 of the resin vessel 46, a first flange portion 54 and a second flange portion 56 are provided along the ridge line thereof and recesses 54b, 56b are formed throughout the entire length in lower surface 54a of the first flange portion and in upper surface 56a of the second flange portion. Each glass plate 44 is slid in the horizontal direction to be set in the both recesses 54b, 56b, whereby the glass plate 44 is placed in the side surface 42 of the resin vessel 46.

The light transmitting body 48 is properly selected from an aqueous solution of an acid and an aqueous solution of a sugar, depending upon the kind of the fruits of vegetables being the inspected objects. For example, the aqueous solution of the acid is an aqueous solution of 1% citric acid.

The artificial fruit object 40 is equipped with a temperature measuring member (temperature measuring means) 58 using a thermistor or the like for measuring the temperature of the light transmitting body 48, inside the light transmitting body 48.

Figure 5:
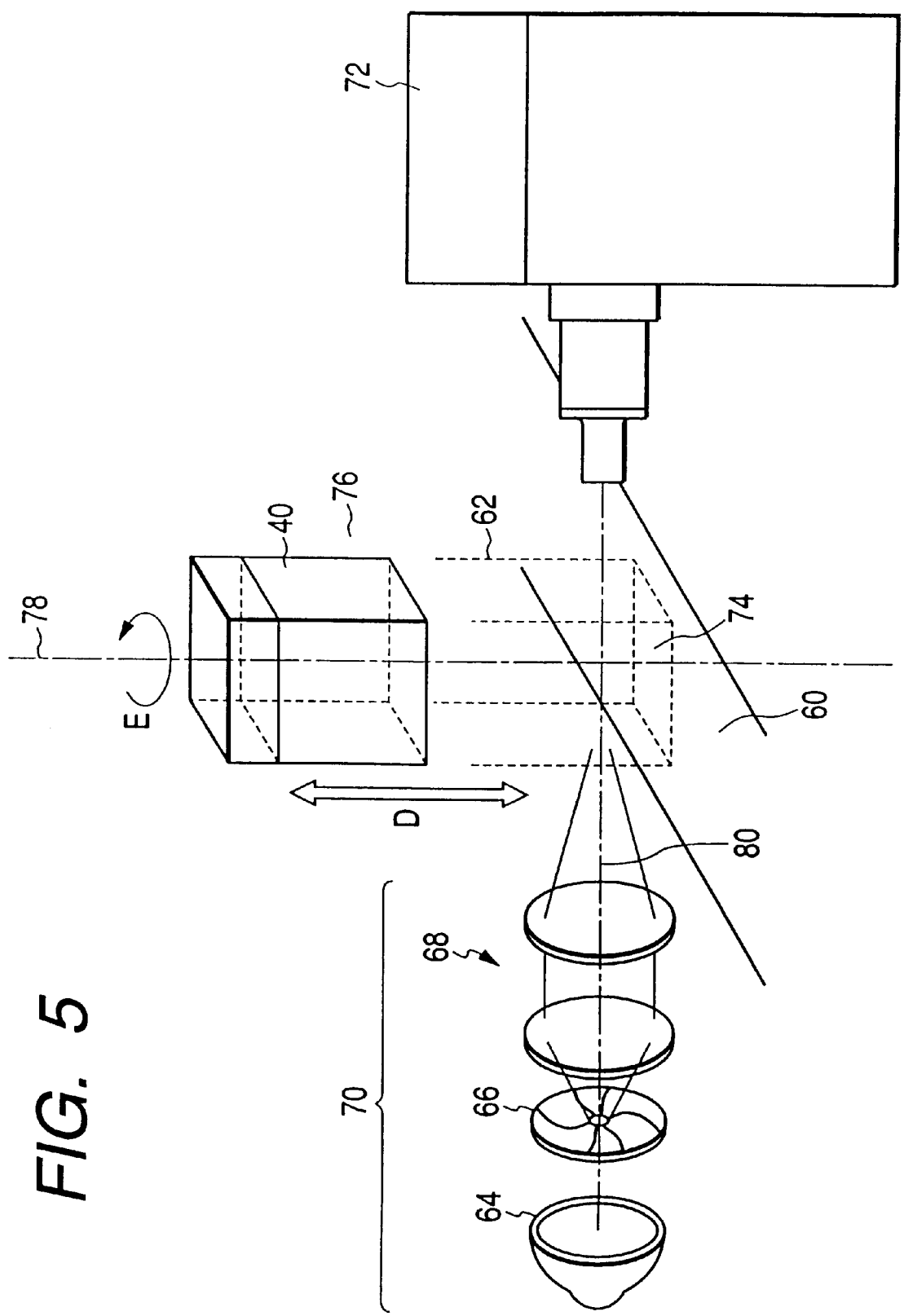
FIG. 5 is a diagram to show the structure near the measurement position of the measuring device for measuring the internal quality of the fruit or vegetable in the first embodiment of the present invention.

Described next is a method for correcting the measured value of the measuring device for measuring the internal quality of the fruit or vegetable using the artificial fruit object 40. FIG. 5 is a diagram to show the structure around the measurement position 62 of the fruit or vegetable measuring device. The measuring device has the belt conveyor 60 and the fruits or vegetables to be inspected (for example, oranges) placed on the belt conveyor 60 are successively fed to the measurement position 62. At the measurement position 62 the light is projected to the inspected object from light projecting device 70 composed of a light source 64, a stop 66, and a lens system 68. The light having passed through the inspected object is incident to a light receiving sensor 72. The light incident to the light receiving sensor 72 is separated into a plurality of wavelength band channels and spectral analysis thereof is carried out by a known method for checking the absorbance in each of the channels, thereby calculating the internal quality of the inspected fruit or vegetable, for example, the acidity thereof. Since this method itself is known, the description thereof is omitted herein.

The device is provided with the artificial fruit object 40 and the artificial fruit object 40 is arranged to be moved up and down in the directions of arrows D in FIG. 5 at the measurement position 62 by an unrepresented mechanism so as to move between a calibration position 74 located between the light projecting system and the light receiving sensor 72 and a normal position 76 where the artificial fruit object 40 is retracted from the calibration position 74. The artificial fruit object 40 is rotatable about a vertical axis 78 passing through the center of the bottom of the artificial fruit object 40 and one of the side faces 42 each provided with the glass plate 44 is positioned so as to be approximately perpendicular to the optical axis 80 of light 57 projected from the light projecting device 70 and output light 59 from the artificial fruit or vegetable reference body.

Figure 6:
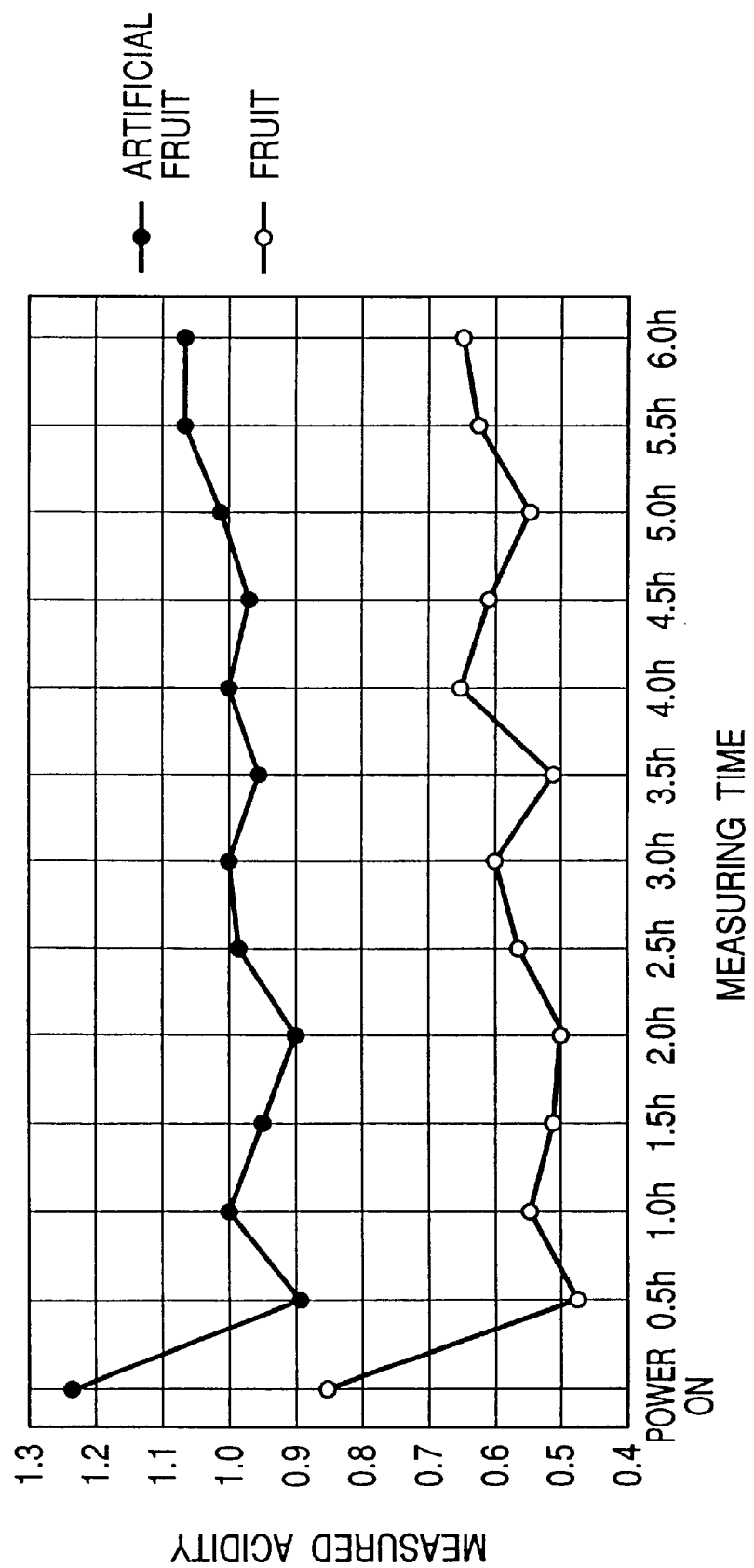
FIG. 6 is a diagram to show time changes of measured acidity of an artificial fruit and an actual fruit in the first embodiment.

FIG. 6 shows the result of the measurement where the acidities of the artificial fruit object 40 of the present embodiment and a fruit were measured with a lapse of time. As apparent from this figure, the acidities of the artificial fruit object 40 (values calculated from absorbances) measured under the same environment as in the measurement of acidities of the fruit vary with time approximately in synchronism with those of the fruit, and it is thus seen that there is a certain correspondence relation between them.

Spectral absorption of the fruits or vegetables in the near-infrared region originates in the functional groups such as O—H, C—H, and so on, and thus the measurement of the internal quality such as the acidity or the like of the fruits or vegetables by spectral analysis is carried out based on the absorption spectra due to these functional groups. The absorption properties vary depending upon the environmental change of the temperature, the humidity, or the like. In the artificial fruit object 40 of the present embodiment, the transmitting body is made of the base of the aqueous solution of the acid (citric acid). Therefore, the artificial fruit object 40 contains the same functional groups as the fruits or vegetables and, therefore, the absorption property of the artificial fruit object 40 also varies in synchronism with the fruits being the real inspected objects. This permits correction for the variations of spectral absorption due to the environmental change.

An example of the correction method for the measurement of the internal quality of the fruit or vegetable using this reference body will be described below with an example of measurement of acidity.

Figure 7:
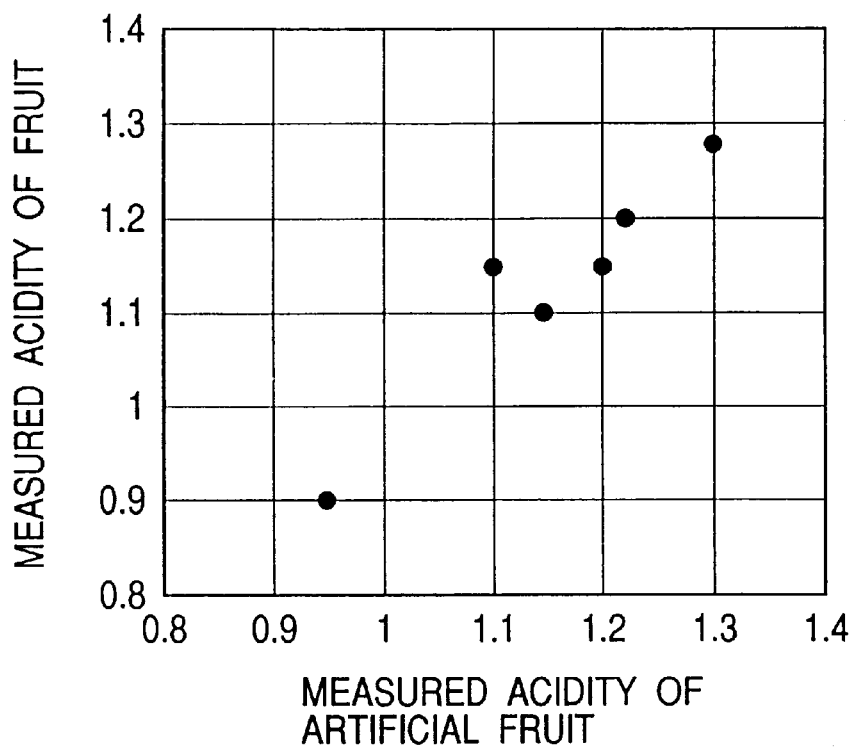
FIG. 7 is a diagram to show synchronism of changes of measured acidity against environmental change of an artificial fruit object and a real orange in the first embodiment.

First obtained preliminarily is a relation of variations in measured acidity values due to the environmental change between the artificial fruit or vegetable reference body 40 and the real fruits (which is a slope S of a straight line approximately connecting six points in FIG. 7). Obtained as a reference acidity value on the other hand is a measured acidity DR of the artificial fruit object in a state in which the acidities of the real fruits can be measured (calculated) without an error (i.e., in a state (circumstance) in which correct measured values can be obtained). In other words, the reference acidity value DR is a value that is so defined that when an acidity obtained in the measurement of acidity of the artificial fruit object in a certain environmental state is DR, measured acidities of the real fruits obtained in that state can be correct acidity values without correction (or with the correction value of zero). The "correct acidity values" herein mean values of acid concentrations of the real fruits obtained not by spectral analysis but by chemical analysis.

Therefore, the value of DR is obtained using a real fruit having a known acidity measured by chemical analysis.

The above relation of variations (the slope S of the straight line) and the reference acidity value DR are preliminarily obtained and stored as data in a processing system of the measuring device.

The correction operation in the actual measurement is carried out every predetermined time, for example, every two hours. In the correction operation the artificial fruit object 40 of FIG. 5 is first moved down to the calibration position between the light projecting system and the light receiving sensor 72 and the same measurement as with ordinary real fruits is carried out with the artificial fruit object 40 to calculate the acidity thereof. Supposing the actually measured acidity is D, a correction value C is calculated according to the following equation.

$$C=(DR-D)\times S$$

A measured value is corrected by adding the correction value obtained in this way to a measured value of each fruit being an actually inspected object, so that the measured value becomes closer to a correct acidity value without being affected by the environmental conditions.

For example, let us suppose that the value of DR was 1.0% and the slope S of the straight line approximately connecting the points in FIG. 7 was preliminarily obtained as 0.9. Further, suppose the acidity of the artificial fruit object measured in the correction operation was 1.2%. In this case positive errors appear with the environmental change (i.e., measured values are higher than actual values). In this case the correction value C is calculated as follows.

$$C=(1.0-1.2)\times 0.9=-0.18$$

Correction is made by adding this correction value "−0.18" to a measured value obtained for each fruit to be inspected (i.e., by subtracting 0.18 from the measured value).

Since the environmental conditions vary with time, the correction operation is carried out at intervals of the predetermined time during the measurement period, as described above. For example, when the correction operation is carried out every two hours, an application range of a correction value can be selected conceivably from 1) a range in which the correction value obtained is applied to measurement data for past two hours, 2) a range in which the correction value obtained is applied to measurement data for next two hours, 3) a range in which the correction value obtained is applied to measurement data obtained for one hour each before and after the correction operation, and so on. The way of 3) is most preferable in terms of effectiveness of the correction, but selection of the range does not always have to be limited to this. As the intervals of the correction operation become shorter and shorter, the follow-up property after the environmental change becomes better, so as to enhance the correction accuracy. However, the throughput of the measurement is lowered because the intended measurement is suspended during the measurement of the artificial fruit object for correction. Therefore, the intervals are set to those of an appropriate time, taking them into consideration. It can also be contemplated that the correction operation is carried out at intervals of a shorter time for a while after on of the light source, because stability of the light source 64 is low, and then the intervals are lengthened after the light source is stabilized.

The artificial fruit or vegetable reference body 40 of the present embodiment is provided with the temperature measuring member 58 for measuring the temperature of the light transmitting body 48, inside the light transmitting body 48. This is for correction for the temperature difference between the artificial fruit object 40 and the fruits as actually inspected bodies. Namely, the artificial fruit object 40 is mounted on the device in many cases as in the example of the device illustrated in FIG. 5, whereas the fruits or vegetables such as oranges, which are objects to be measured, are supplied from predetermined storage. There arise no issues as long as they are in a common environment. It is, however, preferable to effect temperature correction when there is the temperature difference between them. Thus, the artificial fruit object 40 of the present embodiment has the temperature measuring member 58 to monitor the temperature of the transmitting body and correction is further made with consideration to the temperature condition, based on the result of the monitoring, on the occasion of obtaining the above correction value.

In the present embodiment the resin vessel 46 forming the artificial fruit object 40 can transmit the light and the transmission amounts differ depending upon the thicknesses thereof. In the artificial fruit object 40 constructed as described above, the amounts of light emitted from the opposite vessel surface 42 when the light is projected almost normally to the vessel side surface 42, differ depending upon the thicknesses of the side surfaces 42. Namely, when light in the same quantity is projected to two side surfaces having different thicknesses, the amount of light transmitted by the thicker side surface is smaller than the amount of light transmitted by the thinner side surface; therefore, the thicker side surface has a lower transmittance of light. The present embodiment makes use of this property and is arranged to rotate the artificial fruit object 40 according to a change in the kind or lot of inspected objects or a change of circumstances or the like, thereby changing the irradiated surface over between the surfaces having the different transmittances.

As described above, the present invention permits the artificial fruit object 40 to be selected according to the change of the inspected object without changing the light projecting system and light receiving system.

Since the heat-resistant glass plates 44 are provided in the side surfaces 42 exposed to the light projected to the artificial fruit or vegetable reference body 40 out of the side surfaces 42 of the resin vessel 46, the artificial fruit or vegetable reference body 40 has higher durability against heat due to the projected light than in the case without the glass plates 44.

Further, since the air layer is present between the glass plates 44 and the side surfaces 42, it facilitates radiation of heat even when the artificial fruit or vegetable reference body 40 is heated by the projected light, which further enhances the durability.

Since each glass plate 44 can be detached by sliding it in the horizontal direction, the glass plate 44 can be replaced with another when the heat-resistant property of the glass plate 44 is degraded. This can always assure the sufficient heat-resistant property.

It should be noted that the present embodiment is just an example and the present invention is by no means intended to be limited to this.

Specifically, the vessel of the artificial fruit object 40 may also be made of polyfluoroethylene (PFE), or glass like the glass plates 44, instead of polyethylene (PE).

The glass plates 44 provided in the side surfaces 42 of the resin vessel 46 may be replaced by heat-resistant ND filters.

In the present embodiment the glass plates 44 are provided in the two side surfaces out of the four side surfaces 42 of the resin vessel 46, but the number of surfaces equipped with the glass plate 44 may also be one, three, or four (all).

The opposed side surfaces 42 of the resin vessel 46 have the common thickness, but the combination of the thicknesses of the four side surfaces 42 can be determined arbitrarily.

The air layer 52 between the side surfaces 42 and the glass plates 44 of the resin vessel 46 can be formed in an arbitrary thickness or can be excluded.

The shape of the artificial fruit or vegetable reference body 40 does not always have to be the rectangular parallelepiped having the square bottom, but may also be a polygonal prism or a circular cylinder.

The light transmitting body 48 may be of a gel substance, for example, one obtained by mixing cerium oxide of the diameter of about 0.3 $\mu$m as a light scattering body in 1% citric acid aqueous solution to disperse it uniformly and making it gel with polyacrylamide gel.

In the present embodiment the artificial fruit object 40 was arranged to be moved up and down at the measurement position 62, but another conceivable configuration is such that the artificial fruit object 40 is fixed above or below the measurement position 62 and on the occasion of calibration the light projecting device 70 and light receiving sensor 72 are moved up or down together.

The rotation of the artificial fruit object 40 can also be counterclockwise.

The artificial fruit object 40 may also be arranged to rotate about a horizontal axis passing the center of the side surfaces 42 while being approximately normal to the optical axis of the projected light from the light projecting device 70, instead of the vertical axis 78 passing the center of the bottom. In this case it is desirable to make the thicknesses of the side surface and the top surface or the bottom surface different from each other and provide each surface with a heat-resistant glass plate according to the above-stated method.

The axis of rotation of the artificial fruit object 40 does not always have to pass through the center of the bottom of the vessel 46 as long as it is an axis extending along the vertical direction.

On the other hand, the present invention permits the internal quality of the inspected objects to be measured under the same conditions, irrespective of the sizes of the inspected objects. The details will be described below.

Figure 8:
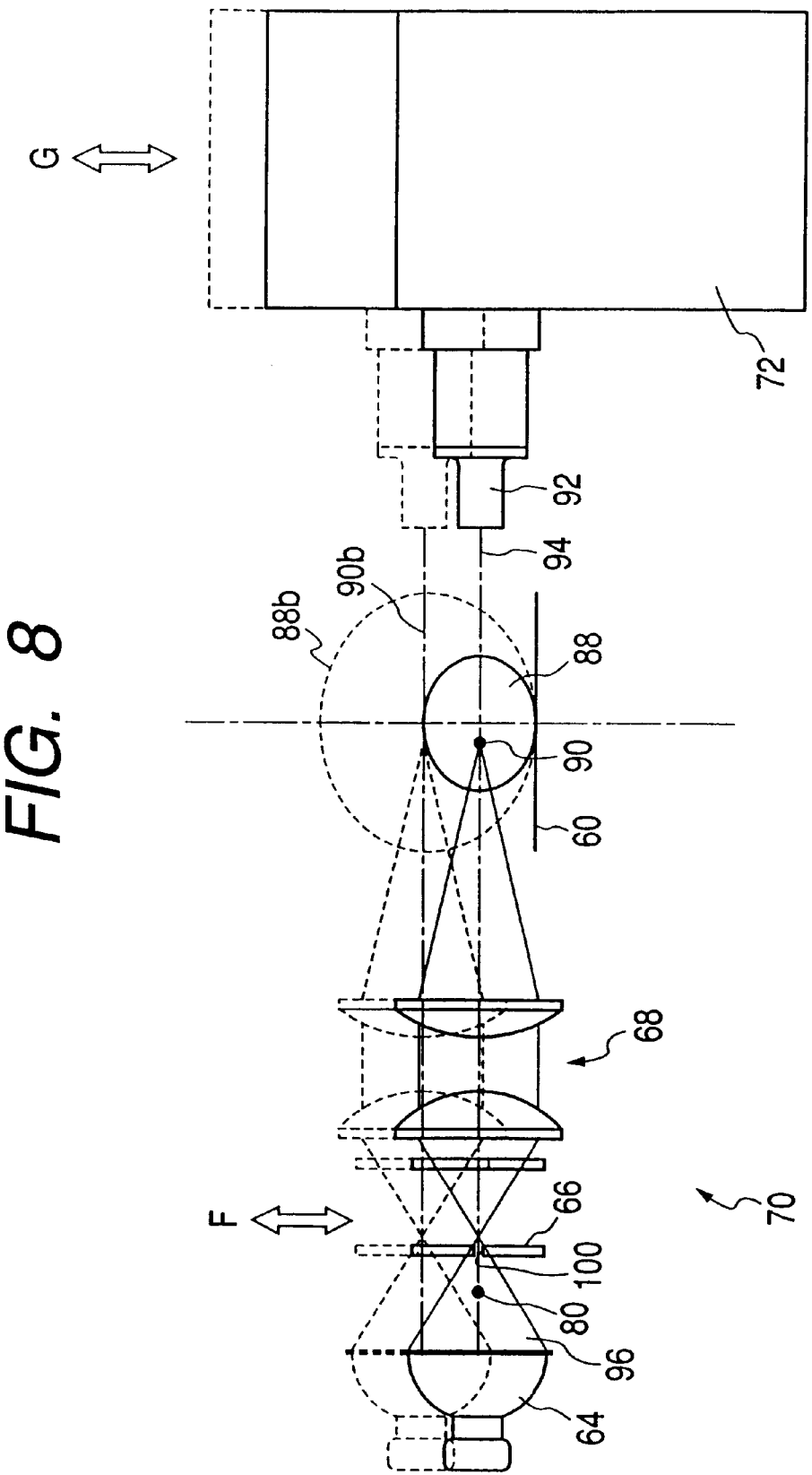
FIG. 8 is a schematic structural diagram of the first embodiment of the present invention.

FIG. 8 is a schematic structural diagram of a device according to the present embodiment. The components described above will be omitted from the description. Each of projection optical system 70 and spectroscope 72 can be moved up and down in the vertical directions indicated by arrows F and G, by a linear motor (not illustrated). During the measurement of an inspected object 88, the optical axis 80 of the projection optical system 70 is made coincident with the optical axis 94 of receiving lens 92 of the spectroscope 72 and they are moved up and down so as to locate the equator part 90 of the inspected object 88 on these optical axes.

The projection optical system 70 is composed of a lamp 64, a stop 66, and a lens 68. The lamp 64 projects light 96 toward the inspected object 88 and the light 96 is projected to the inspected object 88 through the stop 66 and lens 68 disposed normally to the optical axis 80 of the projection optical system between the lamp 64 and the belt conveyor 60. The stop 66 is constructed in such structure that the size of aperture 100 is continuously variable in a concentric circle shape by stop wings. The light 96 emitted from the lamp 64 passes through the aperture 100 opening in a predetermined size according to the kind of the inspected object 88 and is properly condensed by the lens 68 to irradiate the inspected object 88 around the equator part 90. The projection optical system 70 is arranged to be capable of being moved up and down all together. This structure permits the height of the whole apparatus to be changed according to the size of the inspected object 88 and the equator part 90 of the inspected object 88 is always on an extension line of the optical axis 94 of the receiving lens 92 of the spectroscope 72, irrespective of the size of the inspected object 88. Therefore, the light 96 can always be projected toward the equator part 90 of the inspected object 88.

For example, when a large inspected object 88b is measured, the projection optical system 70 and spectroscope 72 are moved up as indicated by the dashed lines. In this way, the light is always projected to the region around the equator part 90b of the inspected object 88b, irrespective of the size of the inspected object, so that the spectroscope can receive the light emerging from the region around the equator part 90b.

Therefore, the internal quality of each inspected object can be measured under the same conditions.

Figure 9:
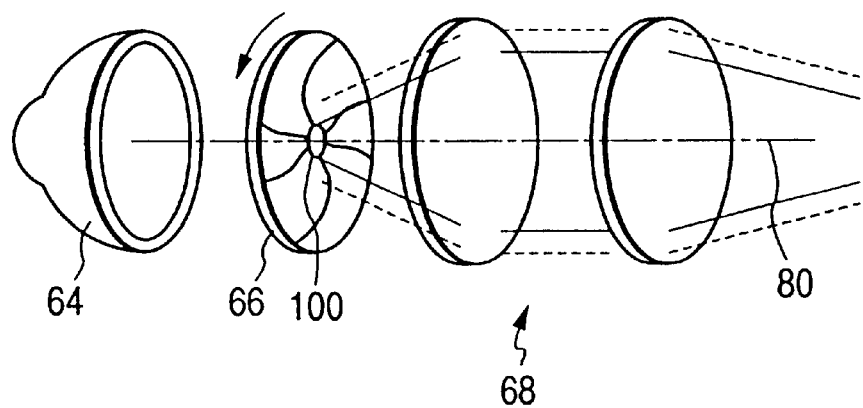
FIG. 9 is a perspective view to show the schematic structure of a projection optical system in the first embodiment of the present invention.

The stop 66 of the projection optical system 70 will be described next. FIG. 9 is a perspective view to show the structure of the projection optical system 70.

In the present embodiment the stop 66 has the aperture 100 which is arranged to be continuously variable in the concentric circle shape. When the light is projected in a constant projection amount from the lamp 64 disposed behind the stop 66, the light is emitted in an amount proportional to the aperture diameter of the aperture 100 from the aperture 100 in the front surface of the stop 66.

The aperture diameter of the aperture 100 is set based on the kind of the fruit or vegetable being the inspected object 88. For measuring the internal quality of the fruit or vegetable that is apt to transmit the light relatively easily, the aperture diameter of the aperture 100 is set to be so small as to reduce the projection amount to the inspected object 88. On the other hand, in the case of the fruit or vegetable that is resistant to transmission of the light, the aperture diameter of the aperture 100 is set to be so large as to increase the projection amount to the inspected object 88. When the aperture diameter is set according to the kind of the inspected object 88 so as to change the amount of the light projected onto the inspected object 88 as described above, the amount of light emitted from the inspected object 88 can be controlled so as to be not less than a fixed value, irrespective of the kind of the inspected object 88, whereby the internal quality of the fruit or vegetable can be measured more accurately independent of the kind of the inspected object 88.

Examples of the measurement in the present embodiment will be described below. The description of the calibration described above will be omitted herein.

A first example is the measurement of the internal quality of an orange which is apt to transmit the light easily. The aperture 100 of the stop 66 is set to the minimum diameter. In this case, the projection amount to the inspected object 88 is small but the amount of light emitted from the inspected object 88 is sufficiently large. The internal quality of the inspected object 88 is thus measurable by an absorption spectrum of the emitted light.

First, the inspected object 88 is mounted on the belt conveyor 60 for measurement. Then the projection optical system 70 and spectroscope 72 are moved up and down according to the size of the inspected object 88, so as to make their optical axes 80, 94 aligned with each other and locate the equator part 90 of the inspected object 88 on these optical axes 80, 94.

In this state the light is projected from the lamp 64 toward the inspected object 88. The light 96 emitted from the lamp 64 travels through the aperture 100 of the stop 66 to enter the lens 68. The light properly condensed by the lens 68 is projected onto the region around the equator part 90 of the inspected object 88. The light projected onto the inspected object 88 is reflected and absorbed in part in the surface and inside of the inspected object 88 and thereafter the light is emitted to and received by the spectroscope 72.

The absorption spectrum of the light received by the spectroscope 72 is measured. Absorption spectra differ among the inspected objects 88 and the internal quality of each inspected object 88 can be measured based thereon.

A next example is the measurement of the internal quality of an apple that is resistant to transmission of the light. The maximum diameter is selected for the aperture 100 of the stop 66. In this case the projection amount to the inspected object 88 is large and the amount of light emitted from the inspected object 88 is thus sufficiently large. Therefore, the internal quality of the inspected object 88 is measurable by an absorption spectrum thereof.

The other measurement conditions than this are the same as in the case of the inspected object of the orange, so that the internal quality of the inspected object 88 can be measured based on the absorption spectrum of the emitted light from the inspected object 88.

Modifications of the present embodiment will be described below.

The present embodiment is arranged to move the projection optical system 70 and spectroscope 72 up and down in order to align the optical axis 80 of the projection optical system 70, the optical axis 94 of the receiving lens 92, and the equator part 90 of the inspected object 88 with each other, but another conceivable configuration is such that the position of the belt conveyor 60 carrying the inspected objects 88 is moved up and down. It can also be contemplated that the light projection position onto the inspected object 88 is varied by setting a mirror in the projection optical system 70 and changing the angle of this mirror. In a further configuration, a mirror is provided between the receiving lens 92 of the spectroscope 72 and the inspected object 88 so that the emitted light from the equator part 90 of the inspected object 88 is always received with changing the angle of this mirror.

The aperture 100 was arranged to be changed in the concentric circular shape in the present embodiment, but the aperture may also be of another shape as long as it can control the amount of light passing through the stop 66. In another conceivable configuration the shape of the aperture is constant and the opening time of the aperture is controlled. The control may also be conducted using filters.

In the present invention the position of the inspected object on the moving means can be detected and the measurement can be carried out when the inspected object is located correctly at the measurement position. The details will be described below.

Figure 10:
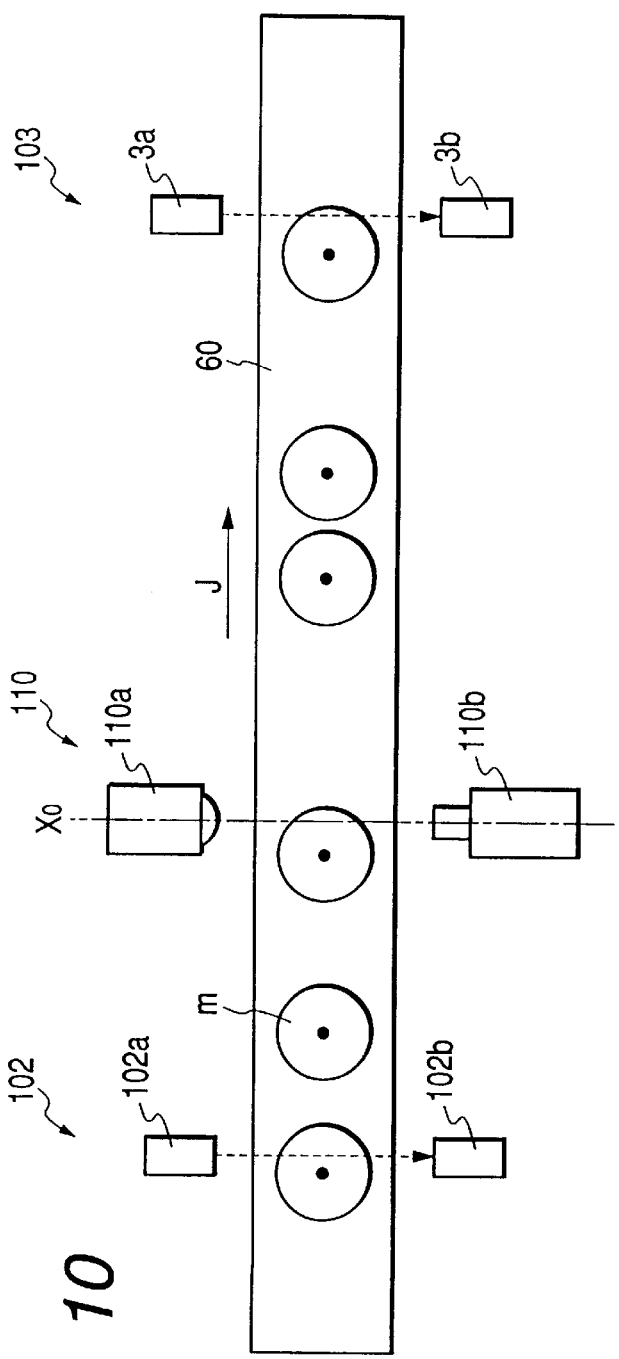
FIG. 10 is a top plan view to show the schematic structure of a measuring device for measuring the sugariness and acidity of oranges as the first embodiment of the present invention.
Figure 11:
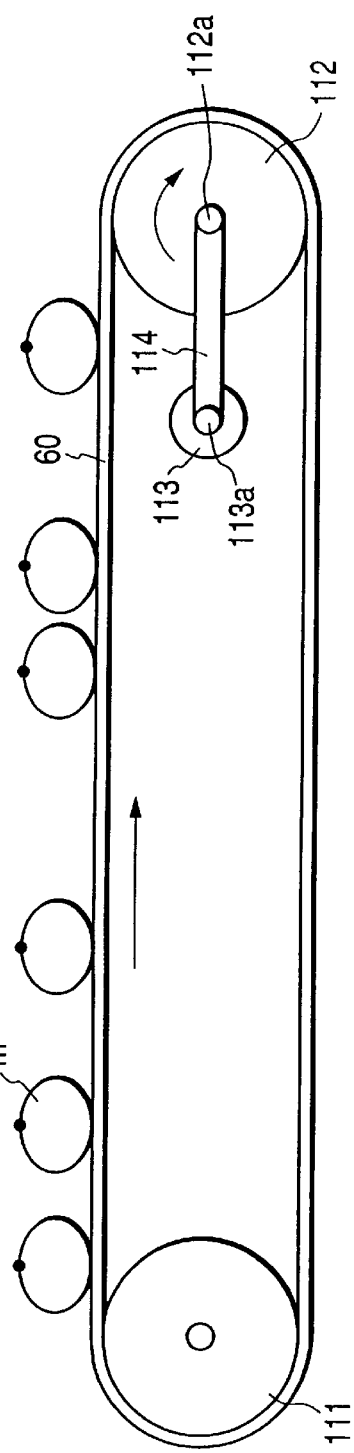
FIG. 11 is a side view of the measuring device of FIG. 10.

FIG. 10 and FIG. 11 are diagrams for conceptually explaining the schematic structure of a sugariness and acidity measuring device of the present embodiment, in which FIG. 10 is a top plan view and FIG. 11 is a side view.

In FIG. 10 the belt conveyor 60 is moving along the arrow direction J in the figure, i.e., to the right in the figure. There are oranges m as inspected objects mounted at random on the belt conveyor 60. In FIG. 10 six oranges m are placed on the conveyor 60.

Figure 12:
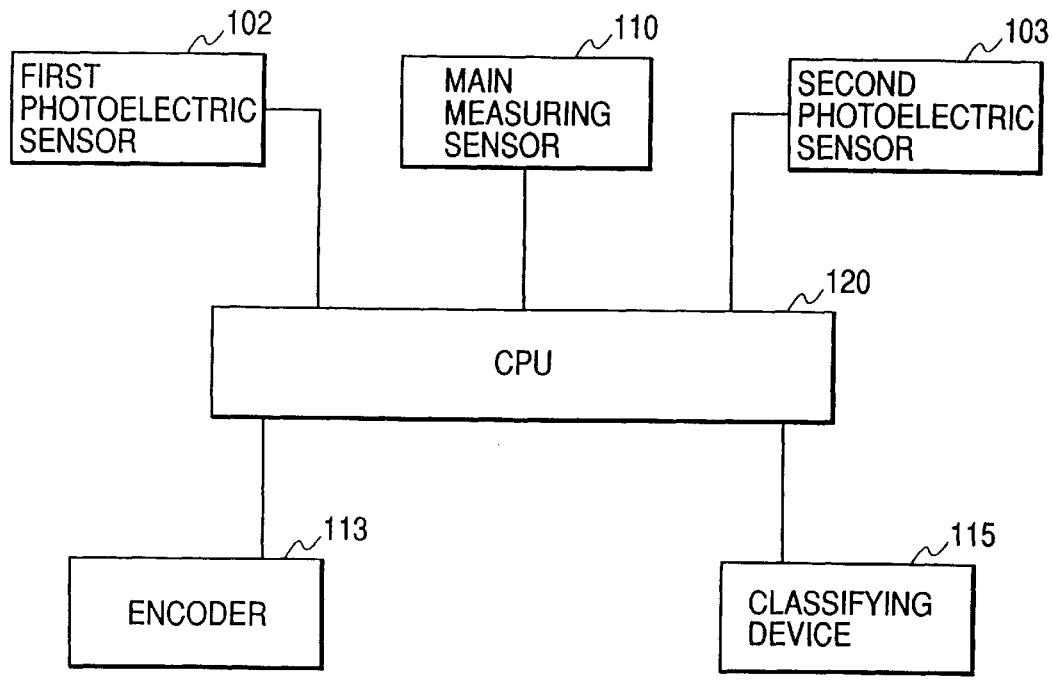
FIG. 12 is a block diagram of a control system in the measuring device of the embodiment.

A first photoelectric sensor 102, which is composed of a pair of light projecting element 102*a* and light receiving element 102*b* such as a photodiode or the like, is located on either side of the conveyor and at the upstream extremity of the belt conveyor 60. The light projecting element 102*a* emits detection light toward the light receiving element 102*b*. The light receiving element 102*b* receives it to convert the light to an electric signal and outputs the electric signal to CPU 120 (central processing unit: FIG. 12) described hereinafter.

Likewise, a second photoelectric sensor 103, which is composed of a pair of light projecting element 103*a* and light receiving element 103*b* such as a photodiode or the like, is located on either side of the conveyor and at the downstream extremity of the belt conveyor. As in the case of the first photoelectric sensor 102, the light projecting element 103*a* also emits detection light toward the light receiving element 103*b* in the second photoelectric sensor 103 and the light receiving element 103*b* receives it to convert the light to an electric signal and outputs the electric signal to the CPU 120.

On the upstream side in the middle part of the belt conveyor there is a measurement system for actually performing the main measurement of sugariness and acidity of the inspected object. The measurement system is composed of a light source 110*a* for emitting light including the near-infrared region and a spectroscope 110*b* for receiving light having been transmitted by the inspected object m. The spectroscope 110b spectroscopically resolves the received light into a plurality of frequency components and outputs signals according to intensities of the respective component beams to the CPU 120. The details of the measurement will be omitted from the description herein, because it is known.

In the above structure the dimensions of each part are determined arbitrarily according to circumstances and conditions, and in a preferred example of the present embodiment the distance between the first and second photoelectric sensors along the moving direction of the belt conveyor is set to 800 mm and the center of the measurement system (the position indicated by the chain line $X_0$ in the figure) is set at the position 350 mm apart from the first photoelectric sensor. The moving speed of the belt conveyor 60 is set to approximately 300 to 1000 mm/sec. It should be noted that the various numerical values described above are just an example and the present invention is by no means intended to be limited to this example.

Next referring to FIG. 11, the belt conveyor 60 is wound around two rollers 111 and 112. The downstream roller 112 is connected to a power source not illustrated and rotates in the direction of the arrow in the figure (clockwise) to drive the belt 60. A rotational shaft 112a of the downstream roller 112 is connected through a belt 114 to a rotational shaft 113a of an encoder 113 disposed adjacent to the roller 112.

In this structure the encoder 113 rotates in connection with movement of the belt conveyor 60. The encoder 113 outputs a pulse signal according to an amount of the rotation and in the present embodiment the output of the encoder is set so as to be one pulse per moving distance 0.1 mm of the belt conveyor. Therefore, the moving amount of the belt conveyor 60 can be monitored by counting the number of output pulses from the encoder 113.

The operation of the device of the present embodiment will be described next. First, FIG. 12 is a block diagram to show the schematic structure of the control system in the present device. As described above, the outputs of the first photoelectric sensor 102, the second photoelectric sensor 103, the sensor 110 for the main measurement, and the encoder 113 are connected to the CPU 120 for controlling the operation of the entire device. The CPU 120 converts the input signals to digital signals as occasion may demand and uses them as information for controlling the operation of the device. In addition, an inspected object collecting and classifying device 115 is further connected to the CPU 120. The collecting and classifying device 115 is a device disposed downstream of the belt conveyor 60 and arranged to collect the inspected objects discharged from the belt conveyor 60 and classify them according to the necessity. As detailed hereinafter, the collecting and classifying device classifies the inspected objects according to the measurement result in response to instructions from the CPU 120.

The actual measurement is carried out as follows.

While the belt conveyor 60 is driven at the constant rate, the inspected objects m (oranges herein) are successively supplied from inspected object supply means not illustrated at the upstream end of the conveyor 60 to be mounted at random on the belt conveyor 60. The term "at random" herein means random placement without using any particular means for positioning, adjusting the distance between inspected objects, or providing partitions on the conveyor.

Figure 13:
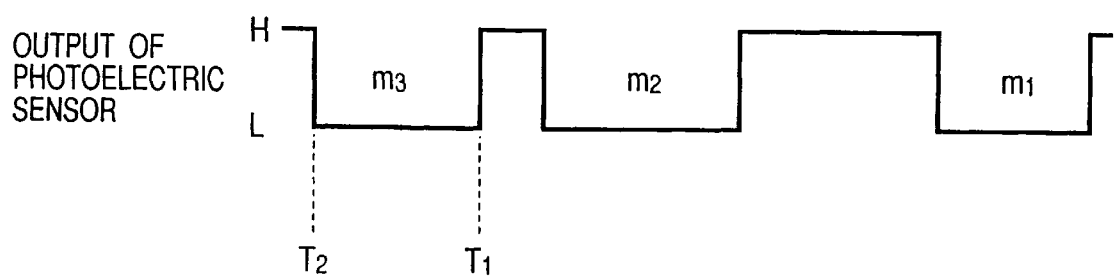
FIG. 13 is a diagram to show an example of an output signal waveform of a photoelectric sensor in the measuring device of the embodiment.

The light emitting element 102a of the first photoelectric sensor always emits the light of constant intensity toward the light receiving element 102b during the measurement operation of the device. When nothing intercepts the light between the both elements, the light receiving element 102b always receives the light of constant intensity, so that the output signal of the first photoelectric sensor is of a constant level (high level H). The inspected objects are supplied from the upstream end of the belt conveyor onto the conveyor 60 and are moved to the downstream with the driving of the conveyor 60. When the first inspected object reaches the position of the first photoelectric sensor, the inspected object m comes to intercept rays traveling from the light emitting element 102a to the light receiving element 102b. While the inspected object m passes the position of the first photoelectric sensor, the light receiving element 102b receives no light, so that the output signal of the first photoelectric sensor is kept in a low level L, lower than the aforementioned high level H, during a period according to the width of the inspected object m. In this way the output signal of the first photoelectric sensor becomes a signal waveform of a rectangular form including the information that indicates the time period in which the inspected object m passed the position of the sensor. An example of this output signal waveform of the photoelectric sensor is illustrated in FIG. 13. In FIG. 13 three low-level portions represented by $m_1$ to $m_3$ indicate that three inspected objects passed the position of the first photoelectric sensor.

As described above, the pulse signal indicating the moving amount of the belt conveyor 60, outputted from the encoder 113, is also input into the CPU 120. With this pulse signal, the passage data of the inspected objects m obtained based on the above-stated output signal of the first photoelectric sensor can be converted to information about the sizes and positions of the inspected objects. More specifically, for example, two edges $T_1$, $T_2$ of a low-level portion $m_3$ of the signal in FIG. 13 correspond to passage start and end times, respectively, when the inspected object $m_3$ passed the position of the first photoelectric sensor, and the lateral diameter of the inspected object $m_3$ can be computed by subtraction between pulse counter numbers of the encoder at the both times $T_1$, $T_2$. For example, supposing the pulse counter number at $T_1$ is 61400 and the pulse counter number at $T_2$ is 62000, the number of pulses during the passage of the inspected object $m_3$ at the position of the photoelectric sensor is obtained as follows.

$$62000-61400=600$$

Since the encoder 113 is set to generate one pulse per movement of 0.1 mm (i.e., 0.1 [mm/pulse]), the lateral diameter of the inspected object $m_3$ can be recognized as follows.

$$600 \text{ [pulses]} \times 0.1 \text{ [mm/pulse]}=60 \text{ mm}$$

Counting the encoder pulse number after the inspected object leaves the position of the first photoelectric sensor, the CPU can also always obtain the positional information of the inspected object.

The CPU 120 calculates the position of the center of the lateral diameter, i.e., the position of the center of each inspected object in the moving direction from the information about the size (lateral diameter) of the inspected object m obtained as described above. The CPU 120 further obtains the timing when the center of the inspected object m passes the main measurement position $X_0$, based on the information about the center position calculated and the moving amount obtained from the encoder pulse signal, and controls the measuring device to perform the measurement of sugariness and/or acidity at the timing obtained.

This device further has the second photoelectric sensor near the downstream extremity of the belt conveyor. The second photoelectric sensor measures the lateral diameter and position of the inspected object in the same manner as the first photoelectric sensor does, and compares measured data with the data obtained by the first photoelectric sensor for the same inspected object to detect whether a positional deviation of the inspected object occurred midway of the movement on the belt conveyor. Specifically, according to processing similar to that of the first photoelectric sensor signal, the lateral diameter information and center position information is obtained and the lateral diameter and center position of the same inspected object are compared with those obtained from the signal of the first photoelectric sensor. If there is a deviation of either one there is no guarantee that this measurement was carried out at the correct position. Then the CPU 120 sends an error signal to the collecting and classifying device 115 disposed downstream of the belt conveyor and the collecting and classifying device classifies the inspected object corresponding to the error signal as an inspected object to be measured again.

The operation of the CPU 120 in the process described above is illustrated in the flowchart of FIG. 14.

Figure 14:
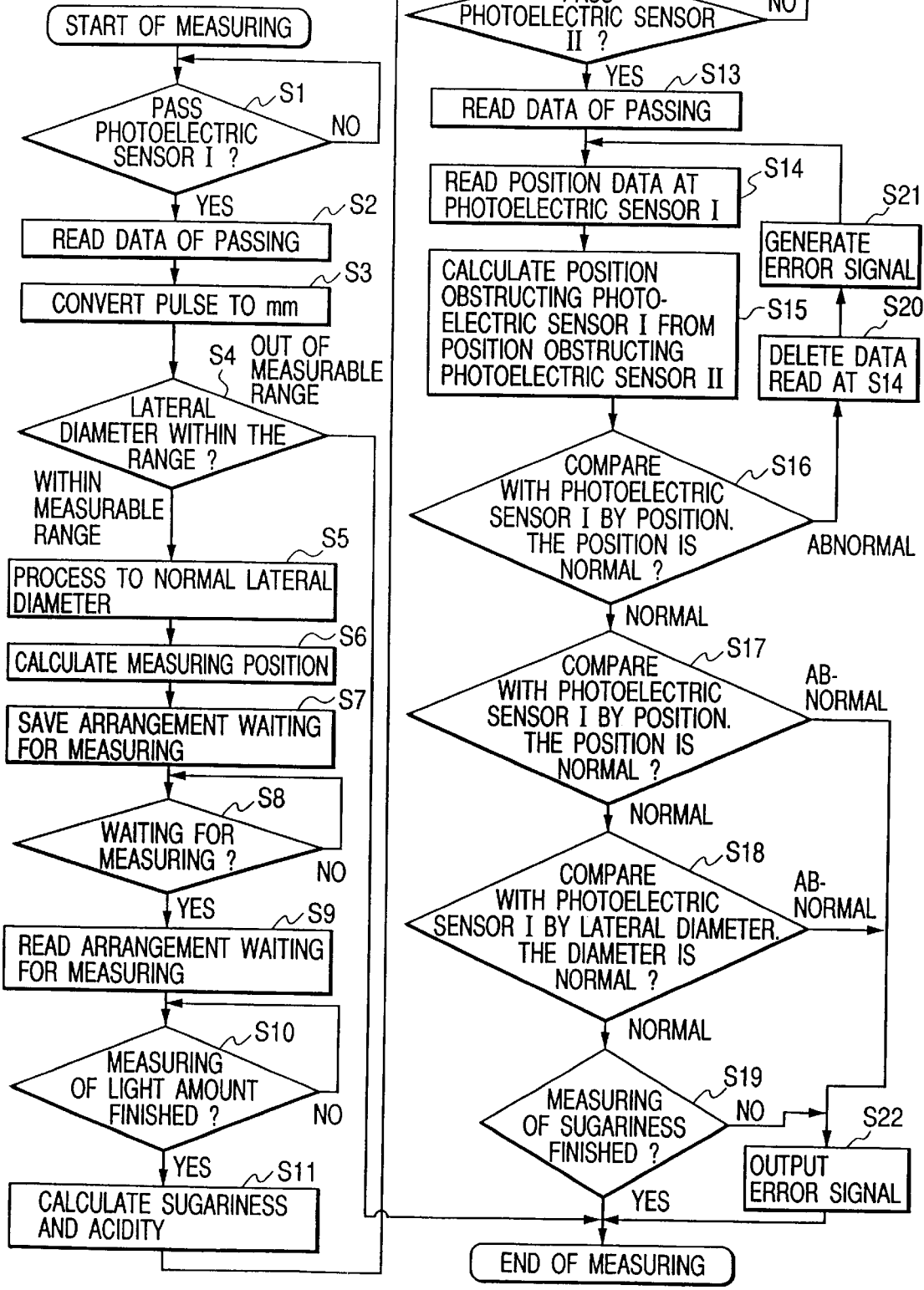
FIG. 14 is a flowchart to show the operation of a CPU in the measuring device of the embodiment.

In the operation illustrated in the flowchart of FIG. 14, after the start of the measurement, step S1 is first carried out to detect whether an inspected object has passed the first photoelectric sensor. The CPU waits for detection of passage here and proceeds to step S2 with detection of passage.

Step S2 is to read the passage data (pulse data) of the inspected object based on the signal obtained from the first photoelectric sensor and the pulse signal from the encoder.

Then the CPU converts the passage data of the inspected object to the lateral diameter data (in units of mm) based on the pulse data in step S3.

In step S4 the CPU next determines whether the lateral diameter is within a normal range. When the lateral diameter is over the normal range, it is assumed that two or more inspected objects are placed close to each other so as to become continuous. In that case the center position of each inspected object cannot be specified and the measurement is impossible.

Therefore, the CPU proceeds to step S22 to output an error signal.

When step S4 results in determining that the lateral diameter is within the measurable range, the CPU goes to Step S5 to enter a process for normal lateral diameters.

In step S6 the CPU calculates the main measurement position as a position of the center of the lateral diameter.

In step S7 the CPU once saves the main measurement position obtained in step S6, as arrangement information of the inspected object in a waiting state for the measurement.

In step S8 the CPU determines whether there is an unmeasured object for which the arrangement information in the measurement-waiting state is stored. In other words, the CPU stands by before the arrangement information of an inspected object in the measurement-waiting state is obtained.

When step S8 results in determining that there is an inspected object in the measurement-waiting state, the CPU reads the arrangement information of the inspected object in the measurement-waiting state in step S9.

In step S10 the CPU then stands by before the main measurement is finished as to the amount of transmitted light through the inspected object for the measurement of sugariness and acidity.

After completion of the measurement, the CPU goes to step S11 to calculate the sugariness and acidity based on the measurement result obtained in step S10 and store the result in connection with the positional data.

After that, in step S12 the CPU stands by before the inspected object has passed the second photoelectric sensor at the downstream end.

When the passage of the inspected object is detected in step S12, the CPU goes to step S13 to read the passage data of the inspected object based on the signal obtained from the second photoelectric sensor.

Then in step S14 the CPU reads the position and lateral diameter data of the inspected object upon the passage at the first photoelectric sensor in the sequentially next data out of the data with which the sugariness and acidity operation is completed.

In step S15 the CPU then calculates from the position data at the second photoelectric sensor read in S13, position data when the inspected object corresponding to the data passed the first photoelectric sensor, based on the distance between the first and second photoelectric sensors. This is an operation to subtract the distance between the two sensors from the position data obtained by the second photoelectric sensor, thereby obtaining where the inspected object of interest should have been located on the past occasion of the passage at the first photoelectric sensor.

In step S16 the CPU then compares the position (II) at the first photoelectric sensor, obtained from the position at the second photoelectric sensor in S15, with the actual position (I) at the first photoelectric sensor, read in S14. If the position (II) obtained in S15 deviates over a predetermined amount on the upstream side with respect to the position (I) read in S14 (or if the detection timing is too late) the inspected object is considered to drop out of the conveyor in the path from the first photoelectric sensor to the second photoelectric sensor. Therefore, the CPU regards it as abnormal and goes to step S20 to delete the relevant data read in step S14. The CPU then generates an error signal in step S21 and returns to S14 to read the next data at the first photoelectric sensor.

When in the position comparison in step S16 the deviation of the position (II) to the upstream with respect to the position (I) is not more than the predetermined amount (or when the detection timing is not too late), the CPU regards it as normal and goes to step S17 to determine this time whether the position (II) deviates over a predetermined amount on the downstream side with respect to the position (I). When the deviation is over the predetermined amount on the downstream side (or when the detection timing is too early), it is assumed that the positional deviation of the inspected object occurred on the conveyor and there is no guarantee that the main measurement was carried out at the correct measurement position. Therefore, the CPU regards it as abnormal and goes to step S22 to generate an error signal.

When in step S17 the deviation to the downstream is not more than the predetermined amount, the CPU regards it as normal and goes to step S18. In step S18 the CPU determines whether the lateral diameter of the inspected object obtained from the passage data at the second photoelectric sensor is equal to that obtained from the data at the first photoelectric sensor before the main measurement, which was read in S14. In the abnormal case, i.e., where they are not equal, it is considered that there occurred a deviation in the mount direction of the inspected object during the intermediate process (i.e., there occurred a change of the posture, for example, a change of the posture of the inspected object when the orange being the inspected object moved on the conveyor from a lying state to an upright state) or an identification error of the inspected object, and then the CPU proceeds to step S22 to generate an error signal.

When the determination in step S18 is normal, the CPU goes to step S19 to determine whether the measurement of sugariness and acidity for the inspected object of interest is finished. If the measurement is not finished yet the CPU proceeds to step S22 to generate an error signal.

When step S19 results in determining that the measurement is finished, the CPU terminates the measurement process under a decision that there was no problem in the measurement process and the correct measurement was carried out.

Steps S21 and S22 are steps carried out when the various anomalies are determined in the above various determination steps. The CPU outputs an error signal to the collecting and classifying device to direct the collecting and classifying device to classify the measured object of interest into a category of inspected objects to be measured again.

The present invention was described above with reference to the embodiment, but it should be noted that the embodiment described above is just an example and the present invention is by no means intended to be limited to the various elements of the embodiment and can involve a variety of modifications.

For example, the present embodiment has the inspected object supply means on the upstream side of the belt conveyor to automatically supply the inspected objects, but the device may also be arranged to place each of the inspected objects onto the conveyor by manual operation. In practice, where the inspected objects are fruits or vegetables easy to bruise in the event of collision, such as peaches, they are often mounted by hand.

The device of the present embodiment was directed to the measurement of oranges, but the present invention can also be applied to various devices adapted for the measurement of the other fruits or vegetables, or to devices adapted for measurement during movement of some inspected articles mounted on the moving means, without having to be limited to the fruits or vegetables.

Although the device of the present embodiment is arranged to measure the sugariness and acidity, the present invention can also be applied to measurement of the other internal qualities of the fruits or vegetables, of course.

Figure 15:
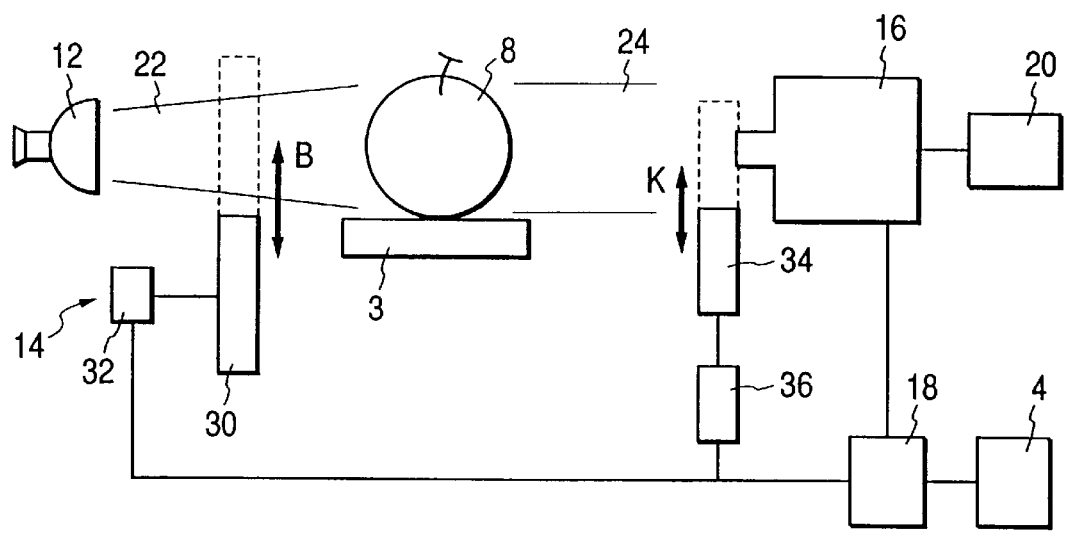
FIG. 15 is a schematic diagram to show the overall structure of the second embodiment according to the present invention.

The second embodiment of the present invention will be described below referring to FIG. 15. Here, the description of the same components as in the first embodiment will be omitted and only different portions will be described herein.

The receiving lens of the spectroscope 16 is provided with a shutter 34 of an opening and closing type, opening and closing of which is controlled by a shutter driving mechanism 36 using a solenoid. The shutter is moved in the vertical directions K.

The control section 18 is connected to the calibration driving mechanism 32 and to the shutter driving mechanism 36 and outputs signals for driving them to control the driving of the calibration driving mechanism 32 and the shutter driving mechanism 36.

The shutter driving mechanism 36 is arranged to drive the shutter 34 immediately after completion of the calibration by a driving signal from the control section 18. The shutter 34 is moved and positioned over the entire surface of the receiving lens so as to prevent the external light from entering the receiving lens of the spectroscope 16. In this state current (dark current) appearing from photoelectric conversion in the control section 18 is very weak. This originates in the noise etc. specific to the device and more accurate measured values can be obtained by subtracting the value of the dark current from the above measured values.

Described below is the step of measurement of the internal quality of the fruit or vegetable according to the present embodiment. Only different portions from the first embodiment will be described herein, too.

After completion of the measurement of the base line, the spectroscope 16 outputs an end signal to the control unit 18. Receiving this signal, the control section 18 outputs a driving signal to the solenoid of the shutter driving mechanism 36. The shutter driving mechanism 36 moves the shutter 34 so as to cover the entire surface of the receiving lens of the spectroscope 16 in response to this driving signal, thereby preventing the external light from entering the spectroscope 16. In this state the spectroscope 16 measures the dark current. The dark current results from the noise etc. specific to the device, which is a very small value. The arithmetic operation unit 20 subtracts this value from the base line or from a measured value of each inspected object 8, whereby a more accurate measured value can be obtained for each object.

Here, the transmittance T of each inspected object 8 (the i-th object out of the total n), used in the evaluation of the internal quality of the inspected objects 8, is expressed by the following equation:

$$Ti=(Si-D)/(R-D) \qquad (1)$$

where Si is a measured value of the frequency spectrum of the output light, after absorbed in part within the inspected object 8, R is average of current values by the calibration, and D is an average of dark current values. Namely, the transmittance of the inspected object 8 is defined by a ratio of the output light from the inspected object 8 to the output light from the lamp 12 through the filter. In each of the numerator and the denominator, the average D of dark current values is subtracted from the measured value Si of the frequency spectrum obtained from the output light or from the average R of current values obtained by the calibration. This eliminates the noise specific to the spectroscope 16.

The present embodiment is arranged to measure the dark current immediately after the calibration, but the calibration may also be carried out immediately after the measurement of the dark current.

The other structure, steps, and effects than above are the same as in the first embodiment.

The third embodiment of the present invention will be described referring to FIG. 16 to FIG. 18. The same components as in the first embodiment will be omitted from the description and only different portions will be described herein.

Figure 16:
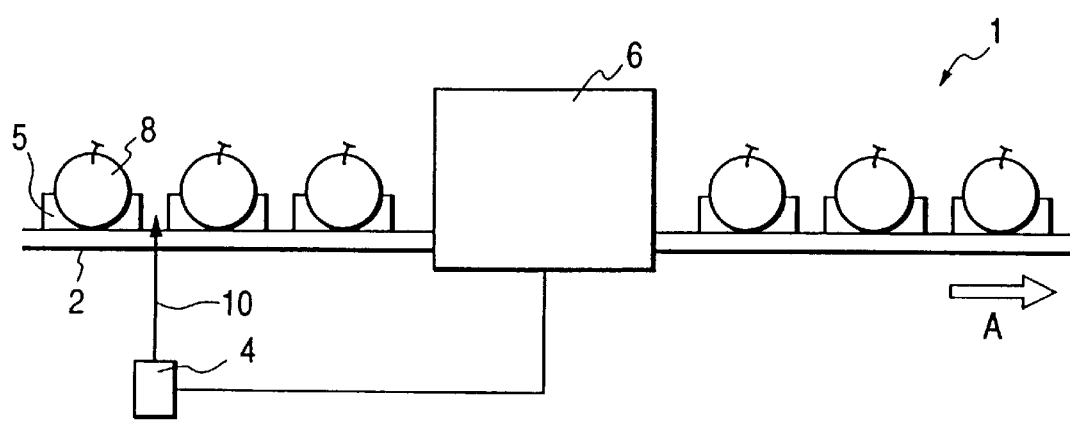
FIG. 16 is a schematic diagram to show the overall structure of the third embodiment according to the present invention.

As illustrated in FIG. 16, the device 1 of the present embodiment is composed of shield buckets 5, the sensor 4, the measuring section 6, and so on.

The inspected objects 8 such as melons or the like are mounted on the respective shield buckets 5 mounted on the belt conveyor 2. The belt conveyor 2 moves the inspected objects 8 in the longitudinal direction A thereof. The sensor 4 and measuring section 6 are disposed in the middle of the moving direction A of the belt conveyor 2. The sensor 4 is a photoelectric sensor, which is arranged to project infrared light 10 onto the belt conveyor 2 and measure the reflected light therefrom whereby the sensor 4 can obtain information about presence/absence, spacing, and position of the inspected object 8 on the belt conveyor 2. The measuring section 6 is located downstream of the sensor 4 in the moving direction of the belt conveyor 2 and is arranged to project light toward the inspected object 8 and measure the internal quality of the inspected object 8 from light outgoing from the inspected object 8.

Figure 17:
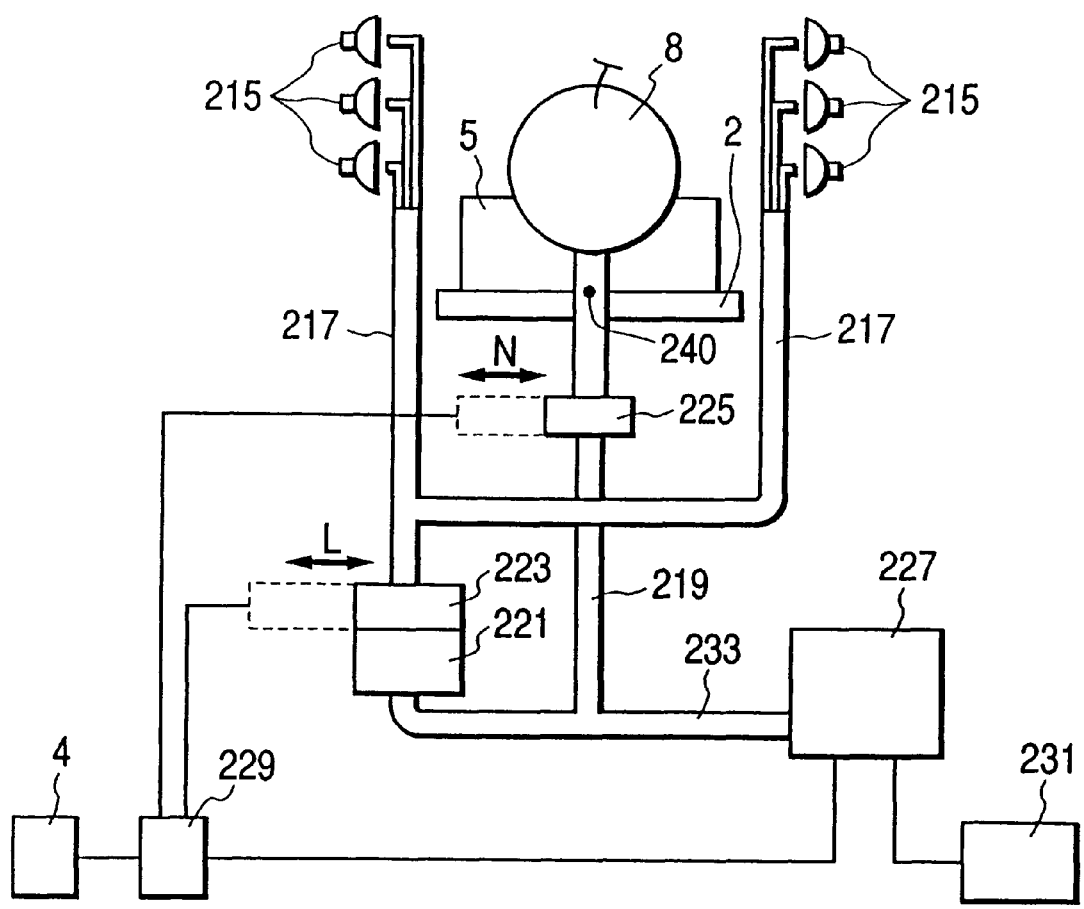
FIG. 17 is a schematic diagram to show the structure of the measuring section of the third embodiment according to the present invention.

The measuring section 6, as illustrated in FIG. 17, is composed of lamps 215, first optical fibers 217, a second optical fiber 219, a filter portion 221, a first shutter 223, a second shutter 225, a spectroscope 227, the optical sensor 4, a control unit 229, an arithmetic operation unit 231, and so on.

The lamps 215 are placed so as to be capable of projecting the light from the side to almost the whole of the inspected object 8, three to five lamps being located on either side of the inspected object 8. The light projected from the lamps 215 toward the inspected object 8 is one having wavelengths, for example, in the near-infrared region (650 to 950 nm). After this light is absorbed in part inside the inspected object 8 receiving the projected light, transmitted light is emitted from the inspected object 8.

The first optical fibers 217 in the number equal to the number of lamps 215 are provided between the lamps 215 and the inspected object 8. A light receiving portion of each optical fiber 217 is directed toward the associated lamp 215, so as to be capable of directly receiving the light from the lamp 215.

The first shutter 223 and filter portion 221 are disposed in the middle of the optical paths of the first optical fibers 217. The filter portion 221 is, as the filter 30 shown in FIG. 3, composed of ND filters and a diffused plate. The first shutter 223 is arranged to be opened or closed by the solenoid, based on whether the inspected object 8 is present or absent in the measuring section 6. While the first shutter 223 is in an open state, the light from the first optical fibers 217 is incident to the filter portion 221. Since the structure and effect of the filter portion 221 are similar to those of the filter 30 of the first embodiment, the description thereof is omitted herein.

The second optical fiber 219 having the second shutter 225 is connected to an aperture portion 240 in the bottom part of the shield basket 5. The second shutter 225 is opened and closed by the solenoid (not illustrated), based on whether the inspected object 8 is present or absent in the measuring section 6. While the second shutter 225 is in an open state, the light having been transmitted by the inspected object 8 travels through the aperture portion 240 in the bottom part of the shield basket 5 to enter the second optical fiber 219.

The first and second optical fibers 217, 219 join to form the third optical fiber 233 to be connected to the spectroscope 227, so that the spectroscope 227 can receive the light from the lamps 215 through the filter portion 221 of the first optical fibers 217 or the transmitted light from the inspected object 8 through the second optical fiber 219. The spectroscope 227 can measure an absorption spectrum of the light received or the amount of the light. This permits the measurement of the internal quality such as the sugariness or the like of the inspected object 8.

The sensor 4 described above is connected to the control unit 229 and the control unit 229 converts the quantity of the light incident to the optical sensor 4 to current by photoelectric conversion and can determine whether the inspected object 8 is present or absent in the measuring section 6, based on whether the current is larger than a predetermined value. Therefore, the control unit 229 can detect the spacing between the inspected objects 8 on the conveyor 2, based on the determination. The above predetermined value is a value determined according to the kind, the size, measuring speed, etc. of the inspected objects 8, which is set by the user of the device before the start of the measurement or during the measurement.

Further, the control unit 229 is connected to the first shutter 223 and to the second shutter 225 and outputs signals for driving them. When the spacing between the inspected objects 8 is less than the predetermined value, the second shutter 225 is opened while the first shutter 223 is placed so as to interrupt incidence of light to the filter portion 221. In this case the spectroscope 227 receives the light from the shield basket 5 through the second optical fiber 219 but does not receive the light from the first optical fibers 217. In contrast with it, where the spacing between the inspected objects 8 is not less than the predetermined value, the first shutter 223 is opened while the second shutter 225 is placed so as to interrupt incidence of the light to the second optical fiber 219. In this case the spectroscope 227 does not receive the light from the second optical fiber 219 but receives the light from the lamps 215 through the filter portion 221. The calibration of the spectroscope 227 is carried out in this state, based on the light from the filter portion 221. Namely, the calibration of the device can be carried out on arbitrary occasions, not only at the start of the measurement but also during the measurement, with the light traveling through the filter 221, so that the internal quality of the fruits or vegetables can be measured more accurately without being affected by the variations of the base line due to the measurement.

The arithmetic operation section 231 is connected to the spectroscope 227 and receives an input of current of a frequency spectrum based on the transmitted light from the inspected object 8 or current in the calibration. The arithmetic operation section 231 can measure the internal quality of the inspected object 8 without influence of the variations of the base line, the noise of the spectroscope 227, etc., based on these current values.

With the device in the above structure, where the inspected objects 8 arranged in the longitudinal direction of the belt conveyor 2 are measured, the spacing between the inspected objects 8 can be detected, and the calibration of the device and the measurement of the dark current can be performed every time a portion where the spacing between the inspected objects 8 is not less than the predetermined value reaches the measuring section 6. Therefore, the calibration can be carried out on desired occasions, not only before the start of the measurement but also even after the start of the measurement, so that the measurement does not have to be suspended for the calibration. Hence, the internal quality of the fruits or vegetables can be measured accurately by carrying out the calibration of the device for each of the inspected objects 8 without interruption of the measurement.

Described below is the step of the measurement of the internal quality of the fruits or vegetables according to the present embodiment.

First, the calibration of the device and the measurement of the dark current are carried out prior to the start of the measurement. The calibration is carried out in such a manner that with the second shutter 225 being in the closed state, the first shutter 223 is opened to permit the spectroscope 227 to measure the quantity of the light projected thereto from the first optical fibers 217 through the filter portion 221. The quantity of this light is converted to a current value in the spectroscope 227 and this is used as a base line (or a reference value) of the measurement of the inspected objects 8. On the other hand, the measurement of the dark current is carried out in a state in which both the first and second shutters 223, 225 are closed so as to prevent the external light from entering the spectroscope 227. The dark current is current that the spectroscope 227 itself has in the shield state of the spectroscope 227 and current values without influence of the spectroscope 227 itself can be calculated by subtracting the dark current value from measured values thereafter (current values after photoelectric conversion) by the spectroscope 227.

The measurement of the internal quality of the inspected objects 8 is carried out when each of the inspected objects 8 placed along the longitudinal direction of the belt conveyor 2 reaches the measuring section 6 with movement of the conveyor 2. Namely, when an inspected object 8 mounted on the shield basket 5 reaches the measuring section 6, the inspected object 8 is irradiated directly with the light from the lamps 215 and the emergent light, after absorbed in part inside the inspected object 8, is incident to the spectroscope 227 through the aperture portion 240 provided in the lower part of the shield basket 5 and through the second optical fiber 219. The internal quality of the inspected object 8 can be measured based on a frequency spectrum of this light. This is based on the fact that the profile of the frequency spectrum differs depending upon the components in the inspected object 8, because there exist frequencies at which the quantity of light is high because of the components.

The base line varies with continuation of the measurement. This is caused by the environmental change of the temperature or the like of the spectroscope 227, the measuring section 6, or the region around them. The influence due to fluctuations of the base line has to be eliminated in order to obtain correct measured values. In the present embodiment the base line is measured at a position where the spacing between the inspected objects 8 is not less than a predetermined value. This value is stored in the arithmetic operation section 231 connected to the spectroscope 227.

After completion of the calibration and the measurement of the dark current prior to the start of the measurement, the first shutter 223 is closed while the second shutter 225 is opened, whereby the light from the lamps 215 travels through the aperture portion of the shield basket 5 and through the second optical fiber 219 to enter the spectroscope 227. When an inspected object 8 moving on the belt reaches the measuring section 6 in this state, the near-infrared light emitted from the lamps 215 is projected onto the inspected object 8. The light is absorbed in part by the inspected object 8 and is then emergent from the inspected object 8 to enter the spectroscope 227 through the second optical fiber 219. Then the spectroscope 227 measures the internal quality of this inspected object 8.

The internal quality of the inspected objects is measured successively every time the inspected object 8 reaches the measuring section 6 in this way. When during this measurement the photoelectric sensor 4 detects that the spacing between the inspected objects 8 is not less than the predetermined value, the control section 229 determines that the inspected object 8 is absent in the measuring section 6 and outputs a signal for closing the second shutter 225. In response to this signal the solenoid (not illustrated) of the second shutter 225 is driven, so that the optical path from the shield basket 5 to the spectroscope 227 is interrupted. The control section 229 also outputs a driving signal to the solenoid (not illustrated) of the first shutter 223. In response to this driving signal the first shutter 223 opens the optical paths of the first optical fibers 217 having been kept in the interrupted state, whereby the light becomes incident to the spectroscope 227 through the filter portion 221.

The base line of the device can be measured by measuring the quantity of the attenuated light by this filter portion 221. Fluctuations of the base line can be followed up as occasion may demand. The measured value of the base line is stored in the arithmetic operation section 231.

Here, the transmittance discussed below is used for the evaluation of the internal quality of the inspected objects 8. Specifically, the transmittance T of each inspected object 8 (the i-th object out of the total n) is expressed by the following equation:

$$Ti=(Si-D)/(R-D) \qquad (1)$$

where Si is a measured value of the frequency spectrum from the output light, after absorbed in part within the inspected object 8, R is an average of current values by the calibration, and D is the dark current value. Namely, the transmittance of the inspected object 8 is defined by a ratio of the output light from the inspected object 8 to the output light from the lamps 215 through the filter portion 221. In each of the numerator and the denominator, the dark current value D is subtracted from the measured value Si of the frequency spectrum obtained from the output light or from the average R of current values obtained by the calibration. This eliminates the noise specific to the spectroscope 227.

Modifications of the present embodiment will be described below.

The first shutter 223 may also be disposed in the middle or at the end of the optical paths of the first optical fibers 217.

The second shutter 225 may also be disposed in the middle or at the end of the optical path of the second optical fiber 219. When the second shutter 225 is disposed at the end on the belt conveyor 2 side, it is preferably set in contact with the belt conveyor 2; it is, however, noted that the second shutter 225 does not always have to be in contact with the belt conveyor 2.

The detection of the inspected object 8 was made by incidence of the light to the photoelectric sensor 4 provided separately, but the determination may also be made according to the amount of the incident light to the second optical fiber 219.

The present embodiment was arranged to mount the inspected objects 8 on the respective shield buckets 5 on the belt conveyor 2 and measure the output light from the bottom part of the shield buckets 5, but the belt of the conveyor may be replaced by a mesh belt that permits the light emerging from the inspected object 8 to be measured from the bottom thereof.

The projection of the light from the lamps 215 to the inspected object 8 can not be effected only from the side, but can also be effected from the top surface or the like as long as the light can be projected to almost the whole of the inspected object 8.

The light emitted from the photoelectric sensor 4 may also be one of the other wavelengths than the infrared light.

The light emitted from the lamps 215 may also be one of the other wavelengths than the near-infrared light.

The lamps 215 may also be replaced by optical fibers and the number thereof does not have to be limited to three, but may also be one, two, or more than three.

The fourth embodiment will be described next. Here, the same components as in the third embodiment are omitted from the description and only different portions will be described.

In the present embodiment the calibration can be carried out on arbitrary occasions. Namely, the calibration can be carried out, irrespective of whether the inspected object 8 is present or absent in the measuring section 6, as the user of this device desires or as occasion may demand.

Described below is the step of the measurement of the internal quality of the fruits or vegetables according to the present embodiment. Only different portions from the third embodiment will be described herein, too.

In the present embodiment, after the start of the measurement of the internal quality of the fruits or vegetables, when the user of this device gives instructions of the calibration start by a mechanical or electrical operation or when the arithmetic operation section 231 or the control section 229 determines that the base line of the measurement is off a certain range, the calibration is carried out automatically, irrespective of whether the inspected object 8 is present or absent in the measuring section 6, by closing the second shutter 225 and opening the first shutter 223.

This permits the calibration to be carried out at an arbitrary time and, therefore, the internal quality of the fruits or vegetables can be measured more accurately while the base line is kept constant.

The other structure, steps, and effects than above are the same as in the third embodiment.

The fifth embodiment will be described next. Here, the same components as in the third embodiment will be omitted from the description and only different portions will be described.

The present embodiment is arranged to carry out the measurement of dark current, following the calibration after the start of the measurement of the internal quality of the fruits or vegetables.

Described below is the step of the measurement of the internal quality of the fruits or vegetables according to the present embodiment. Here, only different portions from the third embodiment will be described, too.

After completion of the measurement of the base line, the first shutter 223 is closed while the second shutter 225 is in the closed state. This opening and closing of the shutters is controlled by signals from the control section 229. In this state the spectroscope 227 measures the dark current. The dark current is current appearing due to the noise etc. specific to the device, which is very small. The arithmetic operation unit 231 subtracts this value from, a measured value of the base line or each inspected object 8, whereby a more accurate measured value can be obtained for each of them.

Here, the transmittance T of each inspected object 8 (the i-th object out of the total n), used in the evaluation of the internal quality of the inspected objects 8, is expressed by the following equation:

$$Ti = (Si-D)/(R-D) \quad (1)$$

where Si is a measured value of the frequency spectrum from the output light, after absorbed in part within the inspected object 8, R is an average of current values by the calibration, and D is an average of dark current values. Namely, the transmittance of the inspected object 8 is defined by a ratio of the output light from the inspected object 8 to the output light from the lamps 215 through the filter 221. In each of the numerator and the denominator, the average D of dark current values is subtracted from the measured value Si of the frequency spectrum obtained from the output light or from the average R of current values obtained by the calibration. This eliminates the noise specific to the spectroscope 227.

The present embodiment is arranged to measure the dark current immediately after the calibration, but the calibration may also be carried out immediately after the measurement of the dark current.

The other structure, steps, and effects than above are the same as in the third embodiment.

The sixth embodiments of the present invention will be described below with reference to FIG. 18 to FIGS. 27A and 27B. The same components as in the first embodiment will be omitted from the description and only different portions will be described herein.

Figure 18:
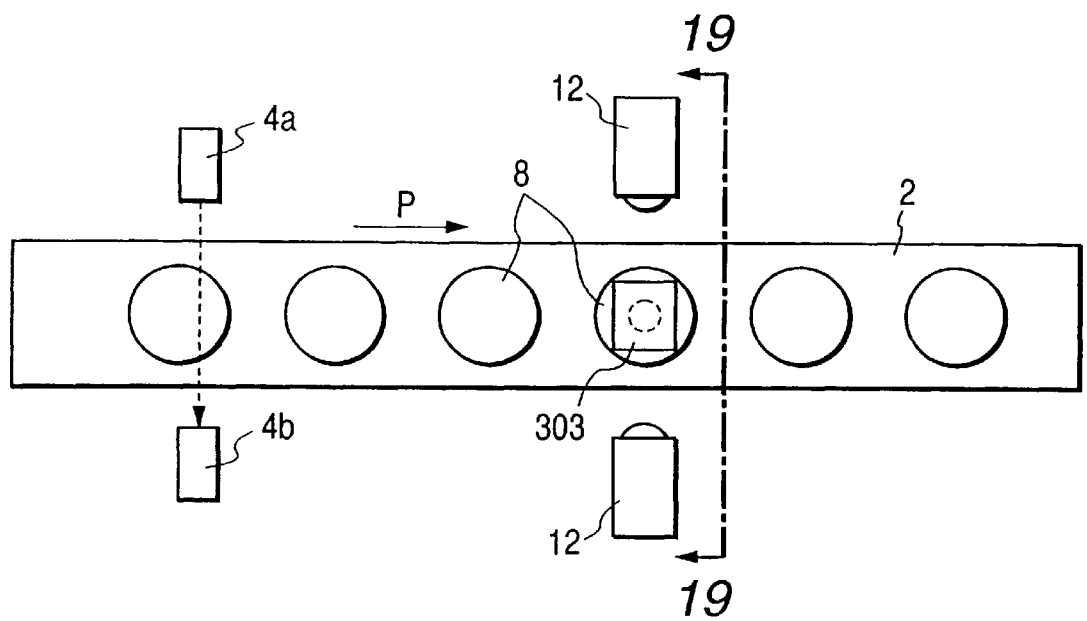
FIG. 18 is a top plan view of an evaluating device for evaluating the internal quality of the fruit or vegetable in the sixth embodiment of the present invention.
Figure 19:
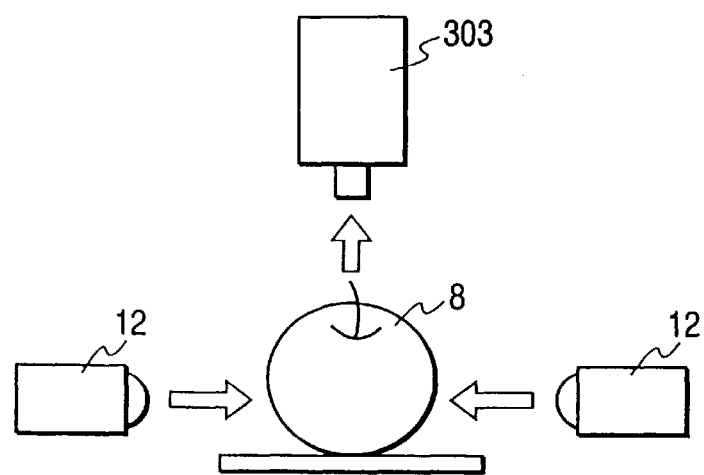
FIG. 19 is a view taken along 19—19 of FIG. 18.

FIG. 18 and FIG. 19 are diagrams to illustrate a device for evaluating the internal quality of fruits or vegetables according to the sixth embodiment of the present invention, wherein FIG. 18 is a top plan view thereof and FIG. 19 is a view along 19—19 of FIG. 18.

The device of the present embodiment has the belt conveyor 2 and a plurality of fruits or vegetables 8 to be inspected are mounted at random thereon. The belt conveyor 2 is driven in the arrow direction P in the figure through a driving shaft not illustrated, and with the driving of the belt conveyor 2 the fruits or vegetables 8 thereon also move along the predetermined conveyance path. The belt conveyor 2 is equipped with an encoder (not illustrated in FIG. 18) to monitor moving amounts of the conveyor in units of 0.1 mm.

Halogen lamp light sources 12 for projecting light toward the inspected fruit or vegetable 8 are disposed on either side of the belt conveyor 2 and at predetermined positions in the conveyance path of the belt conveyor 2. The light sources 12 are arranged to project spot light having the diameter of about 2 cm toward the fruit or vegetable.

A light receiving sensor 303 for receiving light from the inspected fruit or vegetable 8 is provided at the same position as the light sources 12 in the conveyance path and immediately above the belt conveyor 2, as illustrated in FIG. 19. The light received by the light receiving sensor is stereoscopically separated into a plurality of wavelength band channels and spectral analysis thereof is carried out by a known method for checking the absorbance in each channel, thereby measuring and evaluating various internal qualities such as the sugariness, acidity, grade of maturity, and the like of the inspected fruits or vegetables 8. Since this method itself is known, the description thereof is omitted herein.

The light sources 12, the light receiving sensor 303, and part of the conveyor 2 around them are enclosed together in a box not illustrated to be shielded from the external light.

A position sensor 4, which is composed of a pair of light projecting element 4a and light receiving element 4b, is disposed at an upstream position of the belt conveyor 2. The position of a fruit or vegetable 8 on the belt conveyor can be detected from a change of an output signal from the light receiving element occurring when the inspected fruit or vegetable 8 intercepts the light during passage thereof between the light projecting element and the light receiving element. Based on the position information detected herein and moving amount information obtained from the encoder provided in connection with the belt conveyor 2, the measurement timing is controlled so as to carry out the measurement at the moment when the inspected fruit or vegetable 8 passes the position of the measurement by the light sources 12 and light receiving sensor 303.

The lateral diameter of the inspected fruit or vegetable 8 can be calculated from the moving amount information obtained from the encoder and the time period of interception of the light at the position sensor 4. This means that the position sensor 4a, 4b can also be used as a lateral diameter sensor.

In the above structure, the position sensor, the encoder of the belt conveyor, and the light receiving sensor all are connected to the CPU of the device and this CPU carries out the control of the above measurement timing and all the controls of the device including the calculation of the lateral diameter and so on.

The seventh embodiment of the present invention will be described next. The present embodiment is provided with shield plates for intercepting the stray light including the light incident from the light sources 12 directly to the light receiving sensor 303, light reflected by the surface of the inspected fruit or vegetable, light resulting from reflection of the aforementioned reflected light from some elements of the device, and so on. Since the overall structure of the device is similar to that of the sixth embodiment illustrated in FIG. 18, the description thereof is omitted herein and only the part of the shield plates will be described below.

Figure 20A:
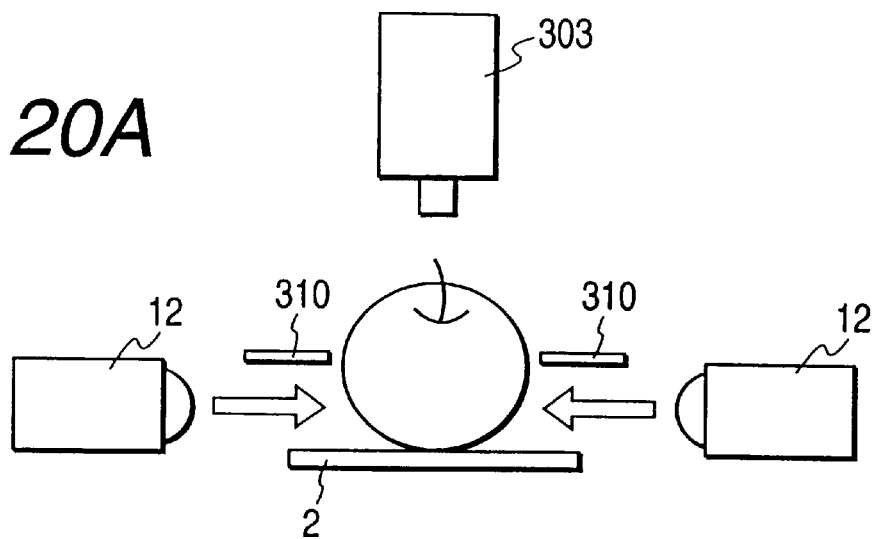
Figure 20B:
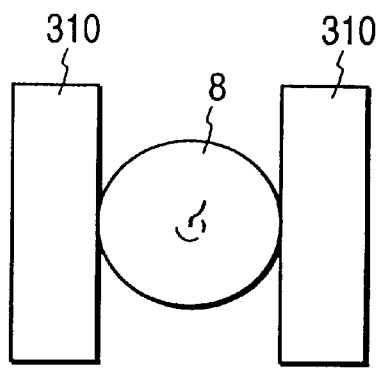
Figure 20B:
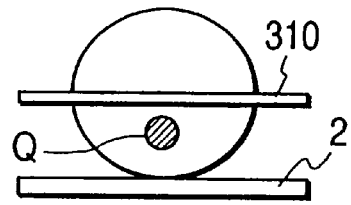

FIGS. 20A, 20B, and 20C are diagrams to show the structure near the measurement position of the device of the seventh embodiment, wherein FIG. 20A is a side view corresponding to FIG. 19 of the sixth embodiment, FIG. 20B is a top plan view of the relevant part, and FIG. 20C is a side view from a direction perpendicular to FIG. 20A.

As illustrated in FIG. 20A and FIG. 20B, the present embodiment is provided with two shield plates 310 disposed on either side of the fruit or vegetable so as to shield the light receiving sensor 303 from the stray light including the light reflected by the surface of the fruit or vegetable 8, the light resulting from reflection of the reflected light from the elements of the device, the light directly traveling from the light sources 12 thereto, and so on. As best shown in FIG. 20C, the shield plates are set approximately horizontally at the position higher than irradiation spots Q where the light from the light sources 12 irradiates the fruit or vegetable 8 and lower than the height of the fruit or vegetable 8.

The separation between the two shield plates 310 can be selected from the following configurations: 1) the separation is set to a fixed length greater than an expected maximum of the lateral diameter of the fruits or vegetables as inspected objects, 2) the separation is made variable every kind of objects with consideration to an expected maximum of the lateral diameter of the fruits or vegetables of each kind to be measured (i.e., every change of measured objects, for example, between apples and peaches), or 3) the separation is made automatically variable according to the lateral diameter of each of the inspected objects.

Figure 21:
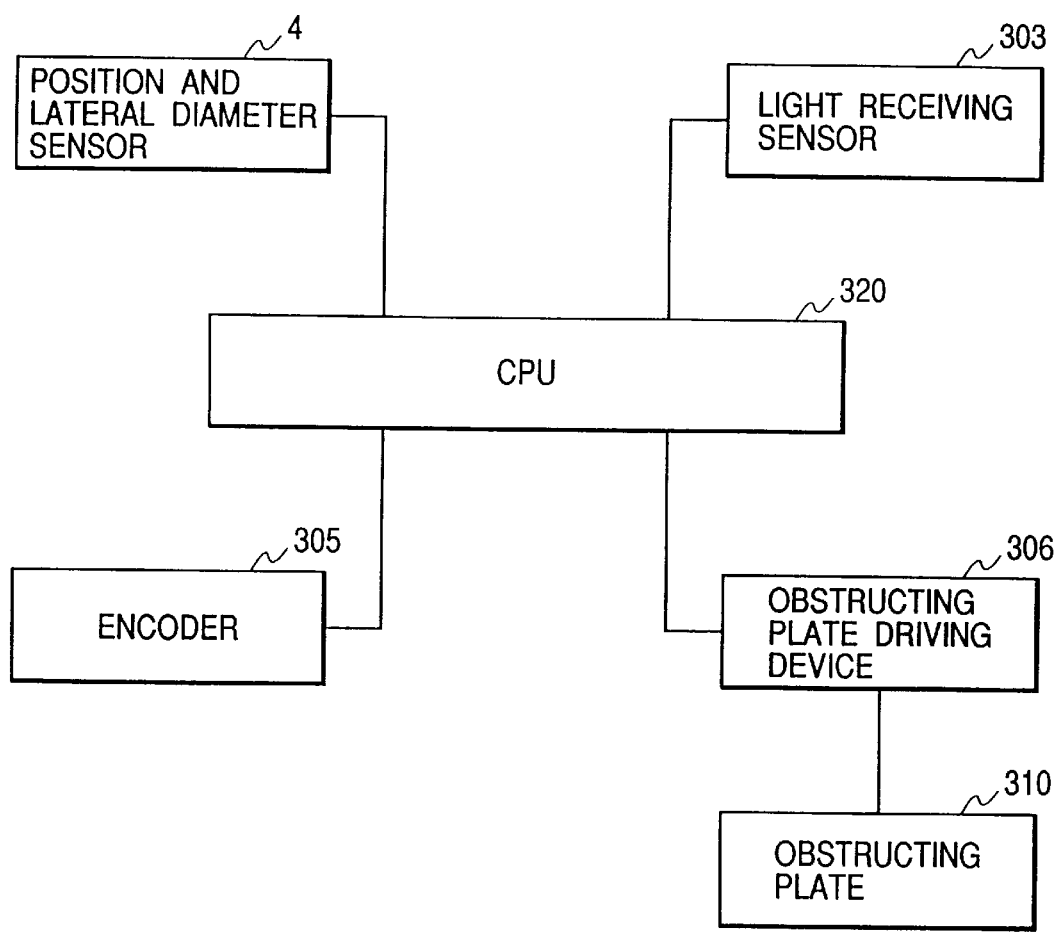
FIG. 21 is a block diagram to show an example of a control system in the device of the seventh embodiment.

A block diagram of a control system of the device in the case of 3) is illustrated in FIG. 21. The CPU 320 calculates the lateral diameter of an inspected object, based on an output from the position and lateral diameter sensor 4, and sends a command to a shield plate driving device 306 so as to realize the separation between the shield plates according to the lateral diameter thus calculated. In response thereto the shield plate driving device 306 drives the shield plates 310 by motor power to set the separation between the shield plates according to the command. Preferably, in order to enhance effectiveness of shield, the separation is set so as to make small the clearance between the shield plates and the inspected fruit or vegetable.

The eighth embodiment of the present invention will be described next. The device of the eighth embodiment is also provided with the shield plates for intercepting the stray light in the similar fashion to the seventh embodiment, but the device of the eighth embodiment is different from the device of the seventh embodiment in the setting position of the shield plates. Since the overall structure of the device in the present embodiment is also similar to that of the sixth embodiment, only the part of the shield plates will be described below.

Figure 22A:
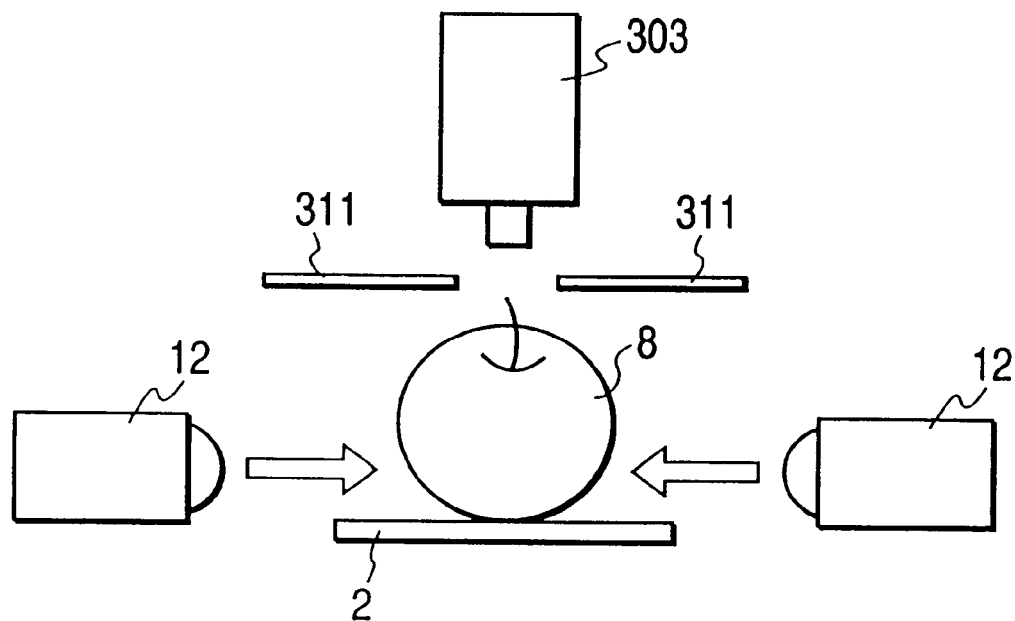
Figure 22B:
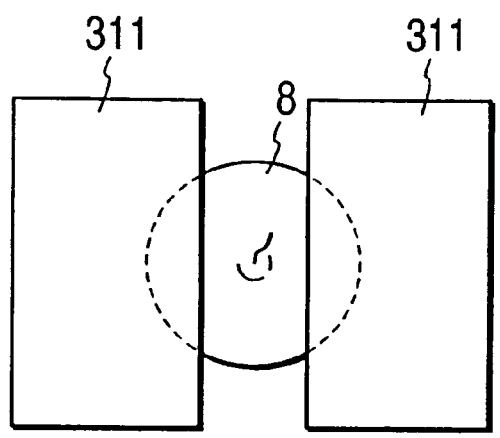

FIG. 22A and FIG. 22B are diagrams to show the structure near the measurement position of the device of the eighth embodiment, wherein FIG. 22A is a side view corresponding to FIG. 19 of the sixth embodiment and FIG. 22B is a top plan view of the relevant part.

As illustrated in FIGS. 22A and 22B, the device of the present embodiment is provided with two shield plates 311 above the inspected fruit or vegetable 8 so as to shield the light receiving sensor 303 from the stray light including the light reflected by the surface of the fruit or vegetable 8, the light coming directly from the light sources 12, and so on.

The height of the two shield plates 311 can be selected from the following configurations: 1) the height is set to a fixed length greater than an expected maximum of the height of the fruits or vegetables as inspected objects, 2) the height is made variable every kind of objects with consideration to an expected maximum of the height of fruits or vegetables of each kind to be measured (i.e., every change of measured objects, for example, between apples and peaches), or 3) the height is made automatically variable according to the height of each of the inspected objects.

Figure 23:
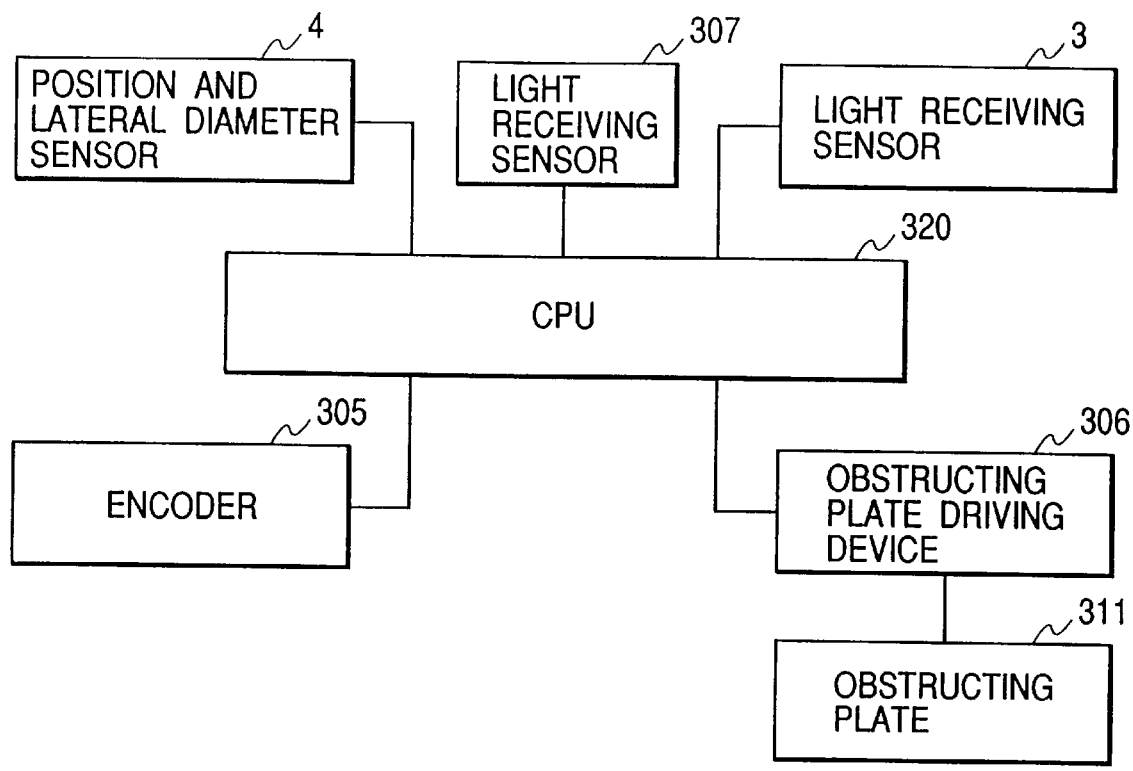
FIG. 23 is a block diagram to show an example of the control system in the device of the eighth embodiment.

A block diagram of a control system of the device in the case of 3) is illustrated in FIG. 23. The CPU 320 calculates the height of the inspected object, based on an output from a height sensor 307, and sends a command for setting the height of the shield plates according to the calculated height to the shield plate driving device 306. In response thereto the shield plate driving device 306 drives the motor for driving the shield plates 311 to set the height of the shield plates 311 so as to be a little higher than the calculated height of the inspected object.

Figure 24:
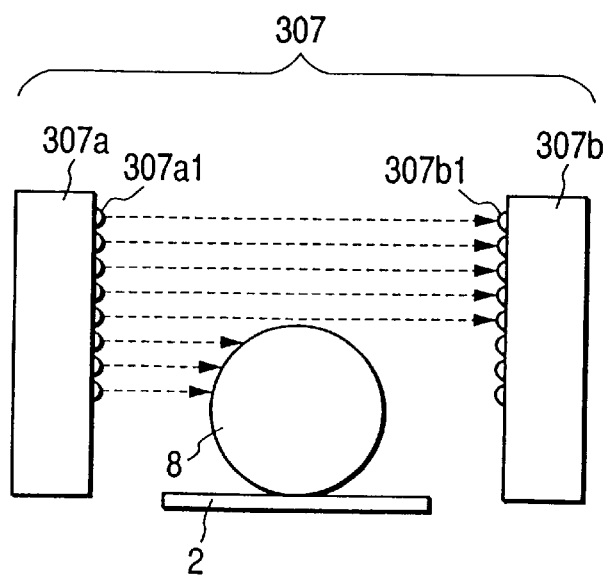
FIG. 24 is a diagram to show an example of a height sensor which can be used in the device of the eighth embodiment.

FIG. 24 shows the structure of the height sensor. The height sensor is disposed on the upstream side of the inspected object conveyance path of the belt conveyor 2. The height sensor is composed of light projecting device 307a and light receiving device 307b opposed to each other on either side of the belt conveyor 2. The light projecting device 307a of the height sensor 307 has a plurality of light projecting elements 307a1 aligned at equal intervals in the vertical direction and the light receiving device 307b has light receiving elements 307b1 aligned each at respective heights matched with those of the corresponding light projecting elements 307a1 of the light projecting device 307a and arranged to receive light beams from the corresponding light projecting elements 307a1. The inspected fruit or object 8, passing between the light projecting device 307a and the light receiving device 307b, intercepts the beams from the light projecting elements 307a1 to the light receiving elements 307b1 located below the height of the fruit or vegetable. Namely, the height of the inspected fruit or vegetable 8 can be detected discretely by detecting up to which height the beams are intercepted.

The ninth embodiment of the present invention will be described next. The device of the ninth embodiment is different from the seventh and eighth embodiments described above in the structure of the shield plates.

Figure 25:
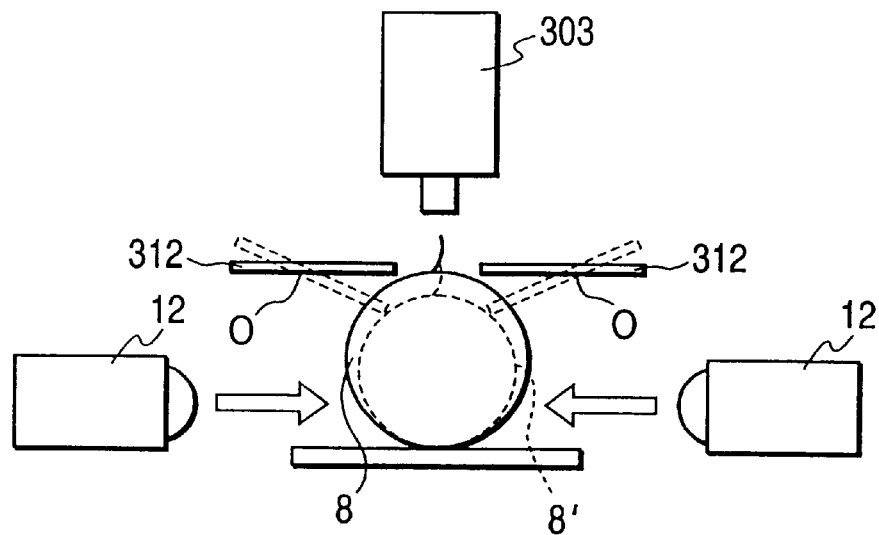
FIG. 25 is a side view to show the structure around the measurement position of an evaluating device for evaluating the internal quality of the fruit or vegetable in the ninth embodiment of the present invention.

FIG. 25 is a side view to show the structure of the shield plates in the device of the ninth embodiment. Each of the shield plates 312 is supported so as to be pivotable about an axis O. The structure of the control system in the device of the present embodiment is similar to that of the eighth embodiment illustrated in FIG. 23. In the device of the present embodiment the angular position about the axis O of the shield plates 312 is adjusted based on information about either the lateral diameter of the inspected fruit or vegetable detected by the position and lateral diameter sensor 4 or the height of the inspected fruit or vegetable detected by the height sensor 307 or about the both, so as to set the clearance between the shield plates and the fruit or vegetable small. FIG. 25 shows the position of the shield plates for a large inspected object 8 illustrated by solid lines and the position of the shield plates for an inspected object 8' a size smaller, illustrated by dashed lines, than the large inspected object 8. The control system of the present embodiment can be constructed in the similar structure to that of the eighth embodiment illustrated in FIG. 23 and described above.

Figure 26:
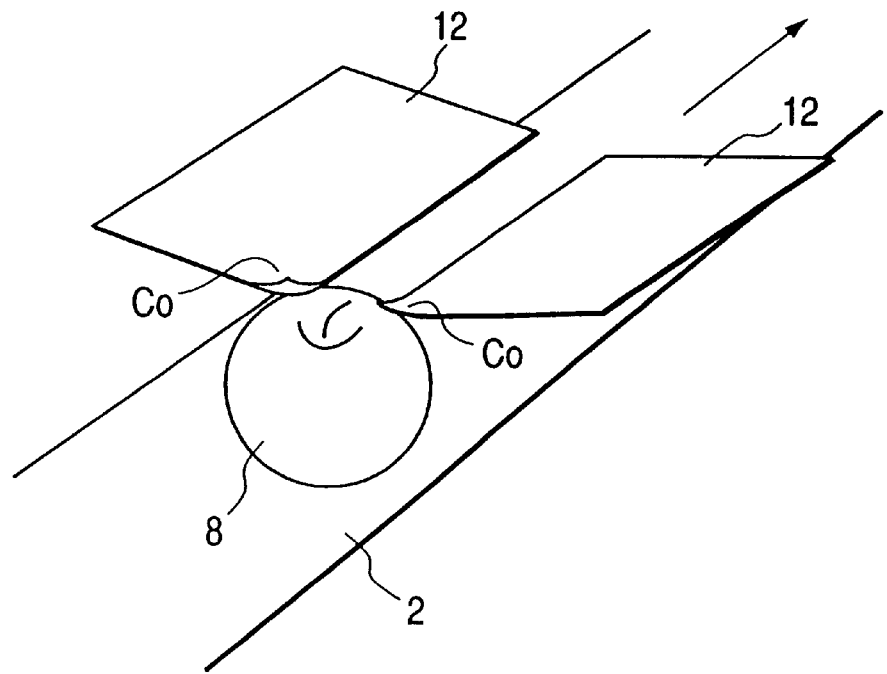
FIG. 26 is a perspective view to show the structure of shield plates according to a modification of the device of the ninth embodiment.

A modification of the ninth embodiment can also be constructed in such structure that the fruit or vegetable itself moving on the conveyor pushes the shield plates up, instead of the automatic adjustment of the position of the shield plates. An example of this structure is illustrated in FIG. 26. In this example, an upward curl (curve) $C_0$ is formed at each of corners opposed on the upstream side of the shield plates 312 and the shield plates 312 are arranged to be pushed up by the inspected object itself with the movement of the inspected object by the conveyor. In the case of this modification, the structure becomes simpler, because it obviates the need for the mechanism for detecting the size of the inspected object and the mechanism for adjusting the position of the shield plates in conjunction therewith.

The tenth embodiment of the present invention will be described next. The device of the tenth embodiment is characterized in that the stray light is intercepted by a tray fixed on the belt conveyor. Since the overall structure of the device of the tenth embodiment is similar to that of the sixth embodiment, the description thereof is omitted herein and only the part associated with the tray will be described below.

Figure 27A:
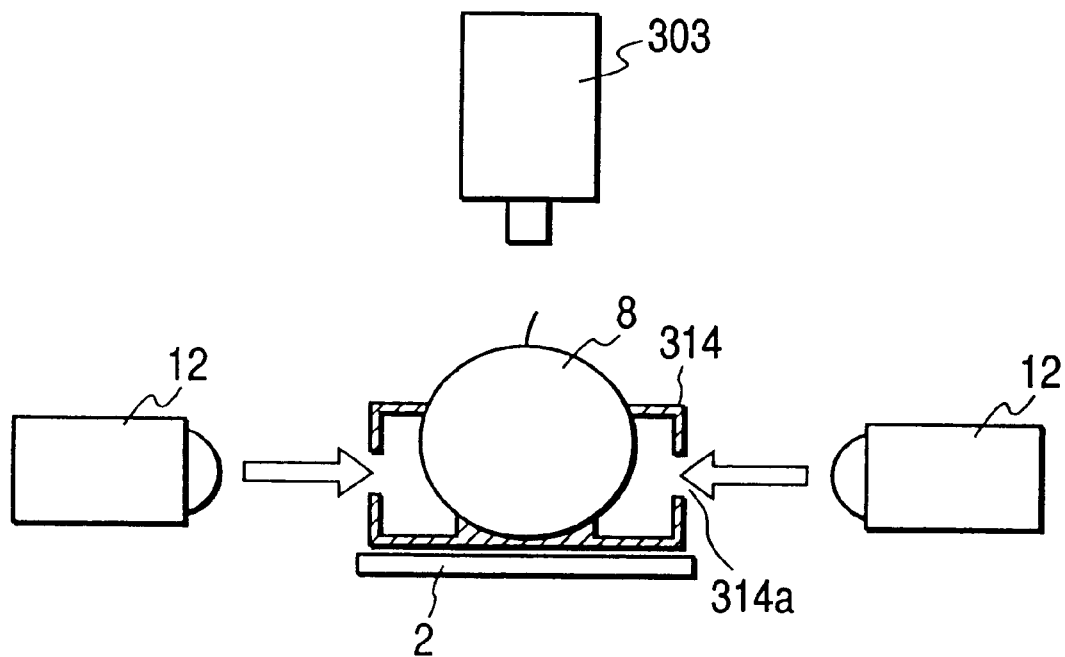
Figure 27B:
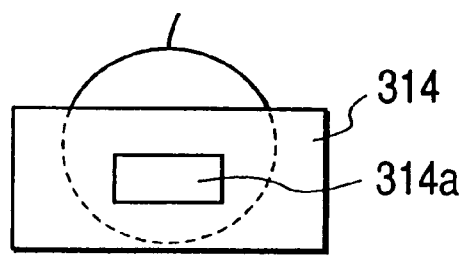

FIG. 27A and FIG. 27B are diagrams to show the schematic structure of the tray in the device of the tenth embodiment. FIG. 27A is a side view of the tray part in which the tray itself is illustrated in cross section. FIG. 27B is a side view from a direction perpendicular to FIG. 27A. As illustrated in the figures, the tray 314 is placed on the belt conveyor 2 and the inspected fruit or vegetable 8 is mounted on the tray 314 in the device of the present embodiment. A hole 314a is bored in each of side surfaces opposed in the transverse direction of the conveyor belt in the tray 314. As seen from FIG. 27A, the light from the light sources 12 travels through the holes 314a to irradiate the inspected fruit or vegetable 8. Since the light reflected by the surface of the fruit or vegetable is effectively intercepted by the tray 314, it is rarely incident to the light receiving element 303. There are a plurality of trays 314 placed on the belt conveyor.

The embodiments of the present invention were described above and it should be noted that the present invention is by no means intended to be limited to the details of these embodiments. For example, the embodiments employed the belt conveyor, but the conveying system can also be selected from a variety of other conveying devices.

The sixth to the tenth embodiments used the two light sources disposed on either side of the conveyance path, but the number of light sources may also be one or more than two. In the seventh to ninth embodiments, if the light source is provided on only one side of the belt conveyor, the shield plate on the other side can be omitted.

In the sixth to the tenth embodiments the light from the light sources is projected in the horizontal direction, but the light may also be projected in an inclined state diagonally from above or below. The embodiments are arranged to project the light in the direction perpendicular to the conveying direction by the belt conveyor, when seen from above, but it can also be projected in an inclined state.

Further, the halogen lamps were used as the light sources in the devices of the embodiments, but, without having to be limited to this, the light sources can also be selected from the other light sources that can emit the light in the wavelength region used in the measurement.

There are no restrictions on the kind and size of the fruits or vegetables as measured objects in the devices of the present invention and the present invention can also be applied to a variety of fruits or vegetables by properly arranging the size of the device and the number and light quantity of the light sources.

The internal qualities measured by the devices of the present invention include not only the typical examples of sugariness and acidity but also all other internal qualities of fruits or vegetables that can be measured by spectral analysis.

The eleventh embodiment of the present invention will be described next. Here, the same components as in the first embodiment will be omitted from the description herein and different portions will be described mainly.

Figure 28A:
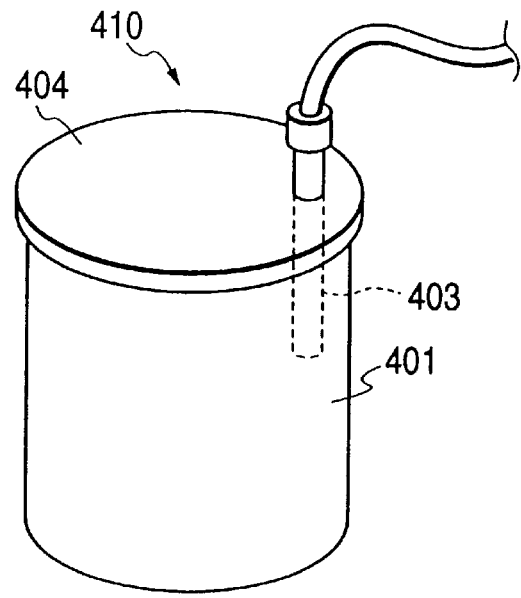
Figure 28B:
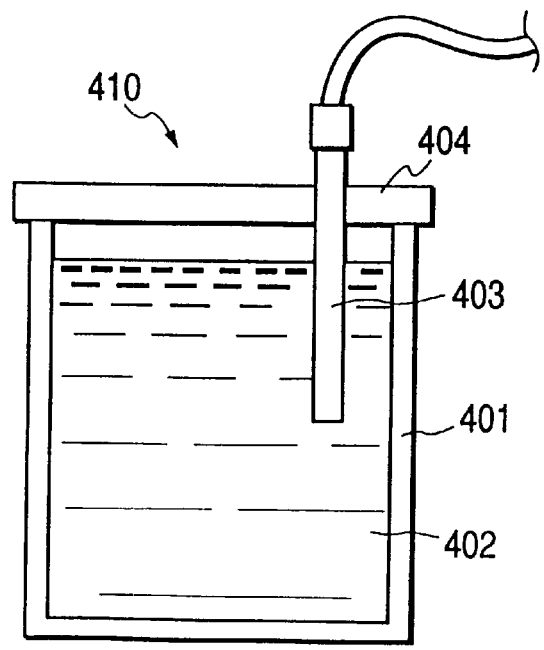

FIG. 28A and FIG. 28B are diagrams to show an artificial fruit or vegetable reference body 410 as an embodiment of the present invention, wherein FIG. 28A is a perspective view and FIG. 28B is a sectional view. This artificial fruit object is composed of a cylindrical glass vessel 401 having the diameter of 65 mm and the height of 80 mm and a light transmitting body 402 retained therein. The top surface of the vessel is also covered by a glass lid 404 to be closed hermetically. The light transmitting body is a material obtained by mixing cerium oxide having the size of 0.3 $\mu$m as a light scattering body in 1% citric acid aqueous solution to make it uniformly dispersed and making it gel with polyacrylamide gel. An amount of cerium oxide mixed is properly set according to the kind of the fruits or vegetables as inspected objects.

The artificial fruit object 410 of the present embodiment is equipped with a temperature measuring member (temperature measuring means) 403 using a thermistor or the like for measuring the temperature of the light transmitting body, inside the light transmitting body 402.

Described next is a method for correcting measured values of the measuring device for measuring the internal quality of the fruits or vegetables using the artificial fruit object 410. FIG. 29 is a diagram to show the structure around the measurement position of the fruit or vegetable measuring device. The measuring device has the belt conveyor 422 and the fruits or vegetables to be inspected (for example, oranges) placed on the belt conveyor 422 are successively fed to the measurement position. At the measurement position the light is projected to the inspected object from the light projecting device 420 composed of a light source 411, a stop 412, and a lens system 413. The light having passed through the inspected object is incident to a light receiving sensor 414. The light incident to the light receiving sensor is separated into a plurality of wavelength band channels and the spectral analysis thereof is carried out by a known method for checking the absorbance in each of the channels, thereby calculating the internal quality of the inspected fruit or vegetable, for example, the acidity thereof. Since this method itself is known, the description thereof is omitted herein.

The device is provided with the artificial fruit object 410 and the artificial fruit object 410 is arranged to be moved up and down at the measurement position by an unrepresented mechanism so as to be moved between a calibration position located between the light projecting system and the light receiving sensor and a normal position where the artificial fruit object 410 is retracted from the calibration position.

Figure 31:
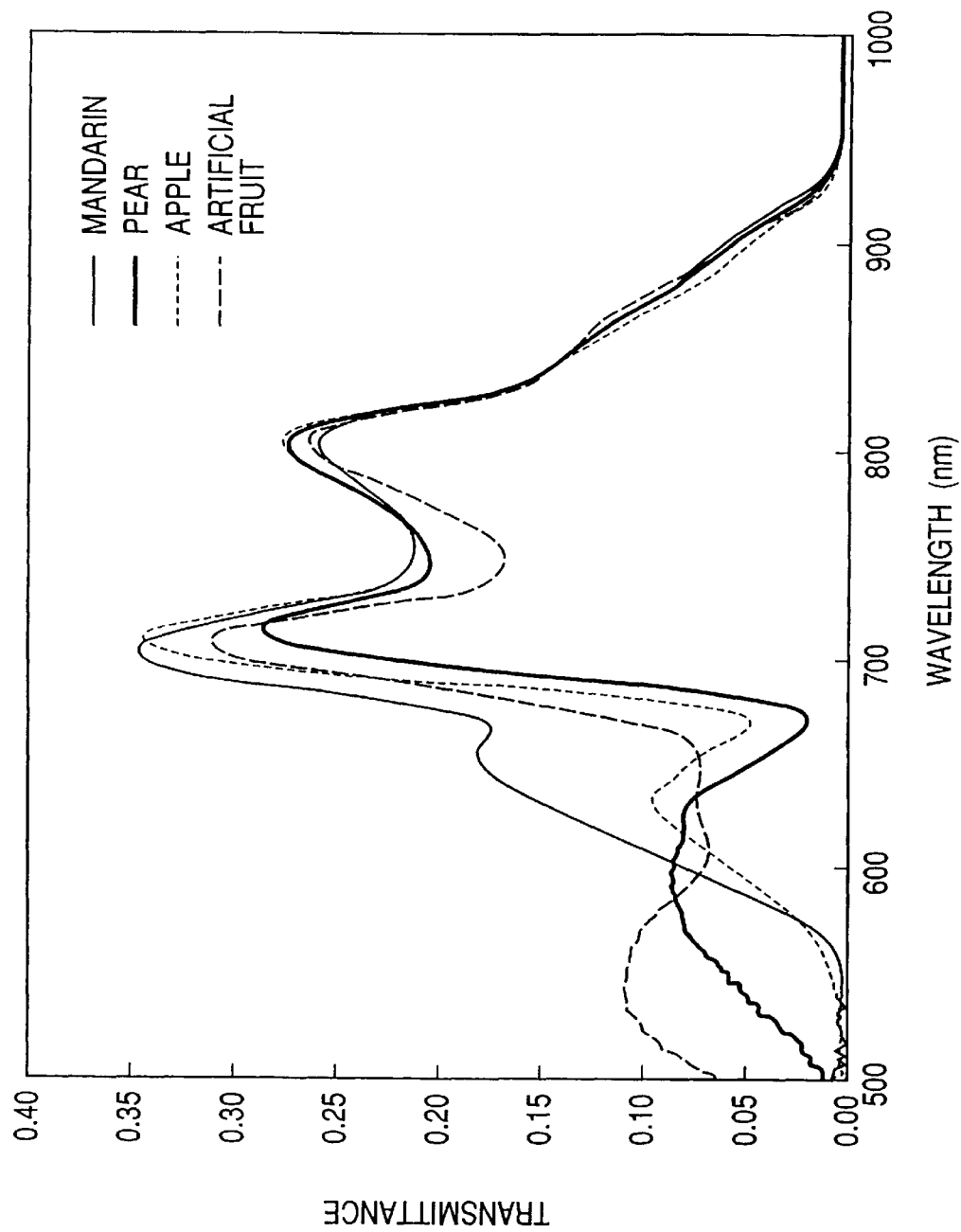
FIG. 31 is a diagram to show a spectrum of transmitted light through the artificial fruit reference body of the eleventh embodiment with comparison to spectra of transmitted light through actual fruits.

FIG. 31 shows the result of the measurement of the transmitted light spectrum of the artificial fruit object in the present embodiment. The same figure also shows the transmitted light spectra of real fruits, a mandarin orange, a pear, and an apple together with that of the artificial fruit object and it is seen from the figure that, particularly in the near-infrared region of the wavelengths above 810 nm, the spectral property of the artificial fruit object 410 follows the spectral properties of the real fruits well.

In the correction method and device for the measurement of the internal quality of the fruits or vegetables described above, the measured values of the fruits or vegetables are corrected with the correction value obtained using the single artificial fruit or vegetable reference body, whereas the following example illustrates a method and device for correction by use of a plurality of artificial fruit or vegetable reference bodies.

Figure 30:
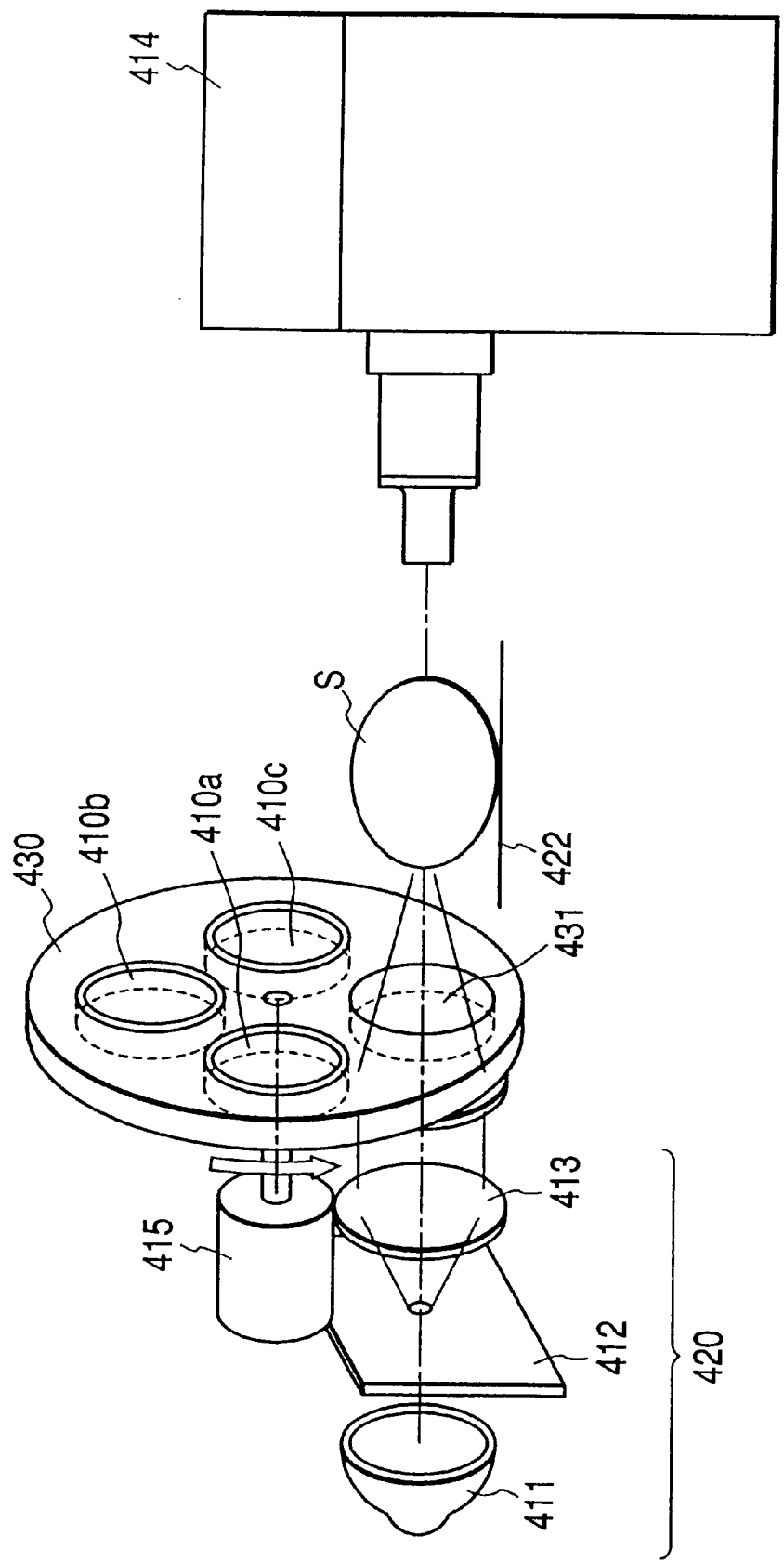
FIG. 30 is a perspective view to show the structure around the measurement position of a measuring device for measuring the internal quality of the fruit or vegetable using a plurality of artificial fruit objects.

An example of the device for performing the calibration with a plurality of artificial fruit objects is illustrated in FIG. 30. The device illustrated in FIG. 30 has a light projecting system 420 comprised of a halogen lamp light source 411, a stop 412, and a lens system 413, and a light receiving sensor 414, similar to the device of FIG. 29. This device further has a revolver 430 in which four holes are bored. Artificial fruit objects 410a, 410b, and 410c are fit in three holes out of the four holes of the revolver. Nothing is set in one rest hole. The three artificial fruit objects are made based on three types of solutions having different concentrations. Specifically, the solutions are citric acid solutions having the respective concentrations of 1%, 2%, and 3%. The three artificial fruit objects are made all in the equal fashion to each other except for the concentrations of citric acid. The revolver is driven by stepping motor 415 to set each of the artificial fruit objects in order at the measurement position during the correction operation, and the amount of transmitted light through each object is measured. During the normal measurement of the fruits or vegetables except for the period of the correction operation, the light from the light projecting system is projected through the through hole 431 to the inspected fruit or vegetable S.

In the device of the embodiment illustrated in FIG. 29 and described above the correction is carried out using the single artificial fruit object. Accordingly, the constant correction value is presented, irrespective of the acid concentrations, in the measurement of all the inspected fruits or vegetables. In contrast with it, the measurement is carried out with the reference bodies having the three different concentrations of citric acid in the device of the present embodiment. This is for carrying out the correction with higher accuracy with consideration to the concentrations of the inspected objects, because variations in the measured values of acidity due to the environmental change of the temperature or the like possibly differ according to the acid concentrations of the inspected objects.

In this embodiment correction values are obtained using the respective artificial fruit or vegetable reference bodies having the citric acid concentrations of 1%, 2%, and 3%, respectively, and the correction can be carried out according to the acid concentrations of the inspected objects, using these correction values. Therefore, the correction accuracy is enhanced more. Specifically, the correction is implemented by obtaining a concentration-correction value straight line approximately linearly connecting the correction values and carrying out the correction according to a concentration of each inspected object, based on the straight line.

The structure of the artificial fruit objects arranged in the revolver type in this device illustrated in FIG. 30 had never been able to be realized until the structure of the small (i.e., small in the length in the light transmission direction) artificial fruit objects was substantiated while adjusting the optical transmittances by use of the light scattering body as in the present invention.

The present invention was described above based on the embodiments thereof, but it should be noted that the present invention is by no means intended to be limited to the details of the embodiments.

For example, in either of the above embodiments the artificial fruit objects were mainly made of the aqueous solution of citric acid, but, without having to be limited to citric acid, the artificial fruit objects may also be made of a material selected from other acids and sugars or other aqueous solutions.

In the artificial fruit objects, the light diffusing body is mixed in the aqueous solution in order to attenuate the transmitted light. It can also be contemplated to adjust the transmittance by lowering the transmittance of the vessel instead of the addition of the light diffusing body.

The vessel of the artificial fruit objects was glass in the above examples, but the vessel may also be made of an optically transparent material among resins. The other structure, operation, and effects than above are the same as in the first embodiment.

The twelfth embodiment of the present invention will be described next. Here, the same components as in the first embodiment will be omitted from the description and different portions will be described mainly.

Figure 32A:
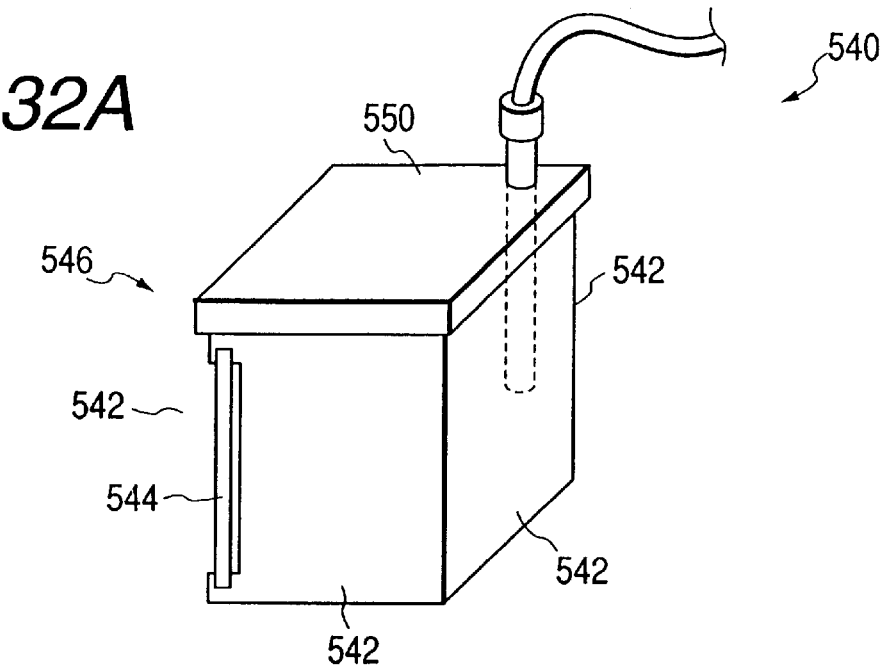
Figure 32B:
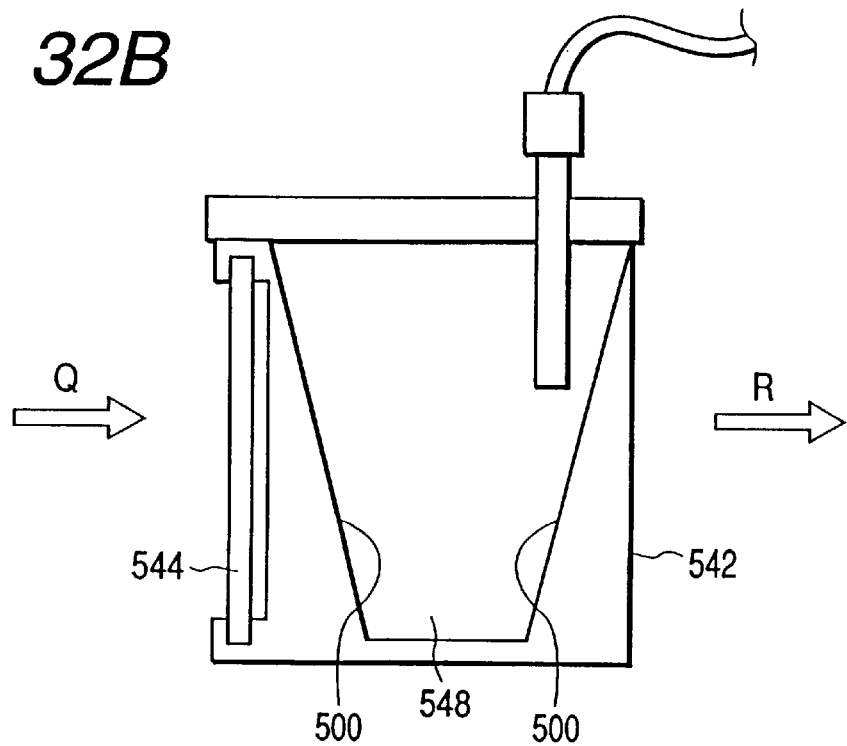

FIG. 32A and FIG. 32B are diagrams to show an artificial fruit or vegetable reference body (artificial fruit object) 540 of the present embodiment, wherein FIG. 32A is a perspective view and FIG. 32B is a sectional view. The present embodiment employs the artificial fruit object 540 in place of the artificial fruit object 40 of the first embodiment. This artificial fruit or vegetable reference body 540 is composed of a resin vessel 546 shaped in a rectangular parallelepiped having the height of 80 mm and the bottom 65 mm square and having a glass plate 544 in one surface out of its side surfaces 542, and a light transmitting body 548 retained therein. The top surface of the vessel is covered by a plastic lid 550 of the same material as the resin vessel 546, to be closed hermetically. At the side surface 542 of the resin vessel 546, the heat-resistant glass plate 544 is disposed in parallel to the side surface 542.

In the present embodiment, as illustrated in FIG. 32B, an inside surface 500 of the vessel 546 is inclined with respect to the vertical direction. This structure makes the distance between the side surfaces 542 narrower and narrower from top to bottom of the vessel 546 while thicknesses of the side surfaces 542 become larger from top to bottom of the vessel 546. When the light is projected from the direction Q and emitted in the direction R, the light projected to the upper part of the resin vessel 546 travels through thin portions of the side surfaces 542 and through a longer portion of the light transmitting body 548 to the outside, whereas the light projected to the lower part of the resin vessel 546 travels through thick portions of the side surfaces 542 and through a shorter portion of the light transmitting body 548 to the outside. This means that the light projected to the upper part of the resin vessel 546 is less affected by the side surfaces 542 than the light projected to the lower part and is thus transmitted at higher transmittances.

Described below is a method for correcting measured values by the internal quality measuring device of fruits or vegetables using this artificial fruit object 540. In the present embodiment the artificial fruit object 540 is arranged to be capable of being moved finely up and down within a range in which the light can be projected to either part of the side surface 542 of the resin vessel 546 at the calibration position 74 of FIG. 5.

In the present embodiment the resin vessel 546 forming the artificial fruit object 540 can transmit the light and varies transmission amounts of the light, depending upon its thicknesses. With the artificial fruit object 540 constructed as described, when the light is projected approximately normally to the side surface 542 of the vessel, amounts of emergent light from the opposite side surface 542 of the vessel differ depending upon the thicknesses of the side surfaces 542. Namely, when the light is projected in the same quantity to two portions having different thicknesses in the side surface 542, the amount of the transmitted light through the thicker portion is smaller than the amount of the transmitted light through the thinner portion, so that the thicker portion has a lower transmittance of light. The present embodiment, making use of this property, can change the projected portion in the side surface 542 among portions having different transmittances by moving the artificial fruit object 540 up and down, according to the kind of the inspected objects, a change of lot, or variations in the environment or the like.

As described above, the present invention permits the selection of the artificial fruit object 540 according to the change of the inspected object without changing the light projecting system and light receiving system and without rotating the artificial fruit object 540.

It should be noted that the present embodiment is just an example and the present invention is by no means intended to be limited to this.

The required shape of the inside surface 500 of the artificial fruit or vegetable reference body 540 is one changing the thicknesses of the side surfaces 542 in the vertical direction of the vessel 546, which can be realized, for example, by a quadrangular pyramid or a circular cone. The inside surface does not always have to be symmetric with respect to the vertical axis of the vessel 546 as long as it is inclined. Further, the inclination may also be made so as to decrease the thicknesses of the side surfaces 542 from the lid 550 side to the bottom side of the vessel 546.

The other structure, operation, and effects than above are the same as in the first embodiment.

The thirteenth embodiment of the present invention will be described next. Here, the same components as in the first embodiment or the twelfth embodiment will be omitted from the description and different portions will be described mainly.

Figure 33:
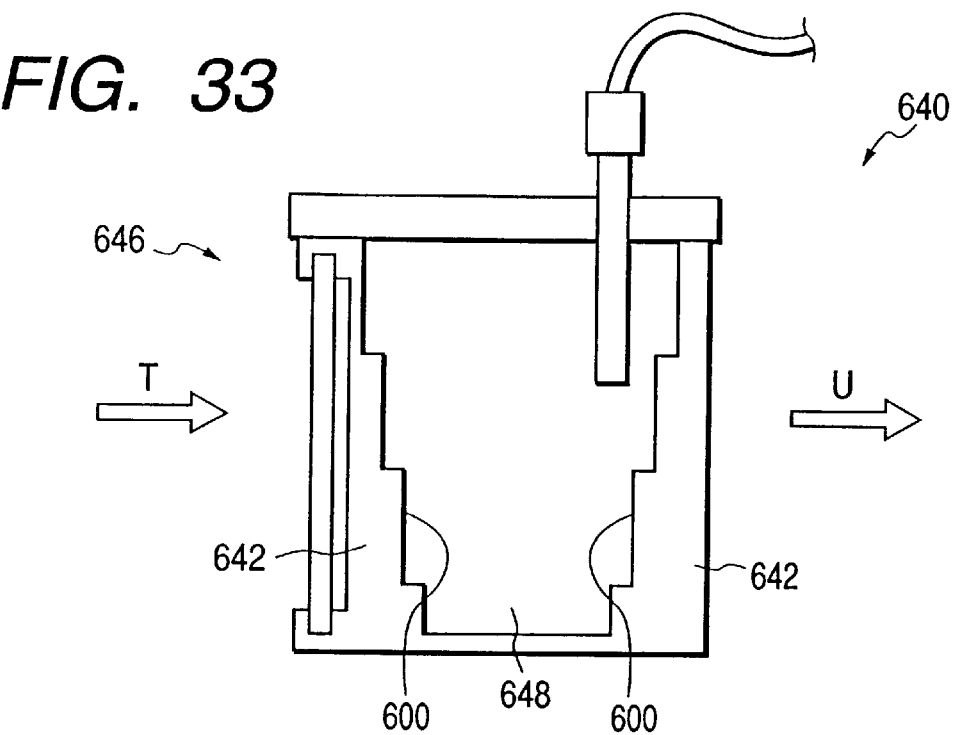
FIG. 33 is a sectional view to show another artificial fruit object as the thirteenth embodiment of the present invention.

FIG. 33 is a sectional view of an artificial fruit or vegetable reference body (artificial fruit object) 640 as the present embodiment. The present embodiment employs the artificial fruit object 640 in place of the artificial fruit object 40 of the first embodiment or the artificial fruit object 540 of the twelfth embodiment and, as illustrated in FIG. 33, the inside surface 600 of the vessel 646 is formed in a stepped shape in the vertical direction. This makes the distances between the side surfaces 642 stepwise narrower and narrower from top to bottom of the vessel 646, while the thicknesses of the side surfaces 642 become stepwise thicker from top to bottom of the vessel 646. When the light is projected from the direction T and emitted in the direction U, the light projected to the upper part of the resin vessel 646 travels through thin portions of the side surfaces 642 and through a longer portion of the light transmitting body 648 to the outside, while the light projected to the lower part of the resin vessel 646 travels through thick portions of the side surfaces 642 and a shorter portion of the light transmitting body 648 to the outside. Namely, the light projected to the upper part of the resin vessel 646 is less affected by the side surfaces 642 than the light projected to the lower part and is emitted at higher transmittances.

The other structure, operation, and effects than above are the same as in the first embodiment or the twelfth embodiment.

The fourteenth embodiment of the present invention will be described next. Here, the same components as in the first embodiment will be omitted from the description and different portions will be described mainly.

Figure 34:
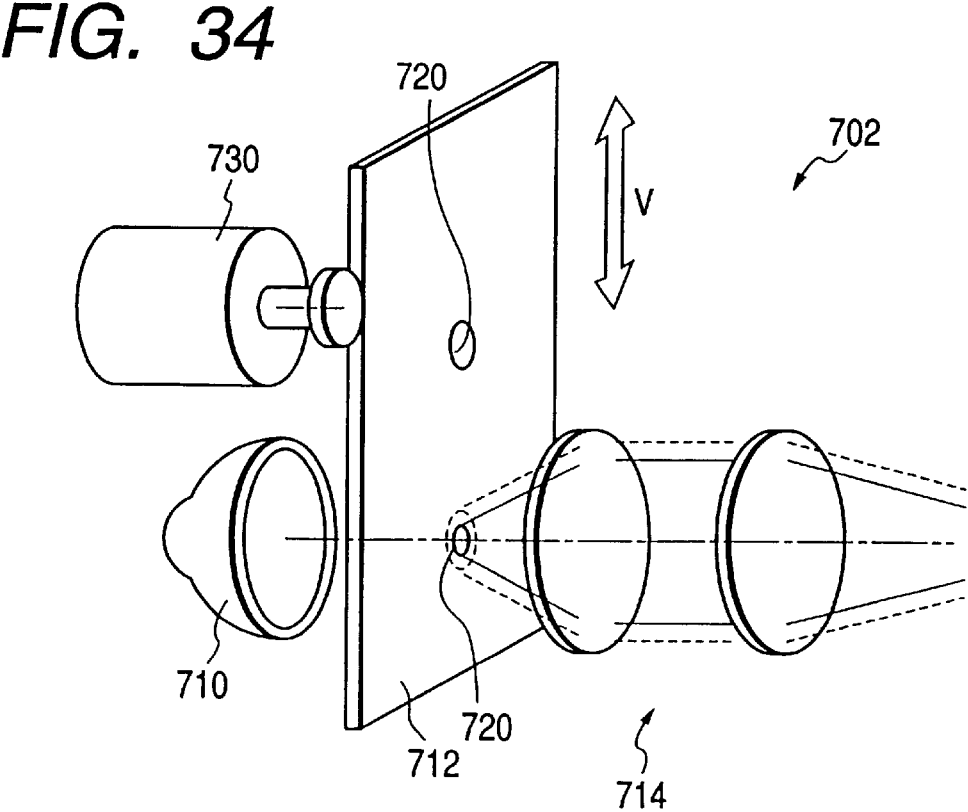
FIG. 34 is a perspective view to show the schematic structure of the projection optical system in the fourteenth embodiment of the present invention.

The present embodiment uses a shield plate 712 in place of the stop 66 of the first embodiment. FIG. 34 is a perspective view to show the structure of the projection optical system 702.

In the present embodiment the shield plate 712 has a plurality of, for example two, circular, small holes 720. These small holes 720 have respective diameters different from each other. When the light is projected in the same projection amount from the lamp 710 disposed behind the shield plate 712 to each small hole 720, light of an amount proportional to an aperture area of each small hole is emitted through each small hole 720 from the front surface of the shield plate 712. The shield plate 712 is arranged to be movable in the vertical directions V by motor 730 and there are a plurality of small holes 720 provided along the moving directions V. Therefore, a desired small hole 720 can be positioned on the optical axis of the lamp 710 and lens 714 by moving the shield plate 712 in the vertical direction V by the motor 730.

Selection of the small hole 720 is made based on the kind of the fruit or vegetable being the inspected object 8. Namely, for measuring the internal quality of a fruit or vegetable that is apt to transmit the light easily, a small hole having a small diameter is used to decrease the projection amount to the inspected object. On the other hand, in the case of a fruit or vegetable that is resistant to transmission of the light, a small hole having a large diameter is used to increase the projection amount to the inspected object. In this way, the amount of light emitted from the inspected object can be set so as to be not less than a fixed value, independent of the kind of the inspected object, by selecting a small hole 720 according to the kind of the inspected object to change the amount of light projected to the inspected object. This permits accurate measurement of the internal quality of the fruits or vegetables independent of the kinds of the inspected objects.

Examples of the measurement in the present embodiment will be described below.

A first example is the measurement of the internal quality of an orange apt to transmit the light readily. A small hole having a small diameter is selected out of those in the shied plate 712. In this case, the internal quality of the inspected object can be measured from the absorption spectrum thereof, because the amount of light emitted from the inspected object is sufficiently large though the projection amount to the inspected body is small.

A second example is the measurement of the internal quality of an apple resistant to transmission of the light. A small hole having a large diameter is selected from those 720 of the shield plate 712. In this case, the internal quality of the inspected object 8 can be measured from the absorption spectrum thereof, because the projection amount to the inspected object is large and, therefore, the amount of light emitted from the inspected object is sufficiently large.

The other measurement conditions than above are the same as in the case of the inspected object being the orange, and the internal quality of the inspected object can be measured from the absorption spectrum of the emitted light from the inspected object.

A modification of the present embodiment will be described below.

The number of small holes 720 in the shield plate 712 can be any number except for one.

In the present embodiment the shield plate 712 was arranged to be moved up or down in one way V and the small holes 720 were provided along the up or down direction V. The moving direction of the shield plate 712 does not always have to be limited to the vertical direction V; for example, the shield plate 712 can also be arranged to be movable in two ways, for example, in the vertical direction V and in a direction perpendicular to the vertical direction V within the plane including the shield plate 712. In this case, the small holes 720 can be formed at arbitrary positions in the shield plate 712 and a desired small hole 720 can be positioned on the optical axis 718 of the lamp 710 by moving the shield plate 712 in the aforementioned two directions.

The shape of the small holes does not always have to be circular.

The control of the amount of the light projected to the inspected object can also be made with filters, instead of the small holes formed in the shield plate as in the present embodiment.

The other structure, operation, and effects than above are the same as in the first embodiment.

Figure 35:
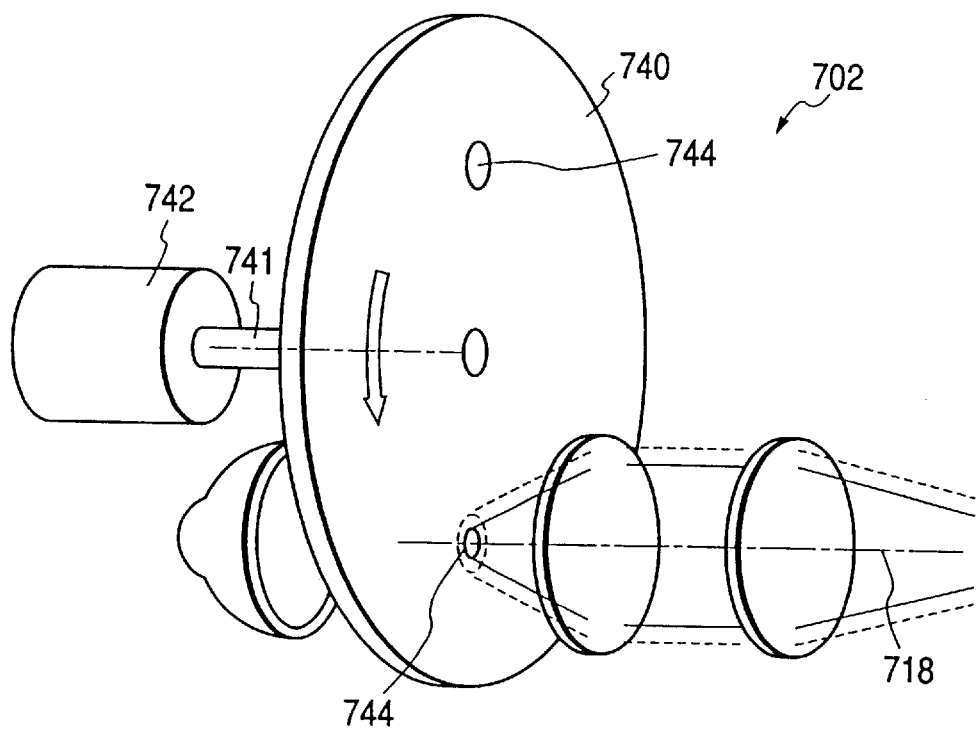
FIG. 35 is a perspective view to show the schematic structure of the projection optical system in the fifteenth embodiment of the present invention.

The fifteenth embodiment will be described below using FIG. 35. FIG. 35 is a perspective view to show the structure of the projection optical system 702 of the fifteenth embodiment.

In the present embodiment a circular shield plate 740 is placed in a plane normal to the optical axis 718 of the projection optical system 702. The shield plate 740 is rotated about shaft 741 by motor 742 connected to the shaft 741 extending normally from the center of the shield plate 740. In the shield plate 740 there are a plurality of, for example two, circular, small holes 744 having different diameters at positions an equal distance apart from the center of the shield plate 740. This structure permits selection of a small hole 744 according to the kind of the inspected object.

For measuring the internal quality of a fruit or vegetable apt to transmit the light easily, a small hole 744 having a small diameter is selected out of the small holes 744 in the shield plate 740. In this case, the internal quality of the inspected object can be measured from the absorption spectrum thereof, because the amount of light emitted from the inspected object is sufficiently large though the projection amount to the inspected object is small. In contrast with it, for measuring a fruit or vegetable resistant to transmission of the light, a small hole having a large diameter is selected out of the small holes in the shield plate 712. In this case, the internal quality of the inspected object can be measured from the absorption spectrum thereof, because the projection amount to the inspected object is large and thus the amount of light emitted from the inspected object is sufficiently large.

The other structure and operation than above are the same as in the fourteenth embodiment.

The sixteenth embodiment will be described next.

In the sixteenth embodiment there is one fruit or vegetable or are a plurality of fruits or vegetables conveyed on the conveyor. In the middle of the conveyor there are the projection optical system and the measuring section with the spectroscope, similar to those in the fourteenth embodiment, on either side of the conveyor. Further, the present embodiment is provided with a photoelectric sensor upstream of the measuring section in the conveyance direction or within the measuring section in the middle of the conveyor, so as to be capable of measuring the size of each fruit or vegetable on the conveyor.

In the structure of the present embodiment, the photoelectric sensor can detect the size of each fruit or vegetable, and the light from the lamp can be automatically projected to the equator part of the inspected object, irrespective of the size of the inspected object, by moving the projection optical system and spectroscope up and down according to the result of the detection to change the height thereof.

Therefore, the internal quality of the inspected objects conveyed continuously can be measured at high speed under the same conditions.

The other structure and operation than above are the same as in the first embodiment.

The seventeenth embodiment of the present invention will be described below referring to FIG. 36. Here, the description of the same components as in the first embodiment will be omitted and only different portions will be described herein.

Figure 36:
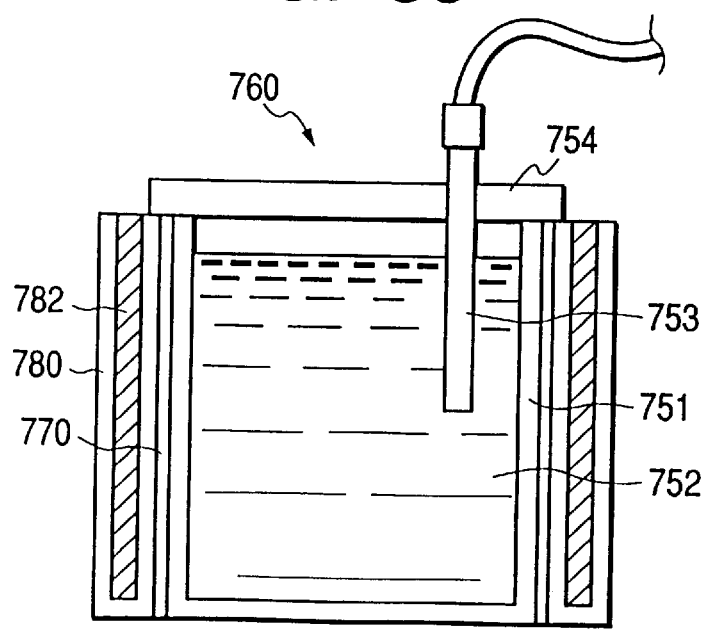
FIG. 36 is a sectional view to show an artificial fruit or vegetable reference body as the seventeenth embodiment of the present invention.
Figure 37:
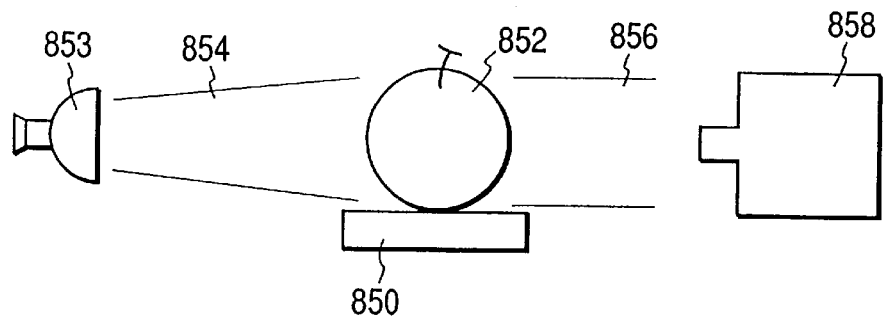
FIG. 37 is a schematic diagram to show the structure of a conventional example.
Figure 38:
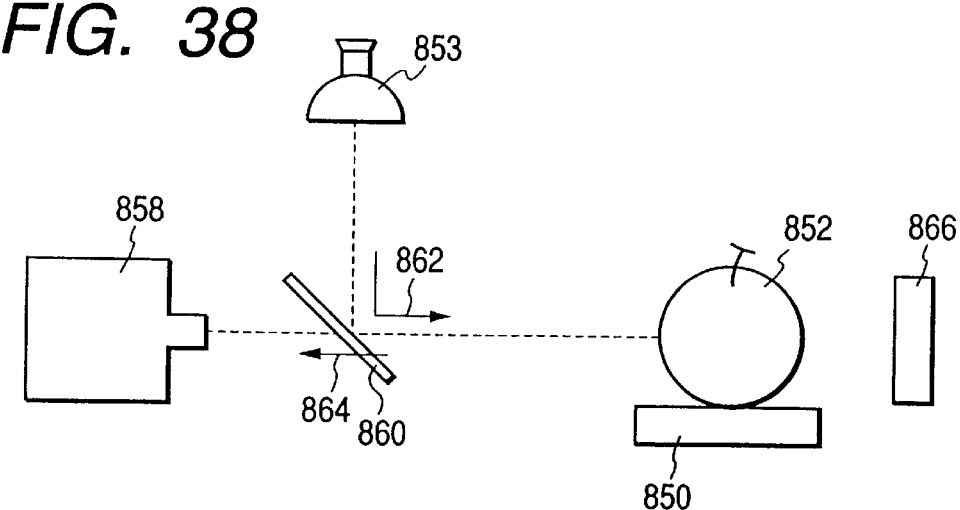
FIG. 38 is a schematic diagram to show the structure of another conventional example.
Figure 39:
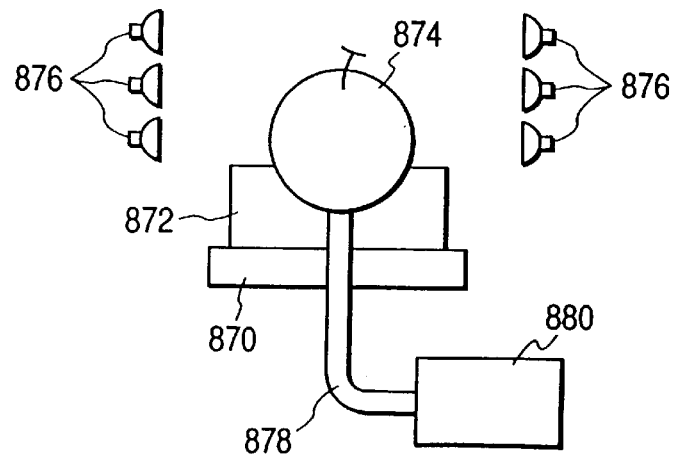
FIG. 39 is a schematic diagram to show the structure of still another conventional example.

FIG. 36 is a sectional view to show an artificial fruit or vegetable reference body 760 (artificial fruit object) as an embodiment of the present invention. This artificial fruit object 760 is composed of a cylindrical vinyl chloride vessel 751 having the diameter of 65 mm and the height of 80 mm, a light transmitting body 752 retained therein, and an adhesive tape 770 adhered to a side surface of the vinyl chloride vessel 751 as a light scattering layer. The top surface of the vessel is also covered by a vinyl chloride lid 754 to be closed hermetically.

In the present embodiment, the adhesive tape 770 is a resinous tape so that a light irradiated to the artificial fruit object 760 is scattered by the adhesive tape 770. The spectrum properties of the artificial fruit object 760 arranged as above follows the spectrum properties of the real fruits well.

Also, a heat-resistant glass 780 is provided around the side surface of the vessel 751 so as to surround the circumference of the adhesive tape 770 and to be parallel to the side surface of the vessel. The heat-resistant glass 780 is composed of two heat-resistant glass layers provided in parallel to the side surface of the vessel with gap 782 of about 10 mm, and the gap is filled by 1% citric acid aqueous solution. With such arrangement, heat-resistant property is improved from the case where only the heat-resistance is provided.

The light transmitting body 752 contained in the vessel 751 is composed of 1% citric acid aqueous solution as an acid aqueous solution. Further, the artificial fruit object 760 of the present embodiment is provided with a temperature measuring member (temperature measuring means) 753 using a thermistor or the like for measuring the temperature of the light transmitting body, inside the light transmitting body 752.

The present embodiment is just an example, so following modification can be effected.

The material of the vessel 751 can be glass, polyethylene, or polyfluoroethylene. The shape of the vessel 751 can be arbitrary shaped such as a rectangular parallelepiped.

The adhesive tape can include cellulose, so a paper tape can be used. Also, non-adhesive tape can be used. A polymer other than the resin can be applied. Further, the light scattering layer can be provided on the surface of the vessel 751 by coating, painting, spraying or dipping instead of the adhesive tape. It is also preferable to adhere only to an optical path portion of the light irradiated to the vessel 751.

The heat-resistant glass 780 can be arranged by one layer of glass to fill the aqueous solution between the side surface of the vessel and the glass layer. The heat-resistant glass 780 can be composed of three or more glass layers. Also, the gap 782 can be formed in one layer of the heat-resistant glass. It is also preferable to provide only to an optical path portion of the light irradiated to the vessel 751. A light transmitting heat-resistant material can be used instead of the heat-resistant glass 780.

An acid aqueous solution other than 1% citric acid aqueous solution, a sugar aqueous solution or water can be used for the gap 782. Also, it is preferable to flow the solution for improving heat-resistant property. Further, it is preferable to add a light scattering body into the solution in the gap 782, and, in this arrangement, the adhesive tape 770 can be omitted.

The other structure, operation, and effects than above are the same as in the first embodiment.

The present invention provides the apparatus for measuring the inspected objects arranged in the longitudinal direction of the belt of the belt conveyor, wherein a portion without an inspected object can be detected in the longitudinal direction and the calibration of the apparatus can be carried out at this portion. Therefore, the calibration can be carried out not only before the start of the measurement but also at a desired time after the start of the measurement. The measurement is not suspended for the calibration. The internal quality of the fruits or vegetables can be measured accurately while the calibration of the apparatus is carried out without interrupting the measurement accordingly.

According to the correction method of the present invention, an error due to the environmental change in the measurement of the internal quality of fruits or vegetables can be corrected using the reference body with variability of the absorption spectrum according to the environmental change and similar to the real inspected fruits or vegetables. The correction method is effective particularly against changes of the ambient temperature.

This obviates the need for the temperature control (management) of the apparatus or the ambient environment, thus reducing the cost thereof.

As described with FIG. 7, since the artificial fruit or vegetable reference body and the correction method using it according to the present invention also have the adequate follow-up property against variations in states of the light source, the measurement can also be started immediately after on of the light source without the need for waiting for stabilization of the light source, thus enhancing the measurement efficiency.

When the artificial fruit object is provided with the temperature measuring means for monitoring the temperature of the transmitting body of the artificial fruit object, such as the thermistor, even if there is a difference between the temperatures of the artificial fruit object and the inspected fruit or vegetable, correction can be made with consideration thereto.

More accurate correction can also be made by carrying out the correction with a plurality of artificial fruit objects having respective concentrations.

When the light diffusing body is mixed in the aqueous solution in the artificial fruit or vegetable reference body of the present invention, the artificial fruit or vegetable reference body can have an appropriate value of light transmittance. The transmittance can be adjusted readily by adjusting the concentration of the light diffusing body.

When the gelling agent is added to the aqueous solution in the artificial fruit object of the present invention to make the solution gel, the artificial fruit object can be stabilized without sedimentation of the light diffusing body.

The measuring device of the internal quality of fruits or vegetables according to the present invention can measure the internal quality corrected for fluctuations of the absorption spectrum of the fruits or vegetables due to the environmental change, because it is provided with the artificial fruit or vegetable reference body.

When the device is provided with a plurality of artificial fruit or vegetable reference bodies, the reference bodies having respective different concentrations, more accurate correction can be realized according to the concentration of each inspected fruit or vegetable.

In the present invention, the light can be projected to the vicinity of the equator part of each inspected object, irrespective of the size of the inspected object. Therefore, the internal quality of each inspected object can be measured under the same conditions, thereby enhancing the reliability of measured data. The amount of the projected light to the fruit or vegetable can be varied according to the kind of the fruit or vegetable being the inspected object. Since the absorption spectrum can be measured for the inspected objects resistant to transmission of the light, the internal quality of the fruits or vegetables can be measured more accurately, independent of the kind of the inspected objects, accordingly.

In the present invention the position of the inspected object on the moving means is detected on the upstream side of the measurement position in the moving path of the inspected object and the moving amount of the moving means is monitored, whereby the measurement can be carried out when the inspected object is correctly located at the measurement position, thereby enhancing the measurement accuracy.

The position of the inspected object on the moving means is detected both upstream and downstream of the measurement position in the moving path of the inspected object and an event with a deviation between them is determined as a measurement error. Therefore, an inspected object with doubtful measurement accuracy can be recognized and it is also possible to apply the process for re-measuring the doubtful inspected object, which assures the measurement with higher reliability.

The present invention can provide the apparatus for measuring the inspected objects arranged in the longitudinal direction of the belt conveyor, wherein a portion without an inspected object can be measured in the longitudinal direction and the calibration of the apparatus can be carried out at this portion. Therefore, the calibration can be carried out not only before the start of the measurement but also at a desired time after the start of the measurement, and the measurement is not interrupted by the calibration. The internal quality of the fruit or vegetable can be measured accurately by carrying out the calibration of the apparatus at an arbitrary time without interruption of the measurement accordingly.

Since the device of the present invention is arranged to project the light from the side to the inspected object and receive the transmitted light above the inspected object, it can secure the amount of the transmitted light equivalent to those of the conventional devices of the lower reception type while being free of the restrictions on the conveying system as forced in the lower reception type. Therefore, the device of the present invention also permits the random measurement with the inspected objects being supplied at random onto the conveyor, so as to enable continuous measurement at high efficiency. Since the light receiving means can be installed in the space above the device where there is no interfering object, this facilitates assembling and maintenance.

When the shield plate is disposed beside the inspected object located at the measurement position and at the position lower than the height of the inspected object and higher than the projection position of the light from the light projecting means onto the inspected object, the light receiving means can be effectively shielded from the stray light.

In the configuration in which the light projecting means is positioned on the both sides of the moving means, if there are a pair of shield plates provided on the both sides and the separation between the two shield plates is adjustable, the clearance between the shield plates and the inspected object can be adjusted according to the measured object without interference therewith, so as to achieve effective shielding. Further, when the device is provided with the lateral diameter measuring means disposed upstream of the measurement position in the moving path and arranged to measure the lateral diameter of the inspected object, and the adjusting means for adjusting the separation between the shield plates, based on the output of the lateral diameter measuring means, it becomes possible to adjust the shield plates according to the sizes of the individual inspected objects.

In the device of the present invention, the stray light can be effectively intercepted when the shield plates are positioned above the height of the inspected object located at the measurement position. Further, when the device is provided with the height measuring means disposed upstream of the predetermined position in the moving path and arranged to measure the height of the inspected object, and the adjusting means for adjusting the height of the shield plates, based on the output of the height measuring means, the shield plates can be set at the position where effective shielding can be achieved without interference with the inspected object, according to the heights of the individual inspected objects.

When the device of the present invention is provided with the size measuring means disposed upstream of the measurement position in the moving path and arranged to measure at least one of the height and the lateral diameter of the inspected object, the shield plate for shielding the light receiving means from the light directly projected from the light projecting means and from the light reflected by the surface of the inspected object, the shield plate being disposed near the inspected object at the measurement position and being capable of being pivoted about the predetermined horizontal axis, and the adjusting means for adjusting the angular position about the horizontal axis of the shield plate, based on the output from the size measuring means, so as to decrease the gap between the shield plate and the inspected object at the predetermined position, effective shielding can be achieved according to the size of each inspected object.

When the device of the present invention is provided with the shield plate for shielding the light receiving means from the light directly projected from the light projecting means and from the light reflected by the surface of the inspected object, the shield plate being capable of being pivoted about the predetermined horizontal axis, the shield plate being pushed up by the inspected object to be pivoted about the horizontal axis as the inspected object is moved by the moving means to approach the predetermined position and the shield plate shielding the light receiving means from the light while being in contact with the inspected object when the inspected object is located at the predetermined position, effective shielding can be achieved by the simple structure. In this case, if the shield plate is provided with the upward curl for allowing the shield plate to be moved up when it touches the inspected object, at the corner on the upstream side of the moving path in the shield plate and on the contact side with the inspected object, the shield plate can be pushed up on a smooth basis by the inspected object without being caught by the inspected object.

When the device of the present invention is provided with the tray fixed on the moving means and arranged to accommodate the inspected object, the tray covering at least part of the inspected object accommodated therein and having the aperture opening so as to let the light from the light projecting means reach the inspected object, the stray light can be intercepted effectively.

What is claimed is:

1. An internal quality measuring apparatus for measuring an internal quality of an object, said measuring comprising:
    conveying means for continuously conveying an object;
    detecting means for detecting a position of the object mounted on said conveying means;
    light projecting means for projecting measurement light to the object;
    light receiving means for receiving light having been transmitted through the object;
    analyzing means for analyzing the internal quality of the object with the light received by said light receiving means; and
    reference body interposing means for interposing a reference body having a predetermined optical property in an optical path between said light projecting means and light receiving means, based on a signal from said detecting means;
    wherein said analyzing means compares light received with the reference body being interposed, with reference data preliminarily stored, and corrects a result of the analysis, based thereon.

2. The internal quality measuring apparatus according to claim 1, wherein the reference body is an optical filter having a specific optical property.

3. The internal quality measuring apparatus according to claim 1, wherein the reference body is a pseudo-object member.

4. The internal quality measuring apparatus according to claim 1, further comprising shield means for intercepting the light incident to said light receiving means,
    wherein while it is determined based on the detection by said detecting means that a spacing between objects on said conveying means is less than a predetermined value, said reference body interposing means allows the light from said light projecting means to be projected onto the object without intervention of the reference body, so as to allow said light receiving means to measure the light having been transmitted through the object; and
    wherein when it is determined based on the detection by said detecting means that the spacing between the objects on said conveying means is not less than the predetermined value, said reference body interposing means interposes the reference body in the optical path between said light projecting means and said light receiving means, so as to adjust an amount of light incident to said light receiving means and allow said light receiving means to measure the amount of the light thus adjusted;
    said measuring device further comprising:
    arithmetic operation means for correcting a result of the measurement by said light receiving means, based on a result of measurement by said light receiving means when the amount of the incident light is controlled by said reference body interposing means and a result of measurement by said light receiving means when the incident light is intercepted by said shield means.

5. The internal quality measuring apparatus according to claim 4, wherein when it is determined based on the detection by said detecting means that the spacing between the objects on said conveying means is not less than the predetermined value, reference body interposing means adjust the amount of the light incident to said light receiving means, said light receiving means measures the amount of the light thus adjusted, thereafter further said shield means intercepts the light incident to said light receiving means, and said light receiving means measures the amount of the light in this state; or said shield means intercept the light incident to said light receiving means, said light receiving means measures the amount of the light in this state, thereafter the intercepting state of the light incident to said light receiving means by said shield means is released, said reference body interposing means adjusts the amount of the light incident to said light receiving means, and said light receiving means measure the amount of the light thus adjusted.

6. The internal quality measuring apparatus according to claim 3, wherein said pseudo-object member comprises a transparent vessel and a light transmitting body comprised of an aqueous solution retained in said vessel.

7. The internal quality measuring apparatus according to claim 6, wherein said light transmitting body is comprised of a light scattering body mixed in the aqueous solution.

8. The internal quality measuring apparatus according to claim 7, wherein at least one side surface out of side surfaces of said transparent vessel has a thickness different from that of the other side surfaces.

9. The internal quality measuring apparatus according to claim 7, wherein thicknesses of the side surfaces opposed to each other out of the side surfaces of said transparent vessel are equal and thicknesses of the side surfaces adjacent to each other are different from each other.

10. The internal quality measuring apparatus according to claim 6, wherein side surfaces of said transparent vessel have a same thickness.

11. The internal quality measuring apparatus according to claim 6 or 7, wherein said transparent vessel includes glass.

12. The internal quality measuring apparatus according to claim 6 or 7, wherein said transparent vessel includes vinyl chloride.

13. The internal quality measuring apparatus according to claim 6 or 7, wherein said transparent vessel contains polyethylene.

14. The internal quality measuring apparatus according to claim 6 or 7, wherein said transparent vessel contains polyfluoroethylene.

15. The internal quality measuring apparatus according to claim 14, wherein said transparent vessel contains graphite.

16. The internal quality measuring apparatus according to claim 6, wherein at least one side surface of said transparent vessel is provided with a light scattering layer.

17. The internal quality measuring apparatus according to claim 16, wherein said light scattering layer includes resin.

18. The internal quality measuring apparatus according to claim 16, wherein said light scattering layer includes cellulose.

19. The internal quality measuring apparatus according to claim 17 or 18, wherein said light scattering layer is an adhesive tape.

20. The internal quality measuring apparatus according to claim 17 or 18, wherein said light scattering layer is formed by coating.

21. The internal quality measuring apparatus according to claim 6, wherein at least one side surface of said transparent vessel is provided with a heat-resistant glass plate.

22. The internal quality measuring apparatus according to claim 6, wherein at least one side surface of said transparent vessel is provided with a heat-resistant glass plate.

23. The internal quality measuring apparatus according to claim 21 or 22, wherein the heat-resistant glass plate includes plural heat-resistant glass layers, and a water layer is provided in at least one of gaps between the heat-resistant glass layers.

24. The internal quality measuring apparatus according to claim 21 or 22, wherein the heat-resistant glass plate includes plural heat-resistant glass layers, and an acid aqueous solution layer is provided in at least one of gaps between the heat-resistant glass layers.

25. The internal quality measuring apparatus according to claim 21 or 22, wherein the heat-resistant glass plate includes plural heat-resistant glass layers, and an sugar aqueous solution layer is provided in at least one of gaps between the heat-resistant glass layers.

26. The internal quality measuring apparatus according to claim 21, wherein a water layer is provided between said transparent vessel and the heat-resistant glass plate.

27. The internal quality measuring apparatus according to claim 21, wherein an acid aqueous solution layer is provided between said transparent vessel and the heat-resistant glass plate.

28. The internal quality measuring apparatus according to claim 21, wherein a sugar aqueous solution layer is provided between said transparent vessel and the heat-resistant glass plate.

29. The internal quality measuring apparatus according to claim 6 or 7, wherein said transparent vessel is rotatable about an axis being parallel to a direction of a height of the transparent vessel and passing a center of a bottom surface thereof.

30. The internal quality measuring apparatus according to claim 6 or 7, wherein said transparent vessel is rotatable about an axis parallel to a direction of a height of the transparent vessel.

31. The internal quality measuring apparatus according to claim 6 or 7, wherein said transparent vessel is rotatable about an axis that is horizontal and normal to an optical axis of the measurement light projected from said light projecting means.

32. The internal quality measuring apparatus according to claim 3, wherein said pseudo-object member comprises a transparent vessel and a light transmitting body retained in the vessel, said light transmitting body being a substance obtained by dispersing a light scattering body in an aqueous solution and adding a gelling agent thereto to make the solution gel.

33. The internal quality measuring apparatus according to claim 6 or 7, wherein said pseudo-object member comprises temperature measuring means for measuring a temperature of said light transmitting body.

34. The internal quality measuring apparatus according to claim 6 or 7, wherein said aqueous solution is an aqueous solution of an acid.

35. The internal quality measuring apparatus according to claim 34, wherein said acid is citric acid.

36. The internal quality measuring apparatus according to claim 6 or 7, wherein said aqueous solution is an aqueous solution of a sugar.

37. The internal quality measuring apparatus according to claim 36, wherein said sugar is cane sugar.

38. The internal quality measuring apparatus according to claim 7, wherein the light scattering body is fine powder having a floating property.

39. The internal quality measuring apparatus according to claim 7, wherein the light scattering body is colloidal particles.

40. The internal quality measuring apparatus according to claim 38 or 39, wherein the light scattering body is cerium oxide.

41. The internal quality measuring apparatus according to claim 38 or 39, wherein the light scattering body is titanium oxide.

42. The internal quality measuring apparatus according to claim 6,
wherein said light projecting means projects light toward the object at a predetermined position in a moving path of the object by the conveying means, and
light receiving means is disposed near said predetermined position and receives light emitted from the object located at said predetermined position, and
the pseudo-object member is set at said predetermined position during a correction operation, to correct measurement of the internal quality by using the pseudo-object member.

43. The internal quality measuring apparatus according to claim 42, further comprising moving up-and-down means for moving said pseudo-object member up and down between a down position where said pseudo-object member is located at said predetermined position and an up position where the pseudo-object member is retracted from said predetermined position.

44. The internal quality measuring apparatus according to claim 6 or 7, wherein the reference body includes a plurality of pseudo-object members, wherein concentrations of said aqueous solution in said plurality of pseudo-object members are different from each other, and wherein measurement of the internal quality of the object is corrected using the plurality of pseudo-object members.

45. The internal quality measuring apparatus according to claim 44, wherein said plurality of pseudo-object members is mounted on a revolver member rotatable about a predetermined axis and wherein during a correction operation of the apparatus the pseudo-object members are positioned in order between said light projecting means and said light receiving means with rotation of said revolver member.

46. The internal quality measuring apparatus according to claim 45, wherein said revolver member has a through hole and during normal measurement except for said correction operation the light from said light projecting means is projected through the through hole to the object.

47. The internal quality measuring apparatus according to claim 1, further comprising:
projection light amount control means for controlling a projection light amount according to a kind of the object; and
position control means for controlling locations of said light projecting means, said conveying means, and said light receiving means, according to a size of the object.

48. The internal quality measuring apparatus according to claim 47, wherein said projection light amount control means comprises a stop and a size of an aperture of said stop is varied according to the size of the object.

49. The internal quality measuring apparatus according to claim 48, wherein said projection light amount control means comprises a shield plate having a plurality of small holes and shield plate moving means for moving said shield plate, and
wherein one of said small holes is located by said shield plate moving means on an optical axis of said light projecting means and between said light projecting means and the object, according to the size of the object.

50. The internal quality measuring apparatus according to claim 49, wherein said shield plate is of a rectangular shape, a plurality of small holes are provided on an arbitrary straight line within a surface of the shield plate, and said shield plate is arranged to be moved on the straight line by said shield plate moving means.

51. The internal quality measuring apparatus according to claim 49, wherein said shield plate is of a circular shape, a plurality of the small holes are provided at positions an equal distance apart from the center of the circle within a surface of the shield plate, and said shield plate is arranged to be rotated about the center by said shield plate moving means.

52. The internal quality measuring apparatus according to claim 47, further comprising diameter detecting means for detecting a diameter of the object,
wherein said light projecting means projects the light to a region around an equator part of the object conveyed while said position control means controls the locations of said light projecting means, said conveying means, and said light receiving means, based on a result of the detection of the diameter by said diameter detecting means.

53. The internal quality measuring apparatus according to claim 1, further comprising:
upstream detecting means disposed upstream of said light receiving means and arranged to detect a position of the object on said conveying means, in a conveyance path by said conveying means;
monitor means for monitoring a moving amount of said conveying means; and
control means for performing such a control that the light receiving means receives the light when said object on the conveying means passes a light receiving position of said light receiving means, based on outputs from said upstream detecting means and said monitor means.

54. The internal quality measuring apparatus according to claim 53, wherein said upstream detecting means detects a lateral diameter in a conveying direction of the object and wherein said control means calculates a center position in the conveying direction of the object, based on the lateral diameter detected and said control means performs such a control that the light receiving means receives the light when the center of the object passes the light receiving position of the light receiving means.

55. The internal quality measuring apparatus according to claim 53, further comprising:
downstream detecting means disposed downstream of said light receiving means in said conveyance path and arranged to detect a position of the object on said conveying means; and
error determining means for comparing the position of the object on the conveying means, detected by said upstream detecting means, with the position of the same object on the conveying means, detected by said downstream detecting means, and for determining that a measurement error was made, when there is a deviation between the two positions.

56. The internal quality measuring apparatus according to claim 54, further comprising:
downstream detecting means disposed downstream of said light receiving means in said conveyance path and arranged to detect a position of the object on said conveying means; and
error determining means for comparing the position of the object on the conveying means, detected by said upstream detecting means, with the position of the same object on the conveying means, detected by said downstream detecting means, and for determining that a measurement error was made, when there is a deviation between the two positions.

57. The internal quality measuring apparatus according to claim 54, further comprising:

downstream detecting means disposed downstream of said light receiving means in said conveyance path and arranged to detect a lateral diameter of said object in the conveying direction; and error determining means for comparing a lateral diameter of the object in the conveying direction, detected by said upstream detecting means, with a lateral direction of the object in the moving direction, detected by said downstream detecting means, and for determining that a measurement error was made, when there is a deviation between the two lateral diameters.

58. The internal quality measuring apparatus according to claim 55, further comprising classifying means for classifying an object with which said error determining means determined that a measurement error was made, as an object to be measured again.

59. The internal quality measuring apparatus according to claim 56, further comprising classifying means for classifying an object with which said error determining means determined that a measurement error was made, as an object to be measured again.

60. The internal quality measuring apparatus according to claim 57, further comprising classifying means for classifying an object with which said error determining means determined that a measurement error was made, as an object to be measured again.

61. The internal quality measuring apparatus according to claim 1, further comprising:

a first optical fiber having one end located at a position where the light projected from said light projecting means can be received directly and the other end connected to said light receiving means, said first optical fiber receiving the light from said light projecting means without intervention of the object;

light amount adjusting means disposed at the end or in the middle of an optical path of said first optical fiber and arranged to adjust an amount of light passing through said first optical fiber;

first shield means disposed at the end or in the middle of the optical path of said first optical fiber and arranged to intercept the light passing through said first optical fiber;

a second optical fiber having one end located at a position where the light emitted from the object can be received and the other end connected to said light receiving means, said second optical fiber receiving the light having been transmitted by the object;

second shield means disposed at the end or in the middle of an optical path of said second optical fiber and arranged to intercept light passing through said second optical fiber; and control means for controlling operations of said first shield means and said second shield means, based on the result of the detection by said detecting means;

wherein while it is determined based on the detection by said detecting means that a spacing between objects on said conveying means is less than a predetermined value, said control means makes said first shield means shield said first optical fiber and makes said light receiving means measure the light incident thereto from said second optical fiber;

wherein when it is determined based on the detection by said detecting means that the spacing between the objects on said conveying means is not less than the predetermined value, said control means makes said second shield means shield said second optical fiber and makes said light receiving means measure the light incident thereto from said first optical fiber through said light amount adjusting means;

said measuring device further comprising:

arithmetic operation means for correcting a result of the measurement by said light receiving means, based on a result of measurement by said light receiving means when the amount of the incident light is controlled by said control means and a result of measurement by said light receiving means when said shield means intercepts the incident light.

62. The internal quality measuring apparatus according to claim 61, further comprising measuring means for making said second shield means shield said second optical fiber at an arbitrary time, irrespective of the result of the detection by said detecting means, and making said light receiving means measure the light incident thereto from said first optical fiber through said light amount adjusting means.

63. The internal quality measuring apparatus according to claim 62, wherein when it is determined based on the detection by said detecting means that the spacing between the objects on said conveying means is not less than the predetermined value, said second shield means is made to shield said second optical fiber, said light receiving means is made to measure the light incident thereto from said first optical fiber through said light amount adjusting means, thereafter said first shield means is further made to shield said first optical fiber, and said light receiving means is made to measure the light with said first optical fiber and said second optical fiber being in a shielded state; or said first shield means and said second shield means are made to shield said first optical fiber and said second optical fiber, said light receiving means is made to measure the light with said first optical fiber and said second optical fiber being in the shielded state, thereafter said first shield means is opened to open said first optical fiber, and said light receiving means is made to measure the light incident thereto from said first optical fiber through said light amount adjusting means.

64. The internal quality measuring apparatus according to claim 1, wherein said light projecting means projects the light from the side of the object at a predetermined position in the moving path of the object and wherein said light receiving means is disposed above the object at the predetermined position and receives the light having been transmitted upward by the object.

65. The internal quality measuring apparatus according to claim 64, further comprising a shield plate located beside the object at said predetermined position and at a position lower than a height of the object and higher than a projection light position of the light from said light projecting means onto the object, said shield plate being provided for shielding said light receiving means from stray light.

66. The internal quality measuring apparatus according to claim 65, wherein said light projecting means and shield plates are disposed on either side of said moving means and a separation between the two shield plates is adjustable.

67. The internal quality measuring apparatus according to claim 66, further comprising lateral diameter measuring means disposed upstream of said predetermined position in said moving path and arranged to measure a lateral diameter of said object, and adjusting means for adjusting the separation between said shield plates, based on an output from the lateral diameter measuring means.

68. The internal quality measuring apparatus according to claim 64, further comprising a shield plate disposed at a height higher than a height of the object at said predetermined position and arranged to shield said light receiving means from stray light.

69. The internal quality measuring apparatus according to claim 68, further comprising height measuring means disposed upstream of said predetermined position in said moving path and arranged to measure the height of said object, and adjusting means for adjusting the height of said shield plate, based on an output from the height measuring means.

70. The internal quality measuring apparatus according to claim 64, further comprising size measuring means disposed upstream of said predetermined position in said moving path and arranged to measure at least one of a height and a lateral diameter of said object, a shield plate for shielding said light receiving means from stray light, said shield plate being disposed near the object at said predetermined position and being capable of being pivoted about a predetermined horizontal axis, and adjusting means for adjusting an angular position about said horizontal axis of said shield plate, based on an output from said size measuring means, so as to decrease a gap between said shield plate and the object at said predetermined position.

71. The internal quality measuring apparatus according to claim 64, further comprising a shield plate for shielding said light receiving means from stray light, said shield plate being disposed near the object at said predetermined position and being capable of being pivoted about a predetermined horizontal axis, said shield plate being pushed up by the object to be pivoted about said horizontal axis as said object is moved by said moving means to approach said predetermined position, whereby the shield plate shields the light receiving means from the stray light with being in a contact state with the object when the object is located at said predetermined position.

72. The internal quality measuring apparatus according to claim 71, wherein said shield plate is provided with an upward curl for permitting the shield plate to move away when it touches the object, at a corner on the upstream side of said moving path and on the contact side with the object in said shield plate.

73. The internal quality measuring apparatus according to claim 64, further comprising a tray fixed on said moving means and arranged to receive said object, said tray covering at least part of the object received thereon and having an aperture bored so as to permit the light from said light projecting means to reach the object.

74. An internal quality measuring apparatus for measuring an internal quality of an object, said measuring apparatus comprising:

conveying means for continuously conveying an object;

detecting means for detecting a spacing between objects mounted on said conveying means;

light projecting means for projecting light to the object;

light receiving means for measuring light having been transmitted by the object;

shield means for intercepting the light incident to said light receiving means;

light amount adjusting means for adjusting an amount of the light projected from said light projecting means; and control means for controlling an amount of the light incident to said light receiving means, based on a result of the detection by said detecting means;

wherein while it is determined based on the detection by said detecting means that the spacing between the objects on said conveying means is less than a predetermined value, said control means makes said light projecting means project the light to the object without intervention of said light amount adjusting means and makes the light receiving means measure the light having been transmitted through the object;

wherein when it is determined based on the detection by said detecting means that the spacing between the objects on said conveying means is not less than the predetermined value, said control means makes said light amount adjusting means adjust the amount of the light incident to said light receiving means and makes said light receiving means measure the amount of the light thus adjusted;

said measuring device further comprising arithmetic operation means for correcting a result of the measurement by said light receiving means, based on a result of measurement by said light receiving means when said control means controls the amount of the incident light and a result of measurement by said light receiving means when said shield means intercepts the incident light.

75. The internal quality measuring apparatus according to claim 74, wherein when it is determined based on the detection by said detecting means that the spacing between the objects on said conveying means is not less than the predetermined value, said control means makes said light amount adjusting means adjust the amount of the light incident to said light receiving means, makes said light receiving means measure the amount of the light thus adjusted, thereafter further makes said shield means intercept the light incident to said light receiving means, and makes said light receiving means measure an amount of light in this state; or said control means makes said shield means intercept the light incident to said light receiving means, makes said light receiving means measure the amount of light in this state, thereafter releases said shield means from the intercepting state of the light incident to said light receiving means, makes said light amount adjusting means adjust the amount of the light incident to said light receiving means, and makes said light receiving means measure the amount of the light thus adjusted.

76. A correction method for measurement of an internal quality of an object, the measurement comprising steps of radiating light toward the object and analyzing light scattered inside the object and emitted from the object by spectral analysis, said correction method comprising:

a step of carrying out the measurement with a pseudo-object member containing an aqueous solution obtained by dissolving a solute in water, and a step of correcting a result of the measurement of the object, based on a result of the measurement with the pseudo-object member.

77. The correction method according to claim 76, wherein a light diffusing body is mixed in said aqueous solution.

78. The correction method according to claim 76 or 77, wherein said correction is carried out based on a difference between a value obtained in the measurement with said pseudo-object member and a predetermined reference value.

79. The correction method according to claim 76 or 77, further comprising steps of measuring a temperature of said pseudo-object member and further carrying out the correction based on a result of the measurement of the temperature.

80. The correction method according to claim 76 or 77, wherein said solute is an acid.

81. The correction method according to claim 80, wherein said acid is citric acid.

82. The correction method according to claim 76 or 77, wherein said solute is a sugar.

83. The correction method according to claim 82, wherein said sugar is cane sugar.

84. The correction method according to claim 76 or 77, wherein said solute is an acid and a sugar.

85. An internal quality measuring apparatus for measuring an internal quality of an object on a non-destructive basis, said measuring apparatus comprising:
   light projecting means for projecting light toward an object;
   support means for supporting the object;
   measuring means for measuring light having been transmitted through the object;
   projection light amount control means for controlling a projection light amount according to a kind of the object, said projection light amount control means comprising a shield plate having a plurality of small holes and shield plate moving means for moving said shield plate, one of said small holes being located by said shield plate moving means on an optical axis of said light projecting means and the object, according to the size of the object; and
   position control means for controlling locations of said light projecting means, said support means, and said measuring means, according to a size of the object.

86. The internal quality measuring apparatus according to claim 85, wherein said shield plate is of a rectangular shape, a plurality of the small holes are provided on an arbitrary straight line within a surface of the shield plate, and said shield plate is arranged to be moved on the straight line by said shield plate moving means.

87. The internal quality measuring apparatus according to claim 85, wherein said shield plate is of a circular shape, a plurality of the small holes are provided at positions an equal distance apart from the center of the circle within a surface of the shield plate, and said shield plate is arranged to be rotated about the center by said shield plate moving means.

88. An internal quality measuring apparatus for measuring an internal quality of an object on a non-destructive basis, said measuring apparatus comprising:
   light projecting means for projecting light toward an object;
   support means for supporting the object;
   measuring means for measuring light having been transmitted through the object;
   projection light amount control means for controlling a projection light amount according to a kind of the object;
   position control means for controlling locations of said light projecting means, said support means, and said measuring means, according to a size of the object;
   conveying means for continuously conveying the object; and
   detecting means for detecting a diameter of the object, wherein said light projecting means projects the light to a region around an equator part of the object conveyed while said position control means controls the locations of said light projecting means, said support means, and said measuring means, based on a result of the detection by said detecting means.

89. An internal quality measuring apparatus comprising:
   moving means for moving objects mounted at random thereon; and
   measuring means disposed in a moving path of the objects by the moving means and arranged to project light toward an object under movement and measure light having been transmitted through the object, wherein an internal quality of the object is measured based on an output from the measuring means,
   said measuring apparatus comprising:
   upstream detecting means disposed upstream of said measuring means in said moving path and arranged to detect a position of the object on said moving means;
   monitor means for monitoring a moving amount of said moving means; and
   control means for performing such a control that the measuring means performs the measurement when said object on the moving means passes a measurement position of said measuring means, based on outputs from said upstream detecting means and said monitor means.

90. The internal quality measuring apparatus according to claim 89, wherein said upstream detecting means detects a lateral diameter in a moving direction of the object and wherein said control means calculates a center position in the moving direction of the object, based on the lateral diameter detected, and said control means performs such a control that the measuring means performs the measurement when the center of the object passes the measurement position of the measuring means.

91. The internal quality measuring apparatus according to claim 89 or 90, further comprising:
   downstream detecting means disposed downstream of said measuring means in said moving path and arranged to detect a position of the object on said moving means; and
   error determining means for comparing the position of the object on the moving means, detected by said upstream detecting means, with the position of the same object on the moving means, detected by said downstream detecting means, and for determining that a measurement error was made, when there is a deviation between the two positions.

92. The internal quality measuring apparatus according to claim 90, further comprising:
   downstream detecting means disposed downstream of said measuring means in said moving path and arranged to detect a lateral diameter of said object in the moving direction; and
   error determining means for comparing a lateral diameter of the object in the moving direction, detected by said upstream detecting means, with a lateral direction of the object in the moving direction, detected by said downstream detecting means, and for determining that a measurement error was made, when there is a deviation between the two lateral diameters.

93. The internal quality measuring apparatus according to claim 92, further comprising classifying means for classifying an object with which said error determining means determined that a measurement error was made, as an object to be measured again.

94. A control method for controlling an internal quality measuring apparatus comprising:
   moving means for moving objects mounted at random thereon; and
   measuring means disposed in a moving path of the objects by the moving means and arranged to project light toward an object under movement and measure light having been transmitted through the object, wherein an internal quality of the object is measured based on an output from the measuring means, said control method comprising:

a step of detecting a position of said object on said moving means on an upstream side of an object measurement position by said measuring means in said moving path;

a step of detecting a position of said object on said moving means on a downstream side of the object measurement position by said measuring means in said moving path; and a step of determining that a measurement error was made, when there is a deviation between said position detected on the upstream side and said position detected on the downstream side.

95. An internal quality measuring apparatus for evaluating an internal quality of an object thereto, said measuring apparatus comprising:

moving means for moving an object mounted thereon;

light projecting means for projecting light from the side of the object thereto, at a predetermined position in a moving path of the object by the moving means;

light receiving means disposed above the object at said predetermined position and arranged to receive light having been transmitted upward by the object; and a shield plate located beside the object at said predetermined position and at a position lower than a height of the object and higher than a projection light position of the light from said light projecting means onto the object, said shield plate being provided for shielding said light receiving means from stray lights wherein the internal quality of the object is evaluated based on light incident to said light receiving means.

96. The internal quality measuring apparatus according to claim 95, wherein said light projecting means and shield plates are disposed on either side of said moving means and a separation between the two shield plates is adjustable.

97. The internal quality measuring apparatus according to claim 96, further comprising lateral diameter measuring means disposed upstream of said predetermined position in said moving path and arranged to measure a lateral diameter of said object, and adjusting means for adjusting the separation between said shield plates, based on an output from the lateral diameter measuring means.

98. An internal quality measuring apparatus for evaluating an internal quality of an object thereto, said measuring apparatus comprising:

moving means for moving an object mounted thereon;

light projecting means for projecting light from the side of the object thereto, at a predetermined position in a moving path of the object by the moving means;

light receiving means disposed above the object at said predetermined position and arranged to receive light having been transmitted upward by the object; and a shield plate disposed at a height higher than a height of the object at said predetermined position and arranged to shield said light receiving means from stray light, wherein the internal quality of the object is evaluated based on light incident to said light receiving means.

99. The internal quality measuring apparatus according to claim 98, further comprising height measuring means disposed upstream of said predetermined position in said moving path and arranged to measure a height of said object, and adjusting means for adjusting the height of said shield plate, based on an output from the height measuring means.

100. An internal quality measuring apparatus for evaluating an internal quality of an object thereto, said measuring apparatus comprising:

moving means for moving an object mounted thereon;

light projecting means for projecting light from the side of the object thereto, at a predetermined position in a moving path of the object by the moving means;

light receiving means disposed above the object at said predetermined position and arranged to receive light having been transmitted upward by the object;

size measuring means disposed upstream of said predetermined position in said moving path and arranged to measure at least one of a height and a lateral diameter of said object;

a shield plate for shielding said light receiving means from stray light, said shield plate being disposed near the object at said predetermined position and being capable of being pivoted about a predetermined horizontal axis; and adjusting means for adjusting an angular position about said horizontal axis of said shield plate, based on an output from said size measuring means, so as to decrease a gap between said shield plate and the object at said predetermined position, wherein the internal quality of the object is evaluated based on light incident to said light receiving means.

101. An internal quality measuring apparatus for evaluating an internal quality of an object thereto, said measuring apparatus comprising:

moving means for moving an object mounted thereon;

light protecting means for projecting light from the side of the object thereto, at a predetermined position in a moving path of the object by the moving means;

light receiving means disposed above the object at said predetermined position and arranged to receive light having been transmitted upward by the object; and a shield plate for shielding said light receiving means from stray light, said shield plate being disposed near the object at said predetermined position and being capable of being pivoted about a predetermined horizontal axis, said shield plate being pushed up by the object to be pivoted about said horizontal axis as said object is moved by said moving means to approach said predetermined position, whereby the shield plate shields the light receiving means from the stray light with being in a contact state with the object when the object is located at said predetermined position, wherein the internal quality of the object is evaluated based on light incident to said light receiving means.

102. The internal quality measuring apparatus according to claim 101, wherein said shield plate is provided with an upward curl for permitting the shield plate to move away when it touches the object, at a corner on the upstream side of said moving path and on the contact side with the object in said shield plate.

103. An internal quality measuring apparatus for evaluating an internal quality of an object thereto, said measuring apparatus comprising:

moving means for moving an object mounted thereon;

light projecting means for projecting light from the side of the object thereto, at a predetermined position in a moving path of the object by the moving means;

light receiving means disposed above the object at said predetermined position and arranged to receive light having been transmitted upward by the object; and a tray fixed on said moving means and arranged to receive said object, said tray covering at least part of the object received thereon and having an aperture bored so as to permit the light from said light projecting means to reach the object, wherein the internal quality of the object is evaluated based on light incident to said light receiving means.

104. An internal quality measuring apparatus for measuring an internal quality of an object on a nondestructive basis, said measuring apparatus comprising:

conveying means for continuously conveying an object;

detecting means for detecting a spacing between objects mounted on said conveying means;

light projecting means for projecting light to the object;

light receiving means for receiving light having been transmitted through the object;

a first optical fiber having one end located at a position where the light projected from said light projecting means can be received directly and the other end connected to said light receiving means, said first optical fiber receiving the light from said light projecting means without intervention of the object;

light amount adjusting means disposed at the end or in the middle of an optical path of said first optical fiber and arranged to adjust an amount of light passing through said first optical fiber;

first shield means disposed at the end or in the middle of the optical path of said first optical fiber and arranged to intercept the light passing through said first optical fiber;

a second optical fiber having one end located at a position where the light emitted from the object can be received and the other end connected to said light receiving means, said second optical fiber receiving the light having been transmitted through the object;

second shield means disposed at the end or in the middle of an optical path of said second optical fiber and arranged to intercept light passing through said second optical fiber; and control means for controlling operations of said first shield means and said second shield means, based on the result of the detection by said detecting means;

wherein while it is determined based on the detection by said detecting means that the spacing between the objects on said conveying means is less than a predetermined value, said control means makes said first shield means shield said first optical fiber and makes said light receiving means measure light incident thereto from said second optical fiber;

wherein when it is determined based on the detection by said detecting means that the spacing between the objects on said conveying means is not less than the predetermined value, said control means makes said second shield means shield said second optical fiber and makes said light receiving means measure light incident thereto from said first optical fiber through said light amount adjusting means;

said measuring apparatus further comprising:

arithmetic operation means for correcting a result of the measurement by said light receiving means, based on a result of measurement by said light receiving means when the amount of the incident light is controlled by said control means and a result of measurement by said light receiving means when said shield means intercepts the incident light.

105. The internal quality measuring apparatus according to claim 104, further comprising measuring means for making said second shield means shield said second optical fiber at an arbitrary time, irrespective of the result of the detection by said detecting means, and for making said light receiving means measure the light incident thereto from said first optical fiber through said light amount adjusting means.

106. The internal quality measuring apparatus according to claim 104 or 105, wherein when it is determined based on the detection by said detecting means that the spacing between the objects on said conveying means is not less than the predetermined value, said second shield means is made to shield said second optical fiber, said light receiving means is made to measure the light incident thereto from said first optical fiber through said light amount adjusting means, thereafter said first shield means is further made to shield said first optical fiber, and said light receiving means is made to measure light with said first optical fiber and said second optical fiber being in a shielded state; or said first shield means and said second shield means are made to shield said first optical fiber and said second optical fiber, said light receiving means is made to measure the light with said first optical fiber and said second optical fiber being in the shielded state, thereafter said first shield means is opened to open said first optical fiber, and said light receiving means is made to measure the light incident thereto from said first optical fiber through said light amount adjusting means.

* * * * *